United States Patent
Kunjapur et al.

(10) Patent No.: US 11,649,450 B2
(45) Date of Patent: May 16, 2023

(54) METHODS OF MAKING PROTEINS WITH NON-STANDARD AMINO ACIDS

(71) Applicant: President and Fellows of Harvard College, Cambridge, MA (US)

(72) Inventors: Aditya Mohan Kunjapur, Cambridge, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 368 days.

(21) Appl. No.: 16/627,077

(22) PCT Filed: Jun. 29, 2018

(86) PCT No.: PCT/US2018/040226
§ 371 (c)(1),
(2) Date: Dec. 27, 2019

(87) PCT Pub. No.: WO2019/006260
PCT Pub. Date: Jan. 3, 2019

(65) Prior Publication Data
US 2020/0140852 A1 May 7, 2020

Related U.S. Application Data

(60) Provisional application No. 62/526,671, filed on Jun. 29, 2017.

(51) Int. Cl.
| | | |
|---|---|---|
| C12N 15/10 | (2006.01) | |
| C12N 9/52 | (2006.01) | |
| C12N 9/00 | (2006.01) | |
| C12N 15/74 | (2006.01) | |
| C12N 15/90 | (2006.01) | |

(52) U.S. Cl.
CPC .......... C12N 15/1058 (2013.01); C12N 9/52 (2013.01); C12N 9/93 (2013.01); C12N 15/74 (2013.01); C12N 15/90 (2013.01); *C12Y 601/01* (2013.01)

(58) Field of Classification Search
CPC ........ C12N 15/1058; C12N 9/52; C12N 9/93; C12N 15/90; C12N 15/10; C12N 15/63; C12N 15/74; C12Y 601/01
See application file for complete search history.

(56) References Cited

U.S. PATENT DOCUMENTS

| | | |
|---|---|---|
| 2005/0287639 A1 | 12/2005 | Kwon et al. |
| 2008/0090999 A1 | 4/2008 | Goldman et al. |
| 2008/0153130 A1 | 6/2008 | Plucienniczak et al. |

FOREIGN PATENT DOCUMENTS

| | | |
|---|---|---|
| WO | 2016/069726 A1 | 5/2016 |
| WO | 2018/0148516 A1 | 8/2018 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Dougan, DA et al. Engineering a tRNA and Amino acyl-tRNA Synthetase for the Site-Specific Incorporation of Unnatural Amino Acids into Proteins in Vivo. Proceedings of the National Academy of Sciences of the United States of America. Sep. 16, 1997; vol. 94, No. 19; pp. 10092-10097; abstract; p. 10095, col. 2, paragraph 1-2.
Graciet, Emmanuelle et al. "Aminoacyl-transferases and the N-end rule pathway of prokaryotic/eukaryotic specificity in a human pathogen". Proceedings of the National Academy of Science. Feb. 28, 2006, vol. 103, No. 9; pp. 3078-3083; p. 3078, 2nd column, 2nd paragraph; p. 3083, 1st column, 3rd paragraph; DOI: 10.1073/pnas. 0511224103.
Grunenfelder, Bjorn et al. Identification of the Protease and the Turnover Signal Responsible for Cell Cycle-Dependent Degradation of the Caulobacter FliF Motor Protein. Journal of Bacteriology. Aug. 2004; vol. 186, No. 15; pp. 4960-4971; abstract; p. 4961, col. 1, paragraph 2; p. 4961, col. 2, paragraph 3; Doi: 10.1128/JB.186. 15.4960-4971.2004.
International Search Report and Written Opinion based on PCT/US2018/040226 dated Oct. 2, 2018.
Kunjapur, Aditya M. et al. Engineering Post-Translational Proofreading to Discriminate Nonstandard Amino Acids. Proceedings of the National Academy of Sciences of the United States of America. Jan. 4, 2018; vol. 115, No. 3; pp. 619-624; whole document; DOI: 10.1073/pnas.1715137115.
Liu, David R. et al. Engineering a tRNA and Aminoacyl-tRNA Synthetase for the Site-Specific Incorporation of Unnatural Amino Acids into Proteins In Vivo. Proceedings of the National Academy of Sciences of the United States of America. Sep. 16, 1997; vol. 94, No. 19; pp. 10092-10097; abstract; p. 10095, col. 2, paragraphs 1-2.
Roman-Hernandez, Giselle et al. The ClpS Adaptor Mediates Staged Delivery of N-End-Rule Substrates to the AAA+ ClpAP Protease. Molecular Cell. Jul. 22, 2011; vol. 43, No. 2; pp. 1-22; abstract; p. 8, paragraph 4; DOI: 10.1016/j.molcel.2011.06.009.

* cited by examiner

*Primary Examiner* — Iqbal H Chowdhury
(74) *Attorney, Agent, or Firm* — Banner & Witcoff, Ltd.

(57) ABSTRACT

The disclosure provides methods of making a protein having a desired non-standard amino acid incorporated at its N-terminus in a cell and methods of screening for an amino acyl tRNA synthetase variant that preferentially selects a non-standard amino acid against its standard amino acid counterpart or undesired non-standard amino acids for incorporation into a protein in a cell.

18 Claims, 13 Drawing Sheets

Specification includes a Sequence Listing.

FIG. 1A

| OTS Family | Source | SAA Analog | |
|---|---|---|---|
| TyrRS | *M. jannaschii* | Y/F | Orthogonal in Prokaryotes |
| TrpRS | *S. cerevisiae* | W | Orthogonal in Prokaryotes |
| PylRS | *Methanosarcina* | K or Y/F | Orthogonal in Eukaryotes |
| TyrRS | *E. coli* | Y/F | Orthogonal in Eukaryotes |
| LeuRS | *E. coli* | L | Orthogonal in Eukaryotes |

FIG. 7A

SEQ ID NOS: 149-158, top down, in order of appearance

FIG. 7B

SEQ ID NOS: 149, 159-160, top down, in order of appearance

METHODS OF MAKING PROTEINS WITH NON-STANDARD AMINO ACIDS

RELATED APPLICATIONS

This application is a National Stage Application under 35 U.S.C. 371 of co-pending PCT application PCT/US18/40226 designating the United States and filed Jun. 29, 2018; which claims the benefit of U.S. provisional application No. 62/526,671 filed on Jun. 29, 2017 each of which are hereby incorporated by reference in their entireties.

STATEMENT OF GOVERNMENT INTERESTS

This invention was made with government support under DE-FG02-02ER63445 awarded by Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Aug. 8, 2018, is named 010498_01111WO_SL.txt and is 52,932 bytes in size.

FIELD

The present invention relates in general to methods of making proteins with non-standard amino acids.

BACKGROUND

Naturally-occurring (standard) amino acids (SAAs) are the 20 unique building blocks composing all proteins derived from biological systems. Non-standard amino acids (NSAAs) have been developed bearing functional groups beyond those encoded by the 20 standard amino acids. To date, more than 70 non-standard amino acids (NSAAs) have been developed for in vivo protein translation. See Liu et al., *Annual Review of Biochemistry* 79:413-444 (2010). Methods of incorporating NSAAs into proteins using engineered amino-acyl tRNA synthetases and transfer RNAs also inadvertently incorporate standard amino acids and non-target NSAAs due to promiscuity or nonspecificity of the engineered amino-acyl tRNA synthetases and transfer RNAs corresponding to the NSAAs. Recently, in vivo *Escherichia coli* orthogonal translation systems (OTSs) having engineered tRNA and aminoacyl-tRNA synthetase pairs that reassign the amber stop codon (UAG) were developed to characterize the performance of these orthogonal translation systems (OTSs) with respect to the efficiency and accuracy of NSAA incorporation. It was shown that in vivo incorporation of amino acids into reporter proteins (and thus reporter synthesis) at reassigned amber codons may not discriminate between standard and non-standard amino acids. See Monk J W, et al. (2016) Rapid and Inexpensive Evaluation of Nonstandard Amino Acid Incorporation in *Escherichia coli*. *ACS Synthetic Biology*. One method of determining the fidelity of NSAA incorporation includes in vitro protein purification followed by low-throughput mass spectrometry. Such an approach confirms the promiscuity of at least one *E. coli* OTS system (*Methanococcus jannaschii* tyrosyl-tRNA synthetase (MjTyrRS)-derived orthogonal synthetases). See Young T S, Ahmad I, Yin J A, & Schultz P G (2010) An Enhanced System for Unnatural Amino Acid Mutagenesis in *E. coli*. *Journal of Molecular Biology* 395 (2):361-374. Misincorporation of a standard amino acid for a nonstandard amino acid may be detrimental in the production of antibodies containing NSAAs for conjugation or the production of biomaterials containing NSAAs for tunable properties. The incorporation of SAAs instead of NSAAs represents the formation of impurities and the heterogeneous mixture lowers yields. Improvements in synthetase and tRNA specificity or selectivity can improve rate of NSAA incorporation. However, analyzing the polypeptide for rate of NSAA incorporation is laborious making modification of the synthetase or tRNA in response to experimental results a slow process. See Santoro S W, Wang L, Herberich B, King D S, & Schultz P G (2002) An efficient system for the evolution of aminoacyl-tRNA synthetase specificity. *Nat Biotech* 20(10):1044-1048; and Amiram M, et al. (2015) Evolution of translation machinery in recoded bacteria enables multi-site incorporation of nonstandard amino acids. *Nat Biotech* 33(12):1272-1279.

There is a continuing need in the art to develop methods of making proteins with NSAAs with improved efficiency and accuracy and for modifying synthetases or tRNA to result in improved efficiency and accuracy.

SUMMARY

The present disclosure provides a method for selectively degrading proteins having a standard amino acid at an amino acid target location within a mixture or collection or population of proteins including proteins having a nonstandard amino acid at the amino acid target location. In this context, the standard amino acid may be considered an undesired amino acid. The present disclosure also provides a method for selectively degrading proteins having an undesired non-target NSAA at an amino acid target location within a mixture or collection or population of proteins including proteins having a desired nonstandard amino acid at the amino acid target location. In this context, the undesired non-target NSAA may be considered an undesired amino acid. Aspects of the disclosure utilize methods and materials described herein to distinguish between different NSAAs at an amino acid target location when more than one NSAA is used during the synthesis procedure, such as when multiple different NSAAs are used simultaneously in vivo. According to one aspect, an in vivo methods are provided that can discriminate between NSAAs competing for incorporation at the same site of a protein.

According to one aspect, the methods may be carried out in vivo, i.e. within a cell. According to one aspect, methods of making target polypeptides having a non-standard amino acid substitution at an amino acid target location and methods of degrading target polypeptides having a standard amino acid substitution or an undesired NSAA (either referred to as an undesired amino acid) at the amino acid target location may be carried out in vivo, i.e. within a cell. According to one aspect, a target polypeptide is made which includes a non-standard amino acid at an amino acid target location using an engineered amino-acyl tRNA synthetase and a transfer RNA corresponding to the non-standard amino acid. A removable protecting group is attached to the target polypeptide adjacent to the amino acid target location, such that when the removable protecting group is removed, an N-end amino acid is exposed at the amino acid target location. Should the engineered amino-acyl tRNA synthetase and a transfer RNA add an undesired amino acid, i.e., a standard amino acid or an undesired NSAA, instead of the desired non-standard amino acid at the amino acid target location, methods are provided herein for degrading the target polypeptide including the undesired amino acid, i.e. a standard amino acid or an undesired NSAA, at the amino acid target location, such as by using the N-end rule pathway for protein degradation. According to one aspect, post-translational proofreading is used to distinguish correctly translated from incorrectly translated proteins. The disclosure provides a post-translational proofreading concept that results in protein degradation in a cell using the N-end rule unless the desired NSAA is incorporated at the N-terminus of the protein.

According to one aspect, the target polypeptide is made within a cell, i.e. in vivo, and the cell produces a protease and may also produce an adapter protein for the protease, i.e. a degradation system. Certain cells, such as E. coli, naturally produce the protease system ClpAP and the adaptor ClpS, and both components are present in order for the N-end rule degradation pathway to function. According to certain aspects, adaptor variants such as ClpS variants may be used which have different specificities than the natural ClpS. In this context, cell production of the natural ClpS be inactivated, for example, such as by gene modification where the ClpS gene sequence in the genome is modified to introduce premature stop codons. Such degradation systems are representative of a cellular system that degrades proteins according to the N-end rule pathway for protein degradation as is known in the art. According to the N-end rule, the half-life of a protein is determined by its N-terminal residue. An N-terminal residue is said to be destabilizing if it is recognized by a cellular degradation system, which in turn leads to degradation of the protein. If the N-terminal residue is not destabilizing, i.e, it is not recognized by a cellular degradation system, then the protein is not subject to the N-end rule pathway for protein degradation. Destabilizing amino acids may be natural amino acids. Destabilizing amino acids may be certain NSAAs. Destabilizing amino acids may be referred to as undesired amino acids. Stabilizing amino acids may be referred to as desired amino acids. Non-standard amino acids, such as analogs to natural amino acids, may be stabilizing or destabilizing amino acids. Certain non-standard amino acids, such as analogs to natural amino acids, may be resistant to degradation by cellular systems. In this manner, the method increases production (yield) of proteins having a desired amino acid, i.e., a stabilizing amino acid or an amino acid which is not destabilizing, such as certain non-standard amino acids, insofar as such a protein may not be subject to the N-end rule pathway for protein degradation. In this manner, the method decreases production (yield) of proteins having an undesired amino acid, such as a standard amino acid or a certain NSAA, insofar as such a protein may be subject to the N-end rule pathway for protein degradation. In this manner, the method determines successful desired NSAA incorporation to the extent that target polypeptides that include an undesired amino acid, such as a standard amino acid or a certain destabilizing NSAA (undesired NSAA), at the amino acid target location may be degraded and target polypeptides that include a desired non-standard amino acid at the amino acid target location remain and may not be degraded.

The present disclosure provides a method of optimizing production of proteins including a non-standard amino acid. Reaction conditions are provided for making a target polypeptide including a non-standard amino acid substitution at an amino acid target location using an engineered amino-acyl tRNA synthetase and a transfer RNA as is known in the art. A removable protecting group is attached to the target polypeptide adjacent to the amino acid target location, such that when the removable protecting group is removed, an N-end amino acid is exposed at the amino acid target location. Should the engineered amino-acyl tRNA synthetase and a transfer RNA add a standard amino acid or undesired NSAA instead of the desired non-standard amino acid at the amino acid target location, methods are provided herein for degrading the target polypeptide including the standard amino acid or undesired NSAA at the amino acid target location. The amount of proteins having a desired non-standard amino acid is determined. Given the amount of protein produced, the reaction conditions and/or the amino-acyl tRNA synthetase and/or tRNA are altered and the amount of proteins having the desired non-standard amino acid is again determined. The process is repeated until the process is optimized for a desired yield of protein including desired NSAA. Exemplary reaction conditions which may be altered according to the present disclosure include changes of culture media or concentration of desired NSAA. Alterations or changes to the amino-acyl tRNA synthetase and/or tRNA include one or more mutations that may improve performance of the amino-acyl tRNA synthetase and/or tRNA. Such mutations may be made by methods known to those of skill in the art such as random mutagenesis approaches such as error-prone polymerase chain reaction (PCR) or directed approaches such as site-saturation mutagenesis or rational point mutagenesis.

The present disclosure provides a method of distinguishing a protein having a nonstandard amino acid, i.e. a desired nonstandard amino acid, at an amino acid target location from a protein having a standard amino acid or undesired nonstandard amino acid at the amino acid target location by degrading the protein if a destabilizing amino acid (i.e., standard amino acid or undesired destabilizing NSAA) recognized by a protease is present at the amino acid target location.

The present disclosure provides a method of making a target protein using an amino-acyl tRNA synthetase engineered or designed to incorporate a target nonstandard amino acid (i.e., a desired NSAA) in the target protein at an amino acid target location, wherein a removable protecting group is adjacent the amino acid target location. The removable protecting group is removed to expose the amino acid target location in the presence of a degradation enzyme or degradation enzyme/adaptor complex. According to certain aspects, the adaptor discriminates between amino acids and accordingly whether degradation will occur by the degradation enzyme. According to one aspect, the degradation enzyme/adaptor complex degrades the target protein if a standard amino acid or undesired NSAA is present at the amino acid target location. If the desired nonstandard amino acid is present at the amino acid target location, then the degradation enzyme/adaptor complex is ineffective to degrade the target protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIGS. 1A to 1F illustrate Post-Translational Proofreading (PTP) proof of concept. FIG. 1A shows the most commonly used OTSs. FIG. 1B shows the NSAAs used in this study (full chemical names in SI). FIG. 1C shows the percentages of observed incorporation at target site of Ub-X-GFP protein in the absence of BipA after digestion and mass spectrometry. FIG. 1D shows the scheme for PTP consisting of N-end exposure and recognition steps applied to synthetic substrates. FIGS. 1E and 1F show incorporation assay showing fluorescence resulting from GFP expression normalized by optical density (FL/OD) in the absence/presence of BipA and expression of various OTS or PTP components. Expression of the orthogonal tRNA alone was not responsible for GFP synthesis in the absence of BipA, but expression of the BipARS/tRNA pair resulted in levels of FL/OD nearly as high in the absence of BipA as in the presence of BipA. Significant reduction of the FL/OD signal in the absence of BipA occurs upon expression of Ubp1, which cleaves the ubiquitin domain and exposes the amino acid corresponding to the first UAG codon as the N-terminal residue. The decrease in signal only in the absence of BipA suggests that BipARS was primarily mischarging tRNA with N-terminally destabilizing residues. The FL/OD signal in the absence of BipA further decreased upon expression of ClpS, suggesting that the rate of N-end discrimination was previously limiting.

FIG. 2A shows an illustration of PTP with original Ub-X-GFP reporter in "Off" and "On" states to alternate between quantifying total incorporation or only intended incorporation. FIG. 2B shows an incorporation assay with PTP "Off" for various OTSs in the absence/presence of cognate substrates reveals generally high activity on SAAs. FIG. 2C shows an incorporation assay with PTP "On" reveals consistent minimization of SAA-based signal but also potential degradation of pAzF and 5OHW. These results demonstrate that many tested AARSs mischarge tRNA in the absence of their intended NSAA, and that post-translational proofreading with wild-type ClpS can resolve differences for several of these AARS/NSAA pairs.

FIG. 3A shows heatmap of FL/OD signals obtained from an NSAA panel arranged roughly in descending size with PTP "Off" in first column and PTP "On" in second column. Top panel reflects activity of BipyA OTS and bottom reflects pAcF OTS. FIG. 3B shows a cartoon generated from crystal structure of E. coli ClpS binding N-end Phe peptide (PDB ID: 3O2B) showing four hydrophobic ClpS residues subjected to mutation. FIG. 3C shows heatmap of FL/OD signals obtained using a ClpS-host expressing UBP1, the pAcF OTS, and variants of ClpS in the presence of different NSAAs. FIG. 3D shows a cartoon generated from crystal structure of C. crescentus ClpS binding N-end Trp peptide (PDB ID: 3GQ1). FIG. 3E shows an FL/OD heatmap resulting from expression of UBP1, the 5OHW OTS, and ClpS variants in the presence/absence of 5OHW. Legend same as in panel C. FIG. 3F shows an FL/OD heatmap resulting from expression of UBP1/ClpS in strains with Ub-X-GFP reporter genes hard-coded to express SAAs in place of X.

FIG. 5A shows a control experiment that demonstrates the expected effect of Ubp1/ClpS expression on FL/OD signal resulting from GFP protein with N-terminal UCG, UAC, or UAG codons. FIG. 5B shows the FL/OD as a function of the number of UAG codons.

FIG. 6A shows results using a genomically integrated Ub-UAG-Bla selectable marker, where Bla is a beta-lactamase conferring resistance to carbenicillin if fully expressed and stabilized. FIG. 6B shows results using a genomically integrated Ub-UAG-Cat selectable marker, where Cat is a chloramphenicol acetyltransferase conferring resistance to chloramphenicol if fully expressed and stabilized.

FIGS. 7A-7B show sequence alignment sampling natural diversity of ClpS. FIG. 7A shows ten bacterial sequences were obtained from UniProt and aligned using Clustal Omega. FIG. 7A discloses SEQ ID NOS 149-158, respectively, in order of appearance. FIG. 7B shows E. coli ClpS sequence alignment with UBR1 homologs present in yeast and humans. The four candidate positions for engineering that were identified using the crystal structure appear here to be conserved. However, three positions (32, 43, and 65) show capacity for substitution with other hydrophobic amino acids. FIG. 7B discloses SEQ ID NOS 149 and 159-160, respectively, in order of appearance.

DETAILED DESCRIPTION

Figure 1B:
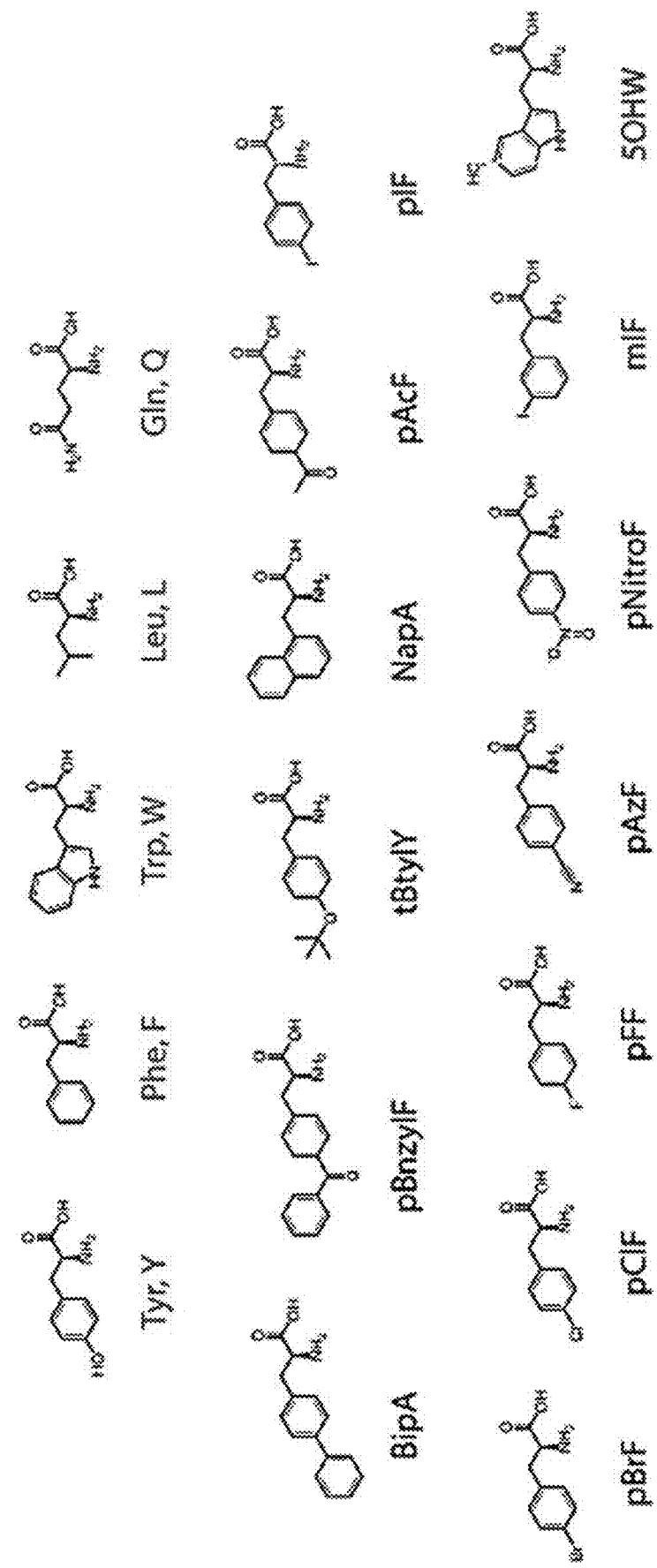

The present disclosure provides a method of making a target polypeptide in a cell, wherein the target polypeptide includes a desired non-standard amino acid substitution at an amino acid target location, i.e. the non-standard amino acid withstands degradation as described herein. As used herein, the terms "polypeptide" and "protein" include compounds that include amino acids joined together by peptide bonds between the carboxyl and amino groups of adjacent amino acid residues. Exemplary cells include prokaryotic cells and eukaryotic cells. Exemplary prokaryotic cells include bacteria, such as E. coli, such as genetically modified E. coli. The method includes genetically modifying the cell to express the target polypeptide including a desired non-standard amino acid substitution at an amino acid target location using an engineered amino-acyl tRNA synthetase and transfer RNA pair corresponding to the non-standard amino acid, and wherein the cell expresses the target polypeptide including a standard amino acid or an undesired NSAA at the amino acid target location when the engineered amino-acyl tRNA synthetase and transfer RNA pair non-selectively adds the standard amino acid or undesired NSAA at the amino acid target location. A removable protecting group is attached to the target polypeptide adjacent to the amino acid target location, such that when the removable protecting group is removed, an N-end amino acid is exposed at the amino acid target location. According to one aspect, the removable protecting group is orthogonal within the cell in which it is being used.

According to certain aspects, the cell includes a protease system for degrading the target polypeptide when the N-end amino acid is a standard amino acid. According to certain aspects, the cell includes a protease system for degrading the target polypeptide when the N-end amino acid is an undesired NSAA. According to certain aspects, the protease system includes an adapter protein and a corresponding protease. The adapter protein coordinates with the protease for degrading the target polypeptide when the N-end amino acid is a standard amino acid. According to one aspect, the protease system is endogenous. According to one aspect, the protease and adaptor can be expressed constitutively. According to one aspect, the protease system is exogenous.

According to one aspect, the protease system is under influence of a promoter. According to one aspect, the adapter protein of the protease system is under influence of an inducible promoter. According to one aspect, the adapter protein is upregulated. According to one aspect, overexpression of adaptor to produce adaptor levels in excess of that found normally within a cell improves degradation of polypeptides having an undesired amino acid at the amino acid target location. According to one aspect, an adaptor protein is provided that facilitates N-end rule classification of an NSAA.

Because the N-end rule pathway of protein degradation is conserved across prokaryotes and eukaryotes, methods described herein are useful in prokaryotes and eukaryotes. The removable protecting groups should be orthogonal in the cell within which it is being used. Ubiquitin is a suitable protecting group in prokaryotic cells because it is orthogonal but it is not a suitable protecting group in eukaryotic cells because it is not orthogonal. In eukaryotic cells, ubiquitin is N-terminally added to proteins often to initiate the process of protein degradation in the proteasome. In addition, the adaptor proteins in eukaryotic cells are homologs of ClpS known as Ubiquitin E3 ligases. According to the present disclosure, ubiquitin E3 ligase domain is altered in order to change the N-end rule classification of an NSAA.

According to one aspect, the removable protecting group is removed to generate an N-end amino acid, and the protease degrades the target polypeptide when the N-end amino acid is a standard amino acid or an undesired NSAA. In this manner, the target polypeptide including a desired non-standard amino acid substitution, i.e. which is resistant to degradation, is enriched within the cell. According to one aspect, embodiments of the disclosure are directed to methods that allow selective degradation of proteins having a standard amino acid or undesired NSAA instead of a desired nonstandard amino acid at their N-termini in a cell. The methods can be used for producing proteins with desired nonstandard amino acids at their N-termini with no detectable impurities.

According to one aspect, a method of identifying the presence of a target polypeptide including a desired non-standard amino acid, i.e. one which is resistant to degradation, is provided. According to this aspect, the target polypeptide includes a detectable moiety attached to the C-end of the target polypeptide. In this manner, if the target polypeptide (and detectable moiety) that is made by the cell is not subject to degradation as described above, then the detectable moiety is detected as a measure of the amount of target polypeptide generated by the cell. Accordingly, a method is provided where a detectable moiety is present at the C-end of the target polypeptide, the removable protecting group is removed to generate an N-end amino acid, the protease (whether accompanied by an adapter protein or not depending upon the protease system being used) degrades the target polypeptide when the N-end amino acid is a standard amino acid or an undesired NSAA, for example, to thereby enrich the target polypeptide including a desired non-standard amino acid substitution, and the detectable moiety is detected as a measure of the amount of the target polypeptide including a desired non-standard amino acid substitution.

According to one aspect, a method is provided for engineering synthetases that are more selective for incorporating non-standard amino acids versus standard amino acids at a selected site in a protein. Since all or substantially all of proteins bearing a standard amino acid or an undesired NSAA at their N-terminus are degraded leaving only proteins with a desired nonstandard amino at their N-terminus, no or substantially no background signal due to standard amino acid or undesired NSAA incorporation results from the method. Synthetases can be evolved and their variants screened in a high-throughput fashion for their function of producing a protein incorporating a nonstandard amino acid, such as a desired NSAA. In this manner, those synthetases with improved function can be identified and modified further to further improve efficiency and selectivity.

I. Methods of Making a Target Polypeptide with an NSAA

In general, methods of making a target polypeptide that includes a non-standard amino acid are known. In general, a cell is genetically modified to include a nucleic acid sequence which encodes for the target polypeptide that includes one or more non-standard amino acids within its amino acid sequence. The cell can be genomically recoded, ("a genomically recoded organsim") to the extent that one or more codons have been reassigned to encode for a non-standard amino acid. For each different non-standard amino acid, an amino-acyl tRNA synthetase/tRNA pair is engineered and the cell is capable of using the amino-acyl tRNA synthetase/tRNA pair to add the corresponding non-standard amino acid (when present in the cell) to a growing peptide sequence. Materials, conditions, and reagents for genetically modifying a cell to make a target protein having one or more amino acid sequences are described in the following references, each of which are hereby incorporated by reference in their entireties.

Approaches to genomically recode organisms include multiplex automatable genome engineering (MAGE), (for example, as described in Wang, Harris H., et al. "Programming cells by multiplex genome engineering and accelerated evolution." *Nature* 460.7257 (2009): 894-898 hereby incorporated by reference in its entirety) and hierarchical conjugative assembly genome engineering (CAGE) (for example, as described in Isaacs, Farren J., et al. "Precise manipulation of chromosomes in vivo enables genome-wide codon replacement." *Science* 333.6040 (2011): 348-353 hereby incorporated by reference in its entirety). In addition, portions of recoded genomes can be synthesized and subsequently assembled, as described recently in an effort to construct a 57-codon organism (for example, as described in Ostrov, Nili, et al. "Design, synthesis, and testing toward a 57-codon genome." *Science* 353.6301 (2016): 819-822 hereby incorporated by reference in its entirety). The modification of an organism, whether recoded or not recoded, in order to express a polypeptide containing a site-specific non-standard amino acid has been described extensively in the literature (for example, as described in Wang, Lei, et al. "Expanding the genetic code of *Escherichia coli.*" *Science* 292.5516 (2001): 498-500; Chin, Jason W., et al. "An expanded eukaryotic genetic code." *Science* 301.5635 (2003): 964-967; Wang, Lei, and Peter G. Schultz. "Expanding the genetic code." *Angewandte chemie international edition* 44.1 (2005): 34-66; Liu, Chang C., and Peter G. Schultz. "Adding new chemistries to the genetic code." *Annual review of biochemistry* 79 (2010): 413-444; Chin, Jason W. "Expanding and reprogramming the genetic code of cells and animals." *Annual review of biochemistry* 83 (2014): 379-408 each of which is hereby incorporated by reference in its entirety). In brief, foreign nucleic acid sequences containing a gene encoding an orthogonal amino-acyl tRNA synthetase and an associated tRNA are introduced into an organism, typically in an expression vector. In addition, a desired non-standard amino acid is added to the cell culture medium. A nucleic acid sequence corresponding to a target protein is modified so that a free codon, such as the UAG codon, is formed at the target site of the gene encoding the target protein. In the presence of these four components—aminoacyl tRNA synthetase protein, tRNA, NSAA, and target protein mRNA—the target protein containing the NSAA is made.

Basic to the present disclosure is the use of an amino-acyl tRNA synthetase/tRNA pair cognate to a nonstandard amino acid. Exemplary amino-acyl tRNA synthetase/tRNA pairs cognate to a nonstandard amino acid are known to those of skill in the art or may be designed for particular nonstandard amino acids, as is known in the art or as described in Wang, Lei, and Peter G. Schultz. "Expanding the genetic code." *Angewandte chemie international edition* 44.1 (2005): 34-66; Liu, Chang C., and Peter G. Schultz. "Adding new chemistries to the genetic code." *Annual review of biochemistry* 79 (2010): 413-444; and Chin, Jason W. "Expanding and reprogramming the genetic code of cells and animals." *Annual review of biochemistry* 83 (2014): 379-408 each of which are hereby incorporated by reference in its entirety.

According to one aspect, the amino-acyl tRNA synthetase/tRNA pair cognate to a nonstandard amino acid is orthogonal to the cellular components of the cell in which it is used. The orthogonality (and therefore the suitability) of exogenous amino-acyl tRNA synthetase/tRNA pairs is dependent on the type of host organism. Four main orthogonal aminoacyl-tRNA synthetases have been developed for genetic code expansion: the *Methanococcus janaschii* tyrosyl-tRNA synthetase (MjTyrRS)/tRNA$_{CUA}$ pair, the *Escherichia coli* tyrosyl-tRNA synthetase (EcTyrRS)/tRNA$_{CUA}$ pair, the *E. coli* leucyl-tRNA synthetase (EcLeuRS)/tRNACUA pair, and pyrrolysyl-tRNA synthetase (PylRS)/tRNA$_{CUA}$ pairs from certain *Methanosarcina*. The MjTyrRS/tRNA$_{CUA}$ pair is orthogonal in *E. coli* but not in eukaryotic cells. The EcTyrRS/tRNA$_{CUA}$ pair and the EcLeuRSARNAcuA pair are orthogonal in eukaryotic cells but not in *E. coli*, whereas the PylRS/tRNA$_{CUA}$ pair is orthogonal in bacteria, eukaryotic cells, and animals (see Chin, Jason W. "Expanding and reprogramming the genetic code of cells and animals." *Annual review of biochemistry* 83 (2014): 379-408 hereby incorporated by reference in its entirety). To maintain orthogonality, the exogenous amino acyl tRNA synthetase should not recognize any native amino acids or native tRNA. To maintain orthogonality, the tRNA should not be recognized by any native amino-acyl tRNA synthetases. To maintain orthogonality, the non-standard amino acid should not be recognized by any native amino acyl tRNA synthetases. "Orthogonal" pairs meet one or more of the above conditions. It is to be understood that "orthogonal" pairs may lead to some mischarging, i.e. such as insubstantial mischarging for example, of orthogonal tRNA with native amino acids so long as sufficient efficiency of charging to the designed NSAA occurs.

Exemplary families of synthetases for bacteria in addition to those described above and incorporated by reference include the PylRS/tRNA$_{CUA}$ pair and the *Saccharomyces cerevisiae* tryptophanyl-tRNA synthetase (ScWRS)/tRNA$_{CUA}$ pair. These exemplary synthetase families have natural analogs (lysine and tryptophan) that are N-end destabilizing amino acids. The following references describe useful synthetase families and their associated NSAAs. Blight, Sherry K., et al. "Direct charging of tRNA$_{CUA}$ with pyrrolysine in vitro and in vivo." *Nature* 431.7006 (2004): 333-335; Namy, Olivier, et al. "Adding pyrrolysine to the *Escherichia coli* genetic code." FEBS letters 581.27 (2007): 5282-5288; Hughes, Randall A., and Andrew D. Ellington. "Rational design of an orthogonal tryptophanyl nonsense suppressor tRNA." *Nucleic acids research* 38.19 (2010): 6813-6830; Ellefson, Jared W., et al. "Directed evolution of genetic parts and circuits by compartmentalized partnered replication." *Nature Biotechnology* 32.1 (2014): 97-101; and Chatterjee, Abhishek, et al. "A Tryptophanyl-tRNA Synthetase/tRNA Pair for Unnatural Amino Acid Mutagenesis in *E. coli.*" *Angewandte Chemie International Edition* 52.19 (2013): 5106-5109 each of which are hereby incorporated by reference in its entirety. As is known in the art, the synthetase catalyzes a reaction that attaches the nonstandard amino acid to the correct tRNA. The amino-acyl tRNA then migrates to the ribosome. The ribosome adds the nonstandard amino acid where the tRNA anticodon corresponds to the reverse complement of the codon on the mRNA of the target protein to be translated.

II. Removable Protecting Groups

According to one aspect, the target polypeptide includes a removable protecting group adjacent to the amino acid target location such that when the removable protecting group is removed, the amino acid target location is an N-end amino acid. Exemplary removable protecting groups are known to those of skill in the art and can be readily identified in the literature based on the present disclosure. According to one aspect, the removable protecting is a peptide sequence produced by the cell when making the target polypeptide. According to one aspect, the removable protecting is a peptide sequence produced by the cell when making the target polypeptide, such that the removable peptide and the target polypeptide is a fusion. According to this aspect, the cell is genetically modified to include a foreign nucleic acid sequence encoding the target polypeptide including a nonstandard amino acid substitution at an amino acid target location and a removable protecting group attached to the target polypeptide adjacent to the amino acid target location. According to one aspect, the removable protecting group is foreign to the cell, i.e. it is not endogenous to the cell. In this manner, the removable protecting is orthogonal to endogenous enzymes or other conditions within the cell.

An exemplary removable protecting group includes a cleavable protecting group, such as an enzyme cleavable protecting group. According to one aspect, the cell produces an enzyme that cleaves the removable protecting group to generate an N-end amino acid. An exemplary removable protecting group is a protein that is cleavable by a corresponding enzyme. According to one aspect, a removable protecting group is foreign to the cell and is not endogenous. According to one aspect, the enzyme that cleaves the removable protecting group is foreign to the cell and is not endogenous. According to one aspect, an exemplary removable protecting group for prokaryotic cells is ubiquitin that is cleavable by Ubp1. According to another aspect, an exemplary removable protecting group for eukaryotic cells is the sequence MENLYFQ/* (SEQ ID NO: 1), where "*" is the target position for the NSAA (known in the field as the P1' position), where "/" represents the cut site, and where "ENLYFQ/*" (SEQ ID NO: 2) is the sequence that is cleavable by certain variants of TEV protease. Ordinarily, TEV protease cleavage efficiency is influenced by the choice of the amino acid at the P1' position. However, mutants of TEV protease have been engineered which have increased or altered substrate tolerance at the P1' position (see Renicke, Christian, Roberta Spadaccini, and Christof Taxis. "A Tobacco Etch Virus Protease with Increased Substrate Tolerance at the P1' position." *PloS one* 8.6 (2013): e67915 hereby incorporated by reference in its entirety). The use of TEV protease in vivo in mammalian cells has been demonstrated and is described in Oberst, Andrew, et al. "Inducible dimerization and inducible cleavage reveal a requirement for both processes in caspase-8 activation." *Journal of Biological Chemistry* 285.22 (2010): 16632-16642 hereby incorporated by reference in its entirety. One of skill will readily understand based on the present disclosure that the methods described herein are useful in prokaryotic cells and eukaryotic cells.

According to the present disclosure, the N-end target residue is exposed using materials and methods that are or will become apparent to one of skill based on the present disclosure. An exemplary removable protecting protein domain includes a self-splicing domain, such as an intein, or other cleavable domains such as small ubiquitin modifiers (SUMO proteins). An exemplary removable protecting group may be a protein cleavage sequence along with its cognate partner, such as the TEV cleavage site and TEV protease. In general, any of the strategies used to remove N-terminal affinity tags in protein purification can serve as alternative ways to expose the N-end target residue. An exemplary system to expose the N-end target residue includes a class of enzymes known as methionine aminopeptidases which can remove the first N-terminal residue, such as when the second residue is the amino acid target location which is the desired site of addition of a NSAA. According to one aspect, the amino acid target location may be the N-terminal location or it may be any location between the N-terminal location and the C-terminal location. Accordingly, methods are provided for removing a protecting group and/or all amino acids up to the amino acid target location, thereby rendering the amino acid target location being the N-terminal amino acid.

III. Detectable Moiety

According to one aspect, the target polypeptide includes a detectable moiety attached to the C-end of the target polypeptide. Exemplary detectable moieties are known to those of skill in the art and can be readily identified in the literature based on the present disclosure. According to one aspect, the detectable moiety is a peptide sequence produced by the cell when making the target polypeptide. According to one aspect, the detectable moiety is a peptide sequence produced by the cell when making the target polypeptide, such that the detectable moiety and the target polypeptide is a fusion. According to this aspect, the cell is genetically modified to include a foreign nucleic acid sequence encoding the target polypeptide including a non-standard amino acid substitution at an amino acid target location and a detectable moiety attached to the target polypeptide, for example, at the C-end of the target polypeptide. According to one aspect, the detectable moiety is foreign to the cell, i.e. it is not endogenous to the cell.

An exemplary detectable moiety is a fluorescent moiety, such as GFP, that can be detected by fluorimetry, for example. An exemplary detectable moiety is a reporter protein. An exemplary detectable moiety includes a protein that confers antibiotic resistance which can be detected in the presence of an antibiotic. An exemplary detectable moiety includes an enzyme that performs a function (such as Beta-Galactosidase) that can lead to easy colorimetric output.

Aspects of the methods described herein may make use of epitope tags and reporter gene sequences as detectable moieties. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

IV. Genetic Modifications

Aspects of the present disclosure include the genetic modification of a cell to include foreign genetic material which can then be expressed by the cell. The cell may be modified to include any other genetic material or elements useful in the expression of a nucleic acid sequence. Foreign genetic elements may be introduced or provided to a cell using methods known to those of skill in the art. For example, the cell may be genetically modified to include a foreign nucleic acid sequence encoding the target polypeptide including a non-standard amino acid substitution at an amino acid target location, a removable protecting group attached to the target polypeptide adjacent to the amino acid target location and a detectable moiety attached to the C-end of the target polypeptide. The nonstandard amino acid may be encoded by a corresponding nonsense or sense codon. The cell may be genomically recoded to recognize an engineered amino-acyl tRNA synthetase corresponding or cognate to a non-standard amino acid. The cell may be genetically modified to include a foreign nucleic acid sequence encoding an amino-acyl tRNA synthetase and/or a transfer RNA corresponding or cognate to the nonstandard amino acid and wherein the nonstandard amino acid is provided to the cell and the cell expresses the synthetase and the transfer RNA to include the nonstandard amino acid at the amino acid target location. The cell is genetically modified to include a foreign nucleic acid sequence encoding an enzyme for cleaving the removable protecting group under influence of an inducible promoter. The cell is genetically modified to include an inducible promoter influencing the production of an enzyme system for removal of the removable protecting group. The enzyme system or component thereof may be under influence of the inducible promoter. For example, the adapter which helps associate the cleavage enzyme with the removable protecting group may be under influence of an inducible promoter.

In general, nucleic acids may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Aspects of the methods described herein may make use of vectors. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Aspects of the methods described herein may make use of regulatory elements. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). Regulatory elements useful in eukaryotic cells include a tissue-specific promoter that may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). Common prokaryotic promoters include IPTG (isopropyl B-D-1-thiogalactopyranoside) inducible, anhydrotetracycline inducible, or arabinose inducible promoters. Such promoters express genes only in the presence of IPTG, anhydrotetracycline, or arabinose in the medium. An exemplary promoter for use in bacteria such as *E. coli* to express aminoacyl tRNA synthetase is an arabinose inducible promoter. An exemplary promoter for use in bacteria such as *E. coli* to express a reporter protein is an anhydrotetracycline inducible promoter.

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

V. Adapter Protein Protease Systems

According to one aspect, the cell includes a protease system for degrading the target polypeptide when the N-end amino acid is a standard amino acid. The protease system may be endogenous or exogenous. The cell may include an adapter or discriminator protein that coordinates with a protease for degrading the target polypeptide when the N-end amino acid is a standard amino acid. The adapter protein may be under influence of an inducible promoter. According to one aspect, the adapter protein is ClpS or a variant or mutant thereof. According to one aspect, adapter proteins may have different levels of selectivity for certain amino acids. According to certain aspects, adapter proteins, such as ClpS may be altered to improve selectivity, such as between standard amino acids and non-standard amino acids or between a desired NSAA and an undesired NSAA. According to one aspect, the protease system is a ClpS-ClpAP protease system.

According to one aspect, protease systems include Clps or homologs or mutants thereof, such as ClpS_V65I, ClpS_V643I, or ClpS_L32F. The N-end rule is mediated by homologs of ClpS/ClpAP in bacteria. In eukaryotes, the N-end rule involves more distant homologs of ClpS (UBR1, ubiquitin E3 ligases) and degradation by the proteasome. Accordingly, the present disclosure contemplates use of many of the bacterial ClpS homologs to perform similar functions with slightly different amino acid recognition specificity. The present disclosure also contemplates use of eukaryotic protease systems, such as UBR1 and related variants to mediate N-end rule recognition with different amino acid recognition specificity in eukaryotes.

VI. Cells

According to certain aspects, cells according to the present disclosure include prokaryotic cells and eukaryotic cells. Exemplary prokaryotic cells include bacteria. Microorganisms which may serve as host cells and which may be genetically modified to produce recombinant microorganisms as described herein may include one or members of the genera *Clostridium, Escherichia, Rhodococcus, Pseudomonas, Bacillus, Lactobacillus Saccharomyces*, and *Enterococcus*. Particularly suitable microorganisms include bacteria and archaea. Exemplary microorganisms include *Escherichia coli, Bacillus subtilis*, and *Saccharomyces cerevisiae*. Exemplary eukaryotic cells include animal cells, such as human cells, plant cells, fungal cells and the like.

In addition to *E. coli*, other useful bacteria include but are not limited to *Bacillus subtilis, Bacillus megaterium, Bifidobacterium bifidum, Caulobacter crescentus, Clostridium difficile, Chlamydia trachomatis, Corynebacterium glutamicum, Lactobacillus acidophilus, Lactococcus lactis, Mycoplasma genitalium, Neisseria gonorrhoeae, Prochlorococcus marinus, Pseudomonas aeruginosa, Psuedomonas putida, Treponema pallidum, Streptomyces coelicolor, Synechococcus elongates, Vibrio natrigiens*, and *Zymomonas mobilis*.

Exemplary genus and species of bacteria cells include *Acetobacter aurantius, Acinetobacter bitumen, Actinomyces israelii, Agrobacterium radiobacter, Agrobacterium tumefaciens, Anaplasma Anaplasma phagocytophilum, Azorhizobium caulinodans, Azotobacter vinelandii, viridans streptococci, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides, Bacteroides fragilis, Bacteroides gingivalis, Bacteroides melaninogenicus* (also referred to as *Prevotella melaninogenica*), *Bartonella, Bartonella henselae, Bartonella quintana, Bordetella, Bordetella bronchiseptica, Bordetella pertussis, Borrelia burgdorferi, Brucella abortus, Brucella melitensis, Brucella suis, Burkholderia, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydia, Chlamydia trachomatis, Chlamydophila Chlamydophila pneumoniae* (also known as *Chlamydia pneumoniae*) *Chlamydophila psittaci* (also known as *Chlamydia psittaci*), *Clostridium, Clostridium botulinum, Clostridium difficile, Clostridium perfringens* (also known as *Clostridium welchii*), *Clostridium tetani, Corynebacterium, Corynebacterium diphtheriae, Corynebacterium fusiforme, Coxiella burnetii, Ehrlichia chaffeensis, Enterobacter cloacae, Enterococcus, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma, Mycoplasma fermentans, Mycoplasma genitalium, Mycoplasma hominis, Mycoplasma penetrans, Mycoplasma pneumoniae, Neisseria, Neisseria gonorrhoeae, Neisseria meningitidis, Pasteurella, Pasteurella multocida, Pasteurella tularensis, Peptostreptococcus, Porphyromonas gingivalis, Prevotella melaninogenica* (also known as *Bacteroides melaninogenicus*), *Pseudomonas aeruginosa, Rhizobium radiobacter, Rickettsia, Rickettsia prowazekii, Rickettsia psittaci, Rickettsia quintana, Rickettsia rickettsii, Rickettsia trachomae, Rochalimaea, Rochalimaea henselae, Rochalimaea quintana, Rothia dentocariosa, Salmonella, Salmonella enteritidis, Salmonella typhi, Salmonella typhimurium, Serratia marcescens, Shigella dysenteriae, Staphylococcus, Staphylococcus aureus, Staphylococcus epidermidis, Stenotrophomonas maltophilia, Streptococcus Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema, Treponema pallidum, Treponema denticola, Vibrio, Vibrio cholerae, Vibrio comma, Vibrio parahaemolyticus, Vibrio vulnificus, Wolbachia, Yersinia, Yersinia enterocolitica, Yersinia pestis*, and *Yersinia pseudotuberculosis*, and other genus and species known to those of skill in the art.

Exemplary genus and species of yeast cells include *Saccharomyces, Saccharomyces cerevisiae, Torula, Saccharomyces boulardii, Schizosaccharomyces, Schizosaccharomyces pombe, Candida, Candida glabrata, Candida tropicalis, Yarrowia, Candida parapsilosis, Candida krusei, Saccharomyces pastorianus, Brettanomyces, Brettanomyces bruxellensis, Pichia, Pichia guilliermondii, Cryptococcus, Cryptococcus gattii, Torulaspora, Torulaspora delbrueckii, Zygosaccharomyces, Zygosaccharomyces bailii, Candida lusitaniae, Candida stellata, Geotrichum, Geotrichum candidum, Pichia pastoris, Kluyveromyces, Kluyveromyces marxianus, Candida dubliniensis, Kluyveromyces, Kluyveromyces lactis, Trichosporon, Trichosporon uvarum, Eremothecium, Eremothecium gossypii, Pichia stipitis, Candida milleri, Ogataea, Ogataea polymorpha, Candida oleophilia, Zygosaccharomyces rouxii, Candida albicans, Leucosporidium, Leucosporidium frigidum, Candida viswanathii, Candida blankii, Saccharaomyces telluris, Saccharomyces florentinus, Sporidiobolus, Sporidiobolus salmonicolor, Dekkera, Dekkera anomala, Lachancea, Lachancea kluyveri, Trichosporon, Trichosporon mycotoxinivorans, Rhodotorula, Rhodotorula rubra, Saccharomyces exiguus, Sporobolomyces koalae*, and *Trichosporon cutaneum*, and other genus and species known to those of skill in the art.

Exemplary genus and species of fungal cells include Sac fungi, Basidiomycota, Zygomycota, Chtridiomycota, Basidiomycetes, Hyphomycetes, Glomeromycota, Microsporidia, Blastocladiomycota, and Neocallimastigomycota, and other genus and species known to those of skill in the art.

Exemplary eukaryotic cells include mammalian cells, plant cells, yeast cells and fungal cells.

VII. Standard Amino Acid

As used herein, the term "SAA" (standard amino acid) include one of the L-amino acids that typically naturally occur in proteins on Earth and includes alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline and valine. The standard amino acids that are naturally N-end destabilizing in most bacteria include tyrosine, phenylalanine, tryptophan, leucine, lysine, and arginine. According to one aspect, the amino acid at the amino acid target location is an NSAA that is stabilizing. When the natural analog of the NSAA is destabilizing and is present at the amino acid target location, degradation of the polypeptide occurs. Standard amino acids that are not naturally destabilizing via the N-end rule using natural ClpS, can be destabilizing when the ClpS is engineered to recognize such standard amino acid.

The N-end rule in bacteria may also be engineered to recognize isoleucine, valine, aspartate, glutamate, asparagine, and glutamine as destabilizing using methods known to those of skill in the art which is useful when the desired NSAA is an analog of these amino acids. For example, isoleucine and valine can be converted into N-end destabilizing residues by introducing a ClpS variant (M40A) that recognizes these amino acids as N-terminal destabilizing residues see (Román-Hernández G, Grant R A, Sauer R T, & Baker T A (2009) Molecular basis of substrate selection by the N-end rule adaptor protein ClpS. Proceedings of the National Academy of Sciences 106(22):8888-8893 hereby incorporated by reference in its entirety). In fact, we observe that by merely overexpressing ClpS, isoleucine and valine appear as N-end destabilizing residues (FIG. 3F). Aspartate and glumatate may be converted into N-end destabilizing residues by introducing a bacterial aminoacyl-transferase from *Vibrio vulnificus* (Bpt) that is a homolog of eukaryotic transferases and N-terminally appends a leucine (L) to peptides containing N-terminally exposed aspartate or glutamate (see Graciet E, et al. (2006) Aminoacyl-transferases and the N-end rule pathway of prokaryotic/eukaryotic specificity in a human pathogen. Proceedings of the National Academy of Sciences of the United States of America 103(9):3078-3083 hereby incorporated by reference in its entirety). The ability of Bpt to catalyze this reaction has been demonstrated in *E. coli* and shows that components of the N-end rule, which includes many more conditionally destabilizing residues in eukaryotes, can be transferred across kingdoms. Asparagine and glutamine can be converted into N-end destabilizing residues by using an N-terminal amidase from *S. cerevisiae* (NTA1), which converts N-terminal asparagine into aspartate or N-terminal glutamine into glumate, respectively (see Tasaki T, Sriram S M, Park K S, & Kwon Y T (2012) The N-End Rule Pathway. Annual Review of Biochemistry 81(1):261-289 hereby incorporated by reference in its entirety). Indeed, in many eukaryotic cells these amino acids and more are naturally conditionally N-end destabilizing. One of skill will understand that an N-end rule destabilizing pathway may be provided for all 20 standard amino acids as a basis for a system where a desired amino acid from among the 20 standard amino acids is N-end destabilizing in at least one context (see Chen, Shun-Jia, et al. "An N-end rule pathway that recognizes proline and destroys gluconeogenic enzymes." *Science* 355.6323 (2017): eaal3655 hereby incorporated by reference in its entirety). One of skill in the art can identify the eukaryotic proteins required for conferring expanded N-end destabilization and transfer them to prokaryotes as needed. Similarly, in eukaryotic cells one can constitutively express components required for conferring expanded N-end destabilization such that degradation of proteins containing N-end standard amino acids no longer remains conditional. One of skill will recognize that some amino acids rendered destabilizing may have adverse consequences for cell physiology. For example, most native proteins begin with methionine and if methionine is made N-end destabilizing then most proteins would degrade. Aspects of converting an N-end stabilizing amino acid to an N-end destabilizing amino acid can be tested in a particular organism.

VIII. Non-Standard Amino Acid

As used herein, the term "NSAA" refers to an unmodified amino acid that is not one of the 20 naturally occurring standard L-amino acids. NSAAs also include synthetic amino acids which have been designed to include a non-standard functional group not present in the standard amino acids or are naturally occurring amino acids bearing functional groups not present in the set of standard amino acids. Accordingly, a non-standard amino acid may include the structure of a standard amino acid and which includes a non-standard functional group. A non-standard amino acid may include the basic amino acid portion of a standard amino acid and include a non-standard functional group.

NSAAs also refer to natural amino acids that are not used by all organisms (e.g. L-pyrrolysine (B. Hao et al., A new uag-encoded residue in the structure of a methanogen methyltransferase. *Science*. 296:1462) and L-selenocysteine (S. Osawa et al., Recent evidence for evolution of the genetic code. *Microbiol. Mol. Biol. Rev.* 56:229)). NSAAs are also known in the art as unnatural amino acids (UAAs) and non-canonical amino acids (NCAAs).

NSAAs include, but are not limited to, p-Acetylphenylalanine, m-Acetylphenylalanine, O-allyltyrosine, Phenylselenocysteine, p-Propargyloxyphenylalanine, p-Azidophenylalanine, p-Boronophenylalanine, O-methyltyrosine, p-Aminophenylalanine, p-Cyanophenylalanine, m-Cyanophenylalanine, p-Fluorophenylalanine, p-Iodophenylalanine, p-Bromophenylalanine, p-Nitrophenylalanine, L-DOPA, 3-Aminotyrosine, 3-Iodotyrosine, p-Isopropylphenylalanine, 3-(2-Naphthyl)alanine, biphenylalanine, homoglutamine, D-tyrosine, p-Hydroxyphenyllactic acid, 2-Aminocaprylic acid, bipyridylalanine, HQ-alanine, p-Benzoylphenylalanine, o-Nitrobenzylcysteine, o-Nitrobenzylserine, 4,5-Dimethoxy-2-Nitrobenzylserine, o-Nitrobenzyllysine, o-Nitrobenzyltyrosine, 2-Nitrophenylalanine, dansylalanine, p-Carboxymethylphenylalanine, 3-Nitrotyrosine, sulfotyrosine, acetyllysine, methylhistidine, 2-Aminononanoic acid, 2-Aminodecanoic acid, pyrrolysine, Cbz-lysine, Boc-lysine, allyloxycarbonyllysine, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5,-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, -phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid, and the like. NSAAs also include amino acids that are functionalized, e.g., alkyne-functionalized, azide-functionalized, ketone-functionalized, aminooxy-functionalized and the like. For reviews of NSAAs and lists of NSAAs suitable for use in certain embodiments of the subject invention, see Liu and Schultz (2010) *Ann. Rev. Biochem.* 79:413, and Kim et al. (2013) *Curr. Opin. Chem. Biol.* 17:412, each of which is incorporated herein by reference in its entirety for all purposes.

In certain aspects, an NSAA of the subject invention has a corresponding aminoacyl tRNA synthetase (aaRS)/tRNA pair. In certain aspects, the aminoacyl tRNA synthetase/tRNA pair is orthogonal to those in a genetically modified organism such as, e.g., a prokaryotic cell, a bacterium (e.g., *E. coli*), a eukaryotic cell, a yeast, a plant cell, an insect cell, a mammalian cell, a virus, etc. In certain aspects, an NSAA of the subject invention is non-toxic when expressed in a genetically modified organism such as, e.g., a prokaryotic cell, a bacterium (e.g., *E. coli*), a eukaryotic cell, a yeast, a plant cell, an insect cell, a mammalian cell, a virus, etc. In certain aspects, an NSAA of the subject invention is not or does not resemble a natural product present in a cell or organism. In certain aspects, an NSAA of the subject invention is hydrophobic, hydrophilic, polar, positively charged, or negatively charged. In other aspects, an NSAA of the subject invention is commercially available (such as, e.g., L-4,4-bipnehylalanine (bipA) and L-2-Naphthylalanine (napA)) or synthesized according to published protocols.

EXAMPLE I

Exemplary Degradation Materials and Methods

According to one aspect, the disclosure provides a method of making a protein having a non-standard amino acid incorporated therein, such as at its N-terminus, in a cell. The cell is provided with a nucleic acid sequence encoding a ubiquitin fused to the N-terminus of the protein wherein the N-terminus of the protein is an amino acid target location intended to have a nonstandard amino acid. The nonstandard amino acid may be encoded by a nonsense or sense codon. The cell is provided with a ubiquitin cleavase. The cell may include an endogenous protease system, such as a ClpS-ClpAP system. The cell is provided with a non-standard amino acid. The cell expresses the fusion protein having either a standard or a non-standard amino acid incorporated at the amino acid target location. The ubiquitin cleavase cleaves the ubiquitin to produce a protein having either the standard or non-standard intervening amino acid at its N-terminus. If a standard amino acid is present at the N-terminus, the ClpS recognizes the standard amino acid at the N-terminus and targets the protein having the standard amino acid at its N-terminus to ClpP for degradation. If a nonstandard amino acid is present at the N-terminus, the Clps does not recognize the nonstandard amino acid and the protein is not targeted for degradation. A residue is destabilizing if it is recognized by the ClpS adaptor protein, which is the discriminator of the N-end rule in *E. coli* such as is described in Erbse A, et al. (2006) ClpS is an essential component of the N-end rule pathway in *Escherichia coli*. *Nature* 439(7077):753-756 and Wang K H, Oakes E S C, Sauer R T, & Baker T A (2008) Tuning the Strength of a Bacterial N-end Rule Degradation Signal. *Journal of Biological Chemistry* 283(36):24600-24607; Schmidt R, Zahn R, Bukau B, & Mogk A (2009) ClpS is the recognition component for *Escherichia coli* substrates of the N-end rule degradation pathway. *Molecular Microbiology* 72(2):506-517.; Román-Hernández G, Grant R A, Sauer R T, & Baker T A (2009) Molecular basis of substrate selection by the N-end rule adaptor protein ClpS. *Proceedings of the National Academy of Sciences* 106(22):8888-8893; Schuenemann V J, et al. (2009) Structural basis of N-end rule substrate recognition in *Escherichia coli* by the ClpAP adaptor protein ClpS. *EMBO reports* 10(5):508-514; Román-Hernández G, Hou Jennifer Y, Grant Robert A, Sauer Robert T, & Baker Tania A (2011) The ClpS Adaptor Mediates Staged Delivery of N-End Rule Substrates to the AAA+ ClpAP Protease. *Molecular Cell* 43(2):217-228; and Hou J Y, Sauer R T, & Baker T A (2008) Distinct structural elements of the adaptor ClpS are required for regulating degradation by ClpAP. *Nat Struct Mol Biol* 15(3):288-294 each of which is hereby incorporated by reference in its entirety.

According to another aspect, the disclosure provides a method of screening for an amino acyl tRNA synthetase variant that preferentially selects a non-standard amino acid against its standard amino acid counterpart for incorporation into a protein in a cell. The cell is provided with an amino acyl tRNA synthetase variant. As shown in FIGS. 1A and 1B, the cell is provided with a nucleic acid sequence encoding a ubiquitin fused to the N-terminus of the protein wherein the N-terminus of the protein is an amino acid target location intended to have a nonstandard amino acid, and wherein GFP is fused to the C-end of the protein. The nonstandard amino acid may be encoded by a nonsense or sense codon. The cell is provided with a ubiquitin cleavase, such as Ubp1. The cell may include an endogenous protease system, such as a ClpS-ClpAP system. The cell is provided with a non-standard amino acid. The cell expresses the fusion protein having either a standard or a non-standard amino acid incorporated at the amino acid target location. The ubiquitin cleavase cleaves the ubiquitin to produce a protein having either the standard or non-standard intervening amino acid at its N-terminus. If a standard amino acid is present at the N-terminus, the ClpS recognizes the standard amino acid at the N-terminus and targets the protein having the standard amino acid at its N-terminus to ClpP for degradation, including the GFP portion. If a nonstandard amino acid is present at the N-terminus, the Clps does not recognize the nonstandard amino acid and the protein is not targeted for degradation. The GFP is detected and is indicative of the presence of a synthetase variant that preferentially selects the non-standard amino acid against its standard amino acid counterpart for incorporation into the protein.

According to another aspect, the strength of the signal detected from the GFP is indicative of the amount of protein produced that included the nonstandard amino acid. In this manner, methods are provided for screening and evolving an amino acyl tRNA synthetase variant that preferentially selects a non-standard amino acid against its standard amino acid counterpart for incorporation into a protein in a cell.

EXAMPLE II

A Method of Making a Protein Having a Non-Standard Amino Acid Incorporated at its N-Terminus in an Engineered *E. coli* Having Orthogonal Translation Systems by Engineering Post-Translational Proofreading to Discriminate Non-Standard Amino Acids Advancements to genetic code expansion require accurate, selective, and high-throughput determination of non-standard amino acid (NSAA) incorporation into proteins. This example sets forth embodiments for engineering synthetic quality control for detection of NSAA incorporation with minimal incidence of false positives due to common misincorporation of related standard amino acids or undesired NSAAs. Post-Translational Proofreading (PTP) was achieved by targeting desired NSAAs for incorporation at a site subsequently exposed as the N-terminus of a reporter protein, which is stabilized by correct incorporation or destabilized by misincorporation. It has been shown that PTP is modular, generalizable, and highly tunable by engineering the N-end rule pathway of protein degradation to discriminate incorporation of different NSAAs from one another. Embodiments in this example illustrate PTP utility during evolution of the biphenylalanine orthogonal translation system (OTS) used for biocontainment. The more selective OTS confers lower escape frequencies and greater fitness to all three tested strains. This work presents a new paradigm for molecular recognition of competitive amino acids in target proteins.

The fidelity of translation relies on the selectivity of amino acyl transfer RNA (tRNA) synthetases (AARSs), which catalyze esterification of tRNAs to their corresponding amino acids (1). Orthogonal AARS/tRNA pairs, together known as OTSs, enable site-specific NSAA incorporation into proteins, most often by suppressing amber (UAG) stop codons in targeted sequences (2, 3). Four primary site-specific OTS families have been developed for NSAA incorporation: *Methanococcus jannaschii* tyrosyl-tRNA synthetase (MjTyrRS)/tRNA$_{CUA}^{Tyr}$; various *Methanosarcina* pyrrolysyl-tRNA synthetase (PylRS)/tRNA$_{CUA}^{Pyl}$; *Escherichia coli* tyrosyl-tRNA synthetase (EcTyrRS)/tRNA$_{CUA}^{Tyr}$; and *E. coli* leucyl-tRNA synthetase (EcLeuRS)/tRNA$_{CUA}^{Leu}$ (4, 5). Another commonly used OTS is the *Saccharomyces cerevisiae* tryptophanyl-tRNA synthetase (ScTrpRS)/tRNA$_{CUA}^{Trp}$ pair (6-8) (FIG. 1A).

However, engineered OTS promiscuity for standard amino acids (SAAs) and for undesired NSAAs is a major barrier to expansion of the genetic code. The low fidelity of several OTSs is documented, revealing that even after multiple rounds of negative selection they misacylate tRNA with SAAs that their ancestral variants acted upon, such as tyrosine (Y) and tryptophan (W) (9-13). The problem of OTS cross-talk with SAAs is exemplified in the case of biocontainment, which was previously demonstrated based on the NSAA biphenylalanine (BipA) and its corresponding OTS (14) (FIG. 1B). Protease mutations were found in sequenced escapees that emerged in the absence of BipA, suggesting that redesigned enzymes intended to be destabilized by SAA misincorporation may transiently remain functional prior to degradation (15). Furthermore, genomic integration of the BipA OTS, which likely decreased misincorporation, reduced escape frequency. Given that OTS evolution efforts have not selected against activity upon undesired NSAAs, greater promiscuity is expected in the presence of multiple NSAAs. OTS promiscuity is of particular concern when using members of TyrRS/TrpRS/PylRS families together given demonstrated overlap of substrate ranges (16-18). Together, these concerns converge as we progress towards constructing a 57-codon *E. coli* strain anticipated to exhibit multi-virus resistance, to require biocontainment, and to serve as a platform for producing proteins containing multiple different NSAAs (19). Many other applications utilizing NSAAs, such as protein double labelling, FRET, and antibody conjugation, also require high fidelity incorporation to avoid heterogenous protein production.

Figure 1C:
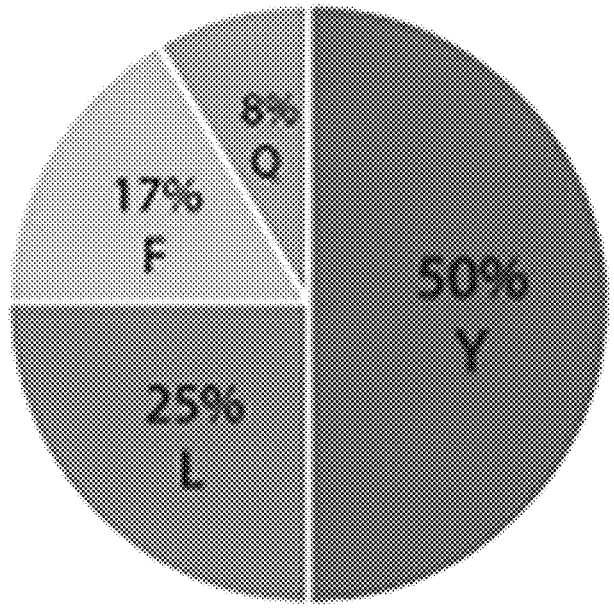
Figure 4:
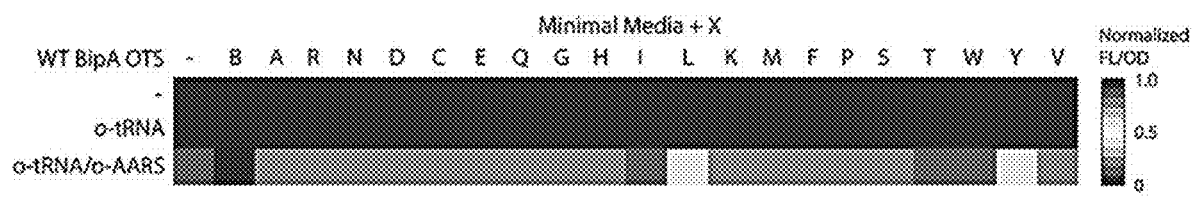
FIG. 4 shows screening of BipA OTS promiscuity against SAAs using spiking experiments in minimal media and a plasmid-based Ub-GFP_1UAG reporter.

Currently, the identity of incorporated amino acid can only be determined in low-throughput via protein purification and mass spectrometry. This approach was used initially to determine the identity of SAAs incorporated by the BipA OTS in the absence of BipA (90%+Y/L/F observed, with Q also present due to known OTS-independent near-cognate suppression (20, 21)) (FIG. 1C). SAA spiking experiments were also performed in minimal media and found that these too suggested Y and L incorporation (FIG. 4). To dramatically accelerate OTS engineering efforts, a system was sought to be developed with the following design criteria: (i) the ability to controllably mask and unmask misincorporation for a single reporter in vivo; (ii) compatibility with different reporter proteins; (iii) customizability for most commonly used NSAAs. Embodiments of the disclosure relates to the development of "Post-Translational Proofreading" (PTP) to discriminate NSAA incorporation in vivo. The N-end rule of protein degradation, a natural protein regulatory and quality control pathway conserved across prokaryotes and eukaryotes (22-24), was repurposed and altered for synthetic substrates. In *E. coli*, N-end destabilizing residues (Y/F/W/L/K/R) result in protein half-lives on the timescale of minutes (23). It was observed that all SAAs corresponding to commonly used NSAAs are reportedly N-end destabilizing. The ability to optionally degrade proteins containing misincorporation events is expected to dramatically facilitate OTS directed evolution because positive screens with degradation can lower incidence of false positive misincorporation events and negative screens without degradation can screen against unmasked misincorporation.

Figure 1D:
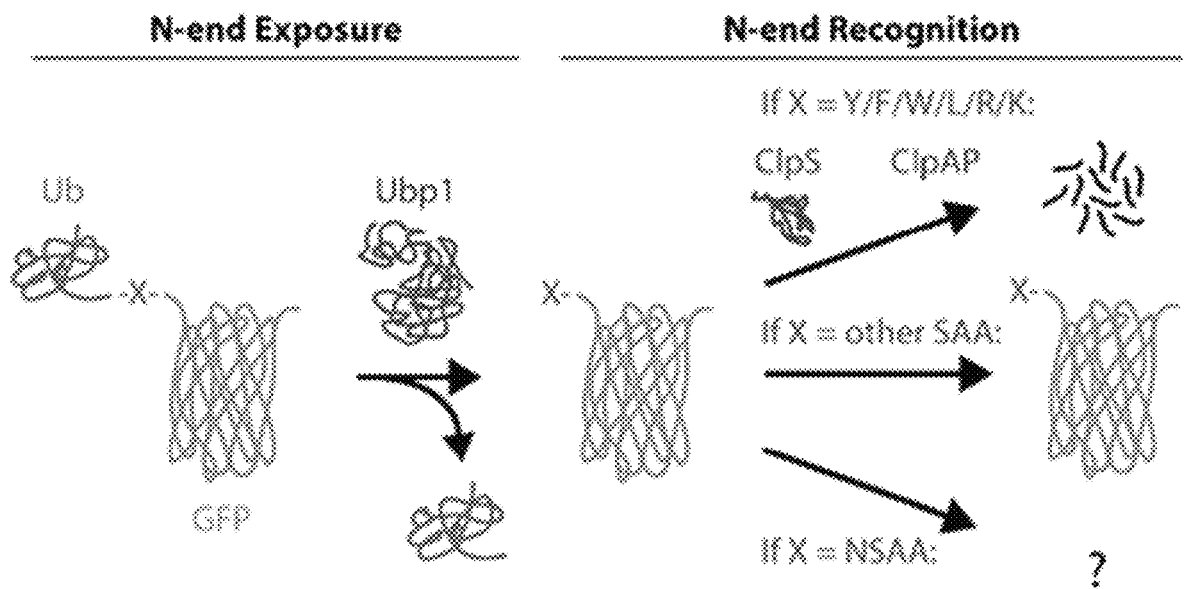

To begin, a reporter consisting of a cleavable ubiquitin domain (Ub) followed by one UAG codon, a conditionally strong N-degron (25, 26), and a super-folder green fluorescent protein (sfGFP) with a C-terminal His6x-tag (SEQ ID NO: 3) was genomically integrated into a recoded *E. coli* strain devoid of UAG codons and associated release factor (C321.ΔA) (27), resulting in strain C321.Ub-UAG-sfGFP (FIG. 1D). The use of only one UAG codon increases assay sensitivity for promiscuity compared to the use of multi-UAG codon reporters (28), and genomic integration of the reporter increases reproducibility by eliminating plasmid copy number effects (29). Plasmids were used to express different combinations of the orthogonal tRNA$_{CUA}^{Tyr}$, the BipARS, and an N-terminally truncated yeast Ub cleavase protein (UBP1) (30, 31). Overexpression of N-end rule pathway components already present in C321.ΔA: clpS and clpP were also tested. ClpS is the adaptor protein that binds peptides containing primary N-end substrates (Y/F/W/L) and delivers them to the ClpAP AAA+ protease complex for unfolding and degradation (32).

Figure 1E:
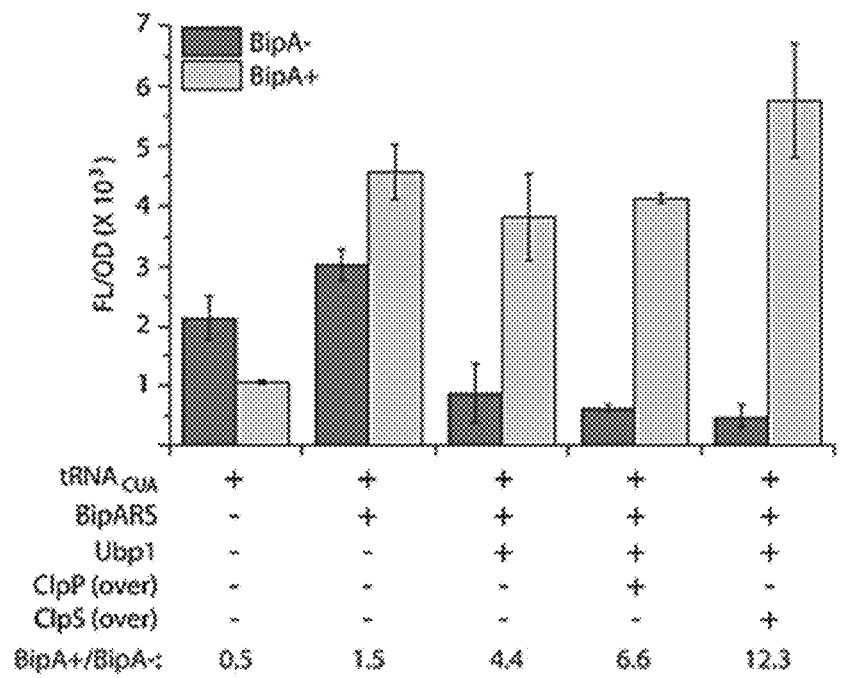
Figure 1F:
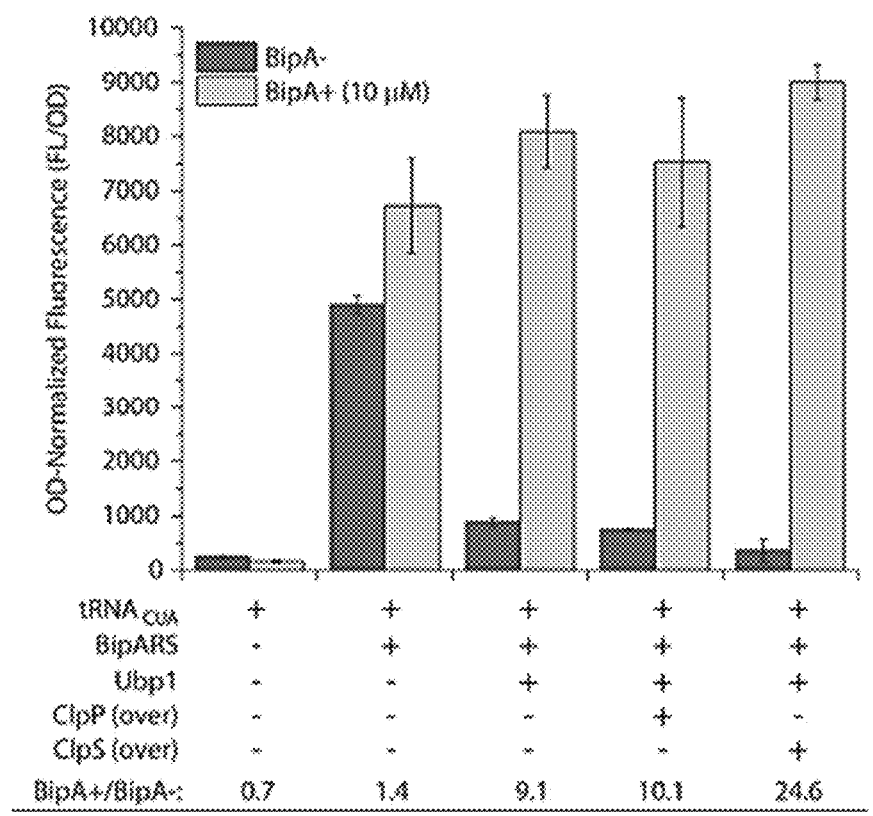

In vivo GFP fluorescence normalized to optical density (FL/OD) was measured to approximate the amount of synthesized reporter protein containing NSAA per cell for these strains. Experiments with and without BipA (BipA+ or BipA−) revealed that expression of the orthogonal tRNA alone was responsible for a moderate amount of FL/OD, but that together expression of the BipARS/tRNA pair resulted in BipA− FL/OD nearly as high as BipA+ FL/OD (FIGS. 1E-1F). Encouragingly, it was observed significant reduction of the BipA− FL/OD upon UBP1 expression, which is required for N-end exposure of the target residue. The decrease in only BipA− FL/OD supported our hypothesis that BipA would be N-end stabilizing. BipA− FL/OD further decreased upon overexpression of ClpS, suggesting that the rate of N-end discrimination was previously limiting.

Figure 5A:
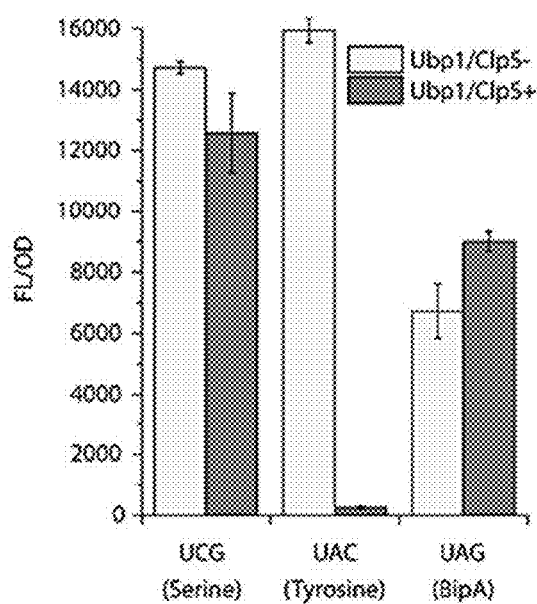
FIGS. 5A-5B show additional initial characterization of Post-Translational Proofreading (PTP) system.
Figure 5B:
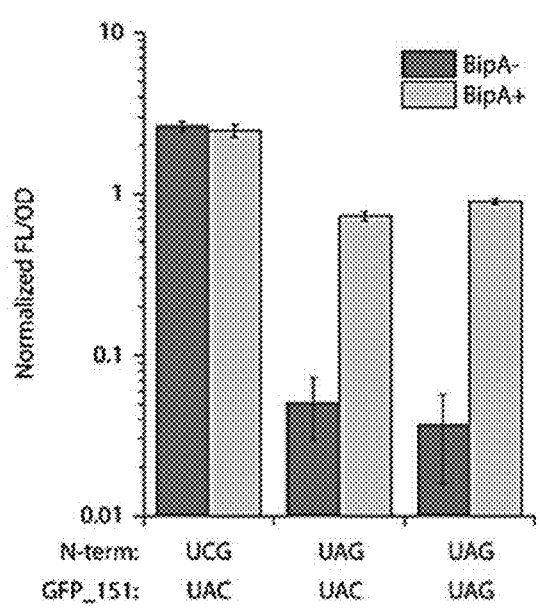
Figure 6A:
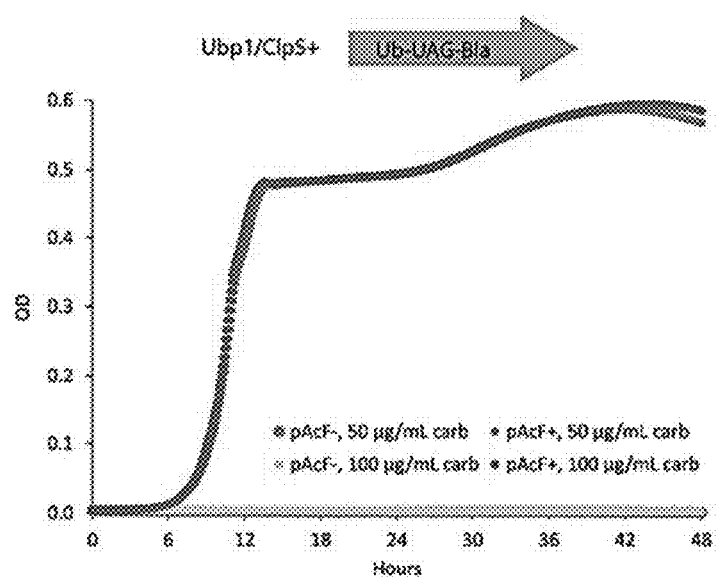
FIGS. 6A-6B show that PTP is generalizable to other reporter proteins.
Figure 6B:
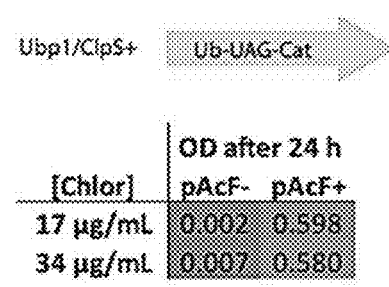

Through the addition of another UAG codon internal to the GFP, it is verified that BipA incorporation at any position does not confer a stabilizing effect and that the N-end rule is behaving as expected upon substitution of the N-end UAG to UGG (serine, stabilizing) or UAC (tyrosine, destabilizing) (FIG. 5A). Additionally, it was demonstrated that the use of one N-terminal UAG in the reporter does not lead to significantly different results from the use of two UAGs (FIG. 5B). By replacing the sfGFP reporter with selectable markers that provide resistance to carbenicillin or chloramphenicol, it was verified that PTP can be easily extended to other target proteins (FIGS. 6A-6B).

Figure 2A:
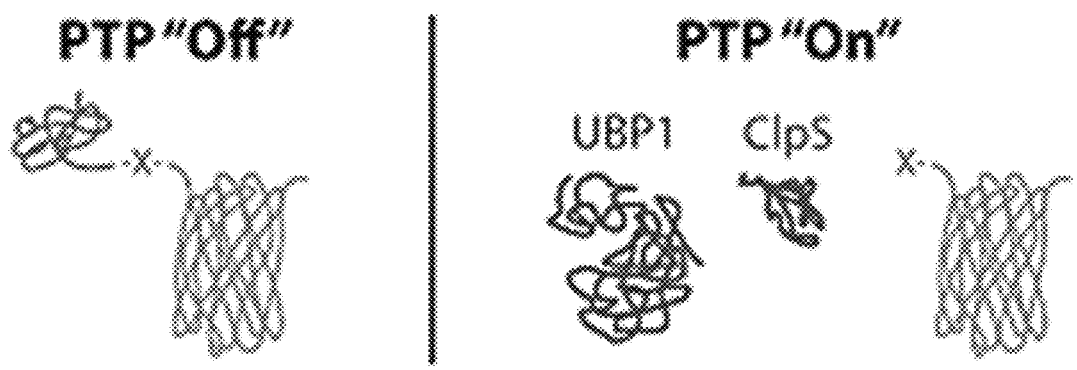
FIGS. 2A to 2C shows broad evaluation of OTS promiscuity for NSAA and SAAs with PTP "Off" and "On".
Figure 2B:
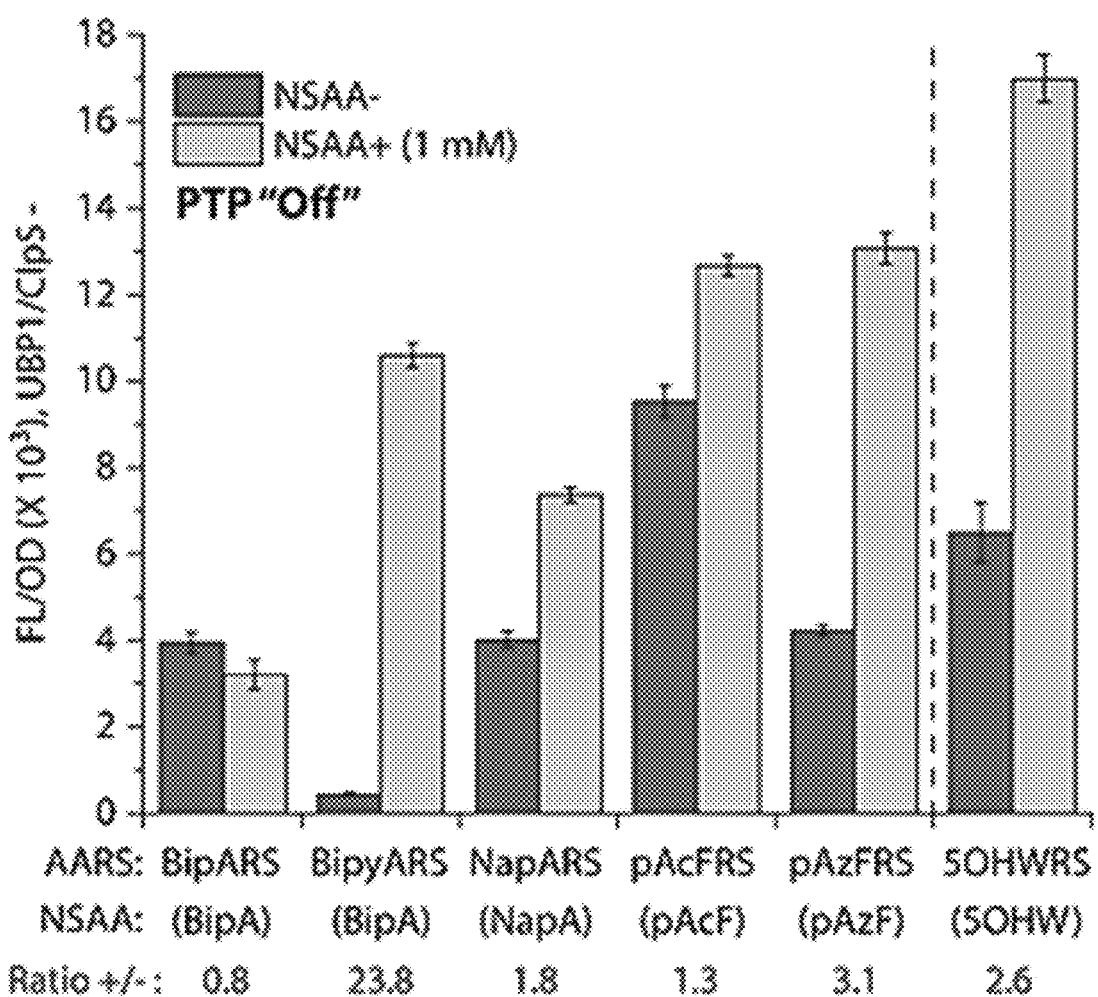
Figure 2C:
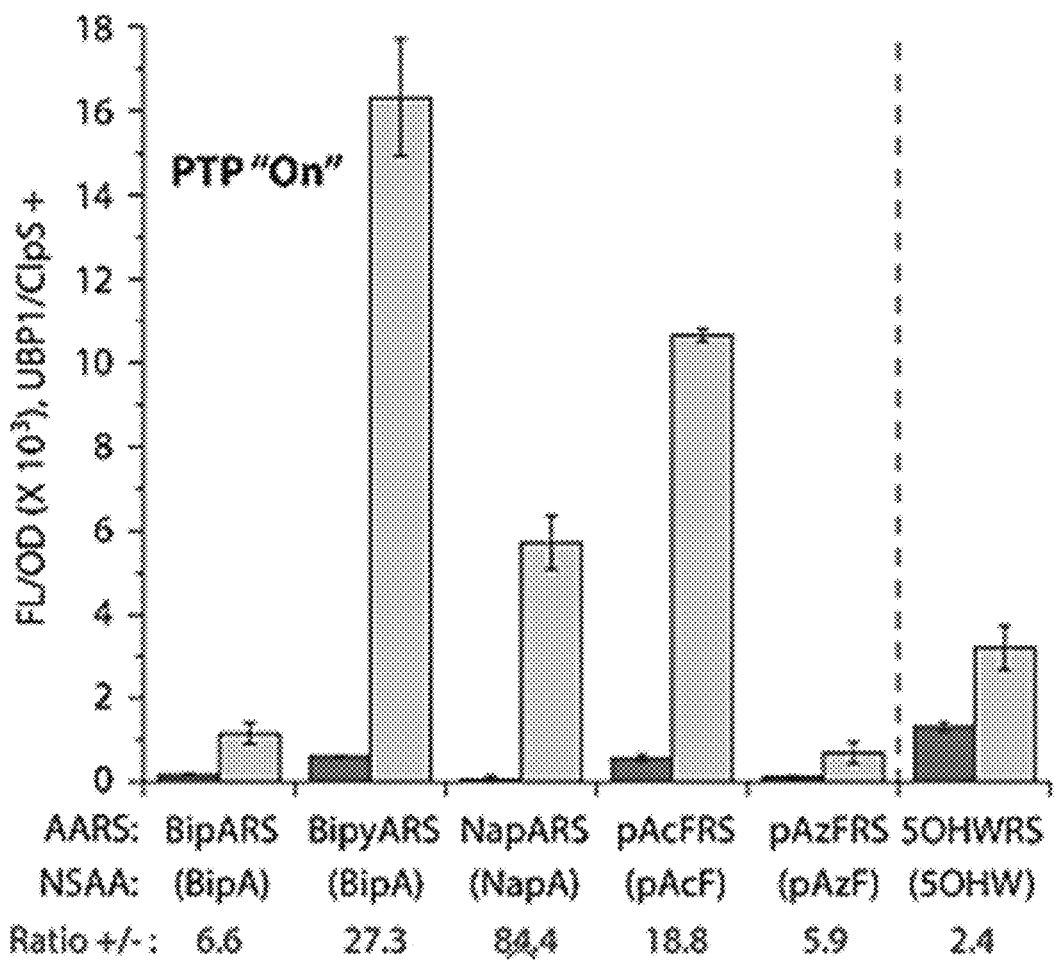

It was next sought to characterize the promiscuity of the BipA OTS and several other MjTyrRS-derived OTSs for different NSAAs (FIG. 1B) and subsequently for SAAs. To examine OTS promiscuity for SAAs, the Ub-UAG-GFP reporter strain was used to implement an optional PTP "Off" or "On" approach with co-expression of UBP1 and ClpS to provide insight about relative levels of SAA/NSAA incorporation in the absence or presence of NSAA (NSAA− or NSAA+) (FIG. 2A). The native ClpS and the ClpP protease were overexpressed to determine their effect on the kinetics of GFP reporter degradation. The abundance of the GFP was measured as green fluorescence normalized by optical density (FL/OD) using a standard plate reader for fluorimetric and spectrophotometric assays. Two different families of OTSs (MjTyrRS and ScTrpRS) without PTP were examined (FIG. 2B). Every OTS except for BipyARS/tRNA$_{CUA}^{Tyr}$ exhibited high NSAA− FL/OD. Confirming the generality of our PTP approach, significant decrease of NSAA− FL/OD for all OTSs with PTP "On" was observed (FIG. 2C). However, significant decrease of NSAA+FL/OD for two NSAAs: p-Azido-phenylalanine (pAzF) and 5-Hydroxy-tryptophan (5OHW) was also observed. Since ClpS is endogenous to E. coli, it need not be overexpressed. However, overexpression, such as by use of an inducible promoter, increases the concentration of ClpS and therefore the ability of ClpS to discriminate between desired nonstandard amino acids and undesired standard amino acids or undesired NSAAs.

Figure 3A:
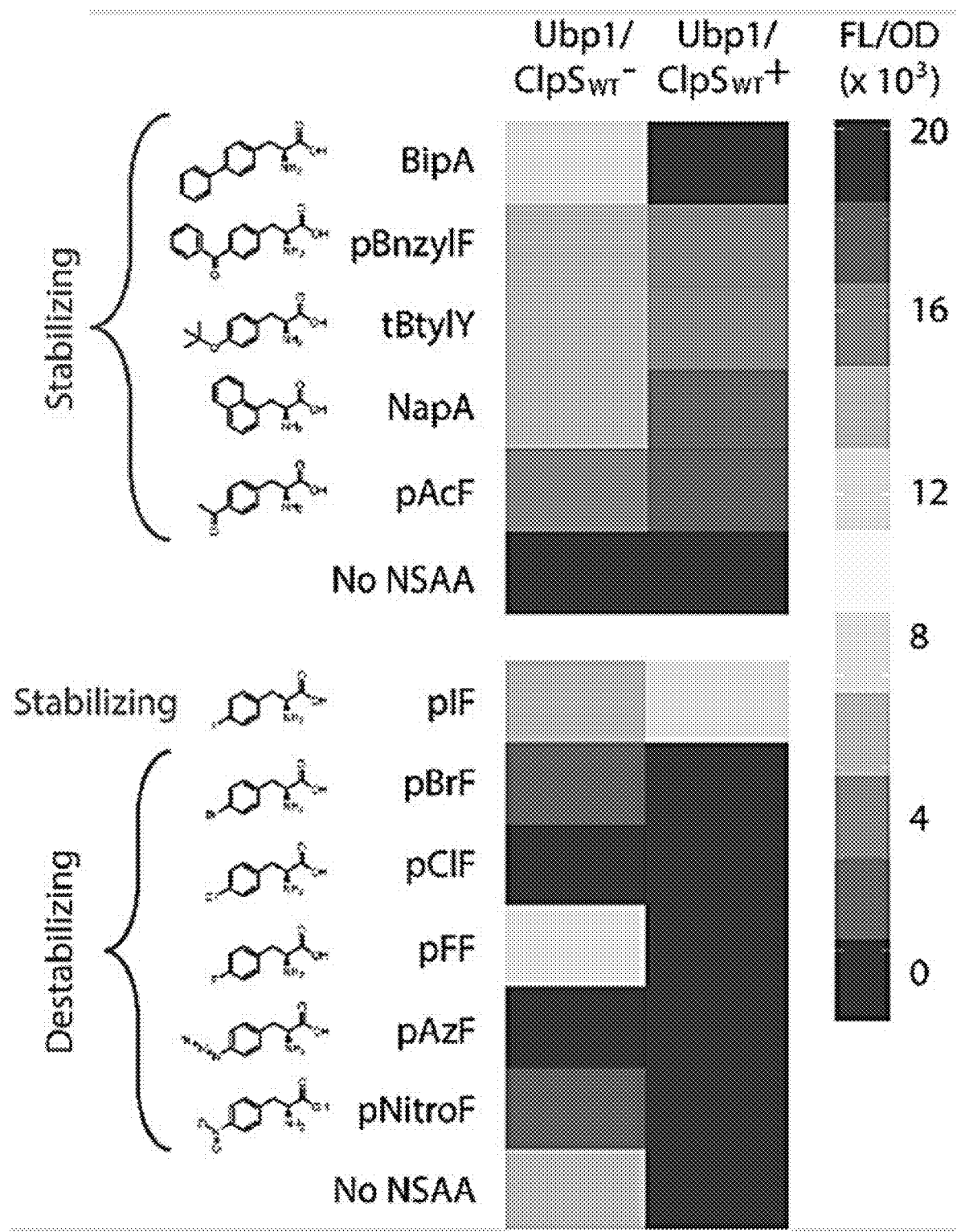
FIGS. 3A-3F shows PTP tunability through rational ClpS engineering.

It was next profiled incorporation of a more diverse set of NSAAs with PTP "Off" and "On" to better understand their N-end classification for potential engineering (FIG. 3A). Based on the difference in FL/OD between "Off" and "On" states using an OTS with limited activity on SAAs, we could learn whether an NSAA is N-end stabilizing or destabilizing. We began by using the BipyA OTS to screen several NSAAs because of its low NSAA− FL/OD. However, this OTS resulted in observable NSAA+FL/OD for only 5 out of 11 tested phenyl-NSAAs, with preference for large hydrophobic side chains at the para position of phenylalanine. Notably, NSAA+FL/OD for these 5 NSAAs was unaffected by PTP. The pAcF OTS was used to test incorporation of the 6 remaining NSAAs and appeared to broadly increase FL/OD for all with PTP "Off". We next observed a marked change in ΔFL/OD between PTP "Off" and "On" states based roughly on NSAA size. For p-Iodo-phenylalanine (pIF), FL/OD did not significantly change, and therefore pIF is N-end stabilizing. However, for p-Bromo-phenylalanine (pBrF) and other smaller or polar phenyl-NSAAs such as pAzF, FL/OD was significantly diminished when PTP was "On". The data suggest that smaller deviations from Y/F are tolerated by the ClpS binding pocket, making these NSAAs N-end destabilizing.

Figure 3B:
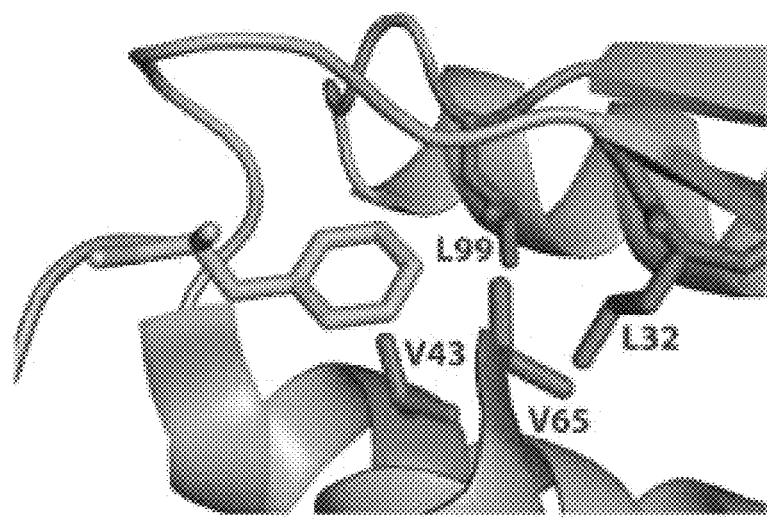
Figure 3C:
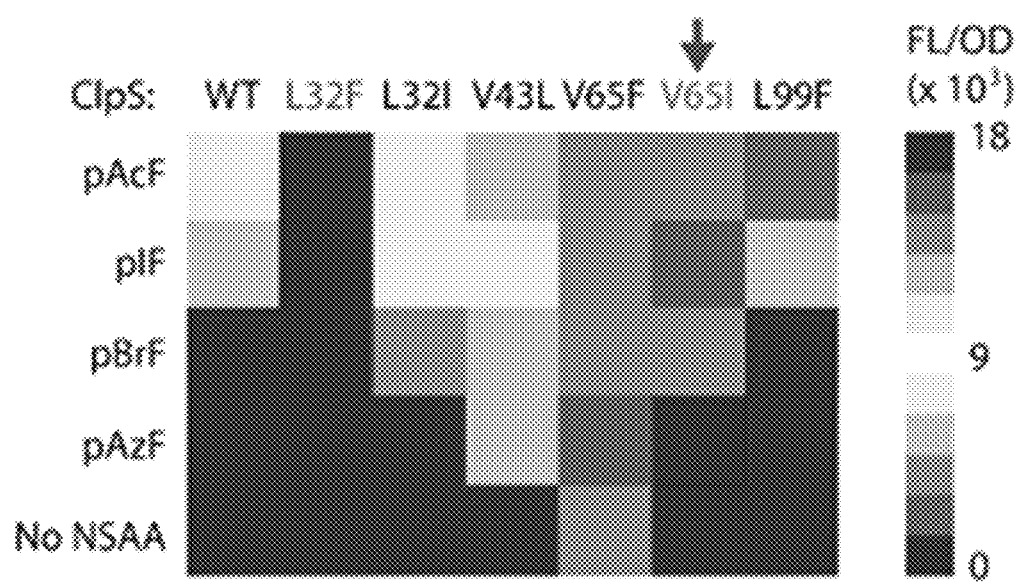
Figure 3D:
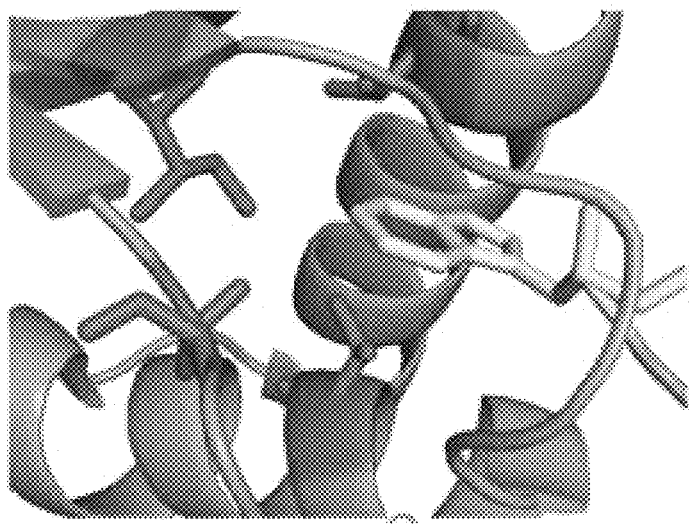
Figure 3E:
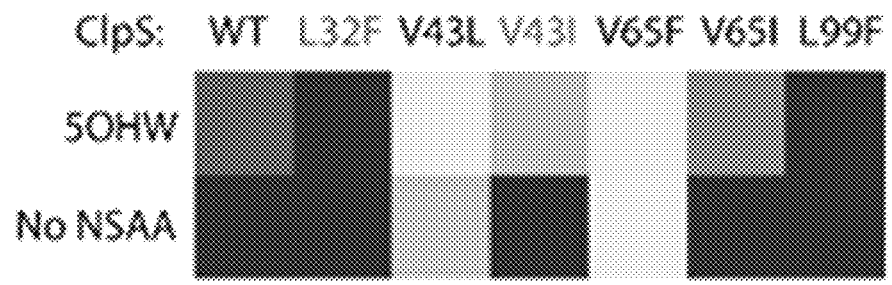
Figure 3F:
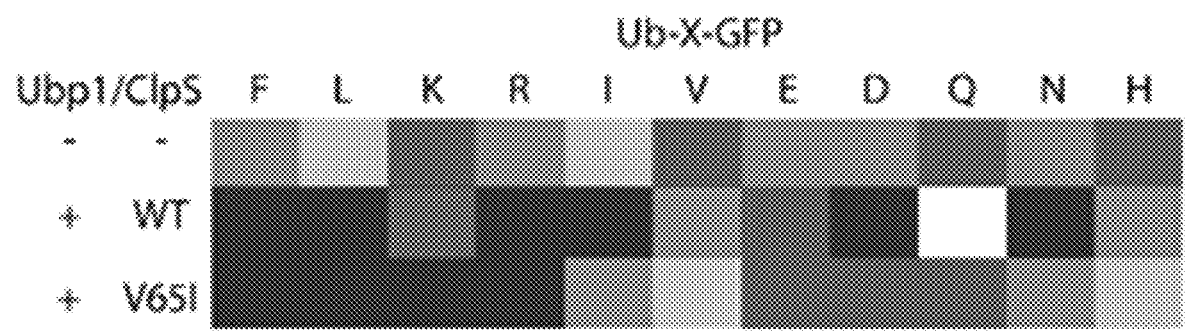
Figures 7A, 7B:
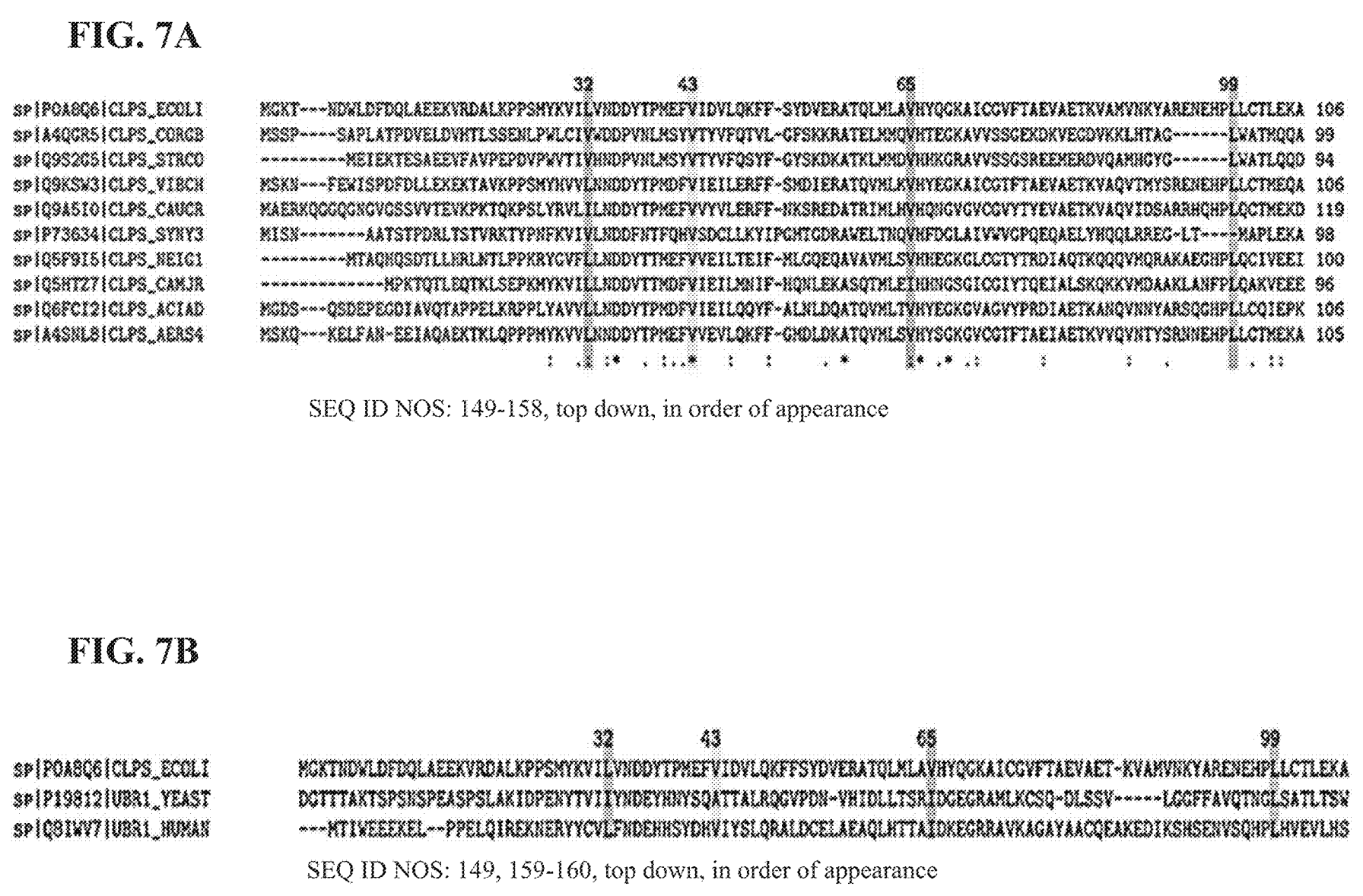
Figure 8:
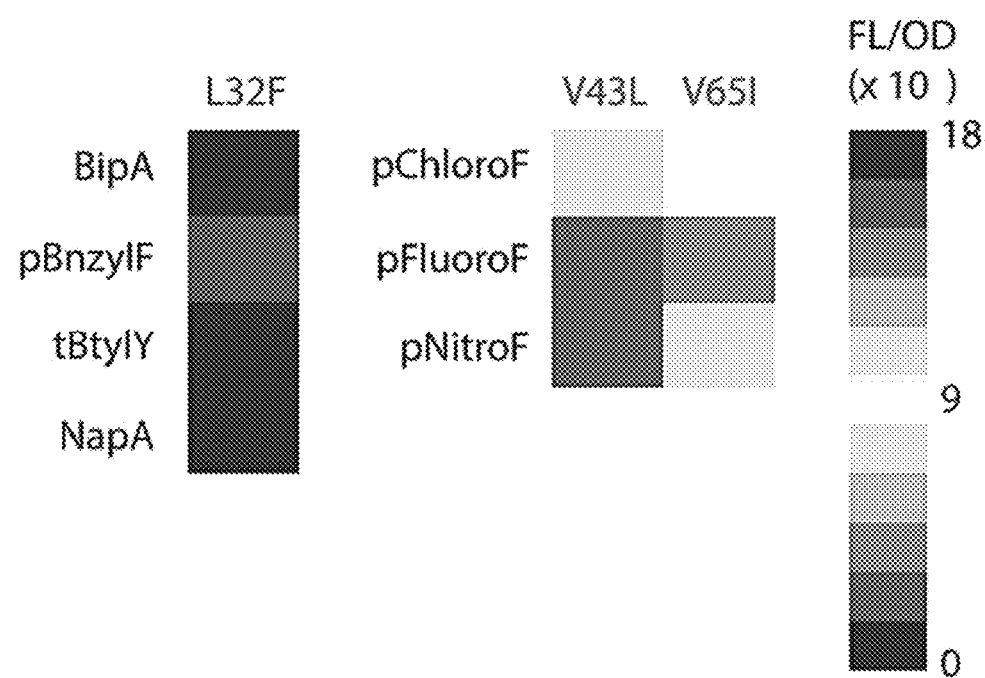
FIG. 8 shows characterization of select ClpS variants on broader panels of NSAAs.

By examining the ClpS crystal structure, we hypothesized that we could engineer ClpS to alter N-end rule classification of these NSAAs. We targeted four hydrophobic residues in the ClpS binding pocket for single point mutagenesis covering F/L/I/V (FIG. 3B). Sequence alignments of ClpS homologs across prokaryotes and eukaryotes showed conservation of these residues among related hydrophobic amino acids (FIGS. 7A-7B). By screening the resulting 12 single mutants in a ClpS-deficient strain (C321.ΔClpS.Ub-UAG-sfGFP) with select NSAAs and the pAcF OTS, we identified a variant (ClpS$^{V65I}$) that resulted in at least partial stabilization of all screened N-end phenyl NSAAs while maintaining low NSAA− FL/OD (FIG. 3C). In addition, we identified a variant (ClpS$^{L32F}$) that resulted in complete degradation of all but the two largest screened N-end phenyl NSAAs (FIG. 8). This small rationally engineered library contained several variants with specificities for different sets of NSAAs, showcasing the remarkable tunability of PTP. We further asked whether library members could distinguish tryptophanyl analogs from tryptophan using the 5OHW OTS (FIG. 3D). Although 5OHW is N-end destabilizing with ClpS, we observed that ClpS$^{V43I}$ and ClpS$^{V65I}$ improved discrimination of 5OHW from W (FIG. 3E). This result confirmed that the 5OHW OTS could incorporate 5OHW and that the previously observed signal was not predominantly due to misincorporation of SAAs. Furthermore, our rational designs could distinguish small modifications on a variety of chemical templates, i.e. NSAAs with phenyl as well as indole sidechains. Given the desirable properties of ClpS$^{V65I}$ for our NSAAs of interest, we wanted to examine whether it alters N-end rule classification for SAAs. We substituted the UAG codon in our GFP reporter for codons encoding a representative panel of SAAs and found that ClpS$^{V65I}$ affects stability of these N-end SAAs no differently than ClpS (FIG. 3F). Interestingly, overexpression of either ClpS or ClpS$^{V65I}$ lead to degradation of N-end I/V. Though these are not normally classified as N-end destabilizing residues, no one has previously overexpressed ClpS in E. coli and it exhibits weak affinity for these substrates in vitro (33).

EXAMPLE III

Engineered ClpS Mutants

As shown in FIGS. 7A-7B, the crystal structure of the ClpS protein was used to rationally engineer ClpS variants that have tunable specificities for degrading different sizes of NSAAs, including undetectable degradation of tested analogs of Y/F while maintaining full degradation of Y/F with the ClpS_V65I and ClpS_V43I mutants. The term "V65I" or "V43I" is a standard notation for describing a mutation where the amino acid I has been substituted for amino acid V at position 65 or 43. The ClpS_V65I and ClpS_V43I mutants were capable of distinguishing between standard amino acids and their nonstandard amino acid counterparts when positioned at the N-terminus of a protein for purposes of degradation. One aspect of the present disclosure is to inactivate endogenous ClpS if the ClpS_V65I or ClpS_V43I mutant is being used. Inactivation of ClpS prevents indiscriminate or nonselective degradation of proteins including smaller nonstandard amino acids. Another useful mutant is ClpS_L32F, which causes biphenylalanine (bipA) and p-benzoylphenylalanine (pBnzylF) to be N-end stabilizing and all other tested NSAAs to be N-end destabilizing. In other words, the ClpS_L32F mutant can be used to discriminate between incorporated bipA and all other incorporated NSAAs other than pBnzylF (see FIG. 8).

EXAMPLE IV

Local Sense Codon Reassignment

Aspects of the present disclosure are directed to local sense codon reassignment. Instead of using a stop codon for nonstandard amino acid incorporation, a sense codon can be used which creates competition for an N-terminal sense codon between a standard amino acid and a nonstandard amino acid. If the standard amino acid corresponding to the sense codon is destabilizing by the N-end rule, all of the proteins which do not include a sense codon reassigned to a nonstandard amino acid will be degraded. As shown in FIG. 8 with respect to the UAC codon which normally encodes tyrosine, when expression of Ubp1/ClpS is induced, nearly all of the GFP containing tyrosine gets degraded. If competition for the UAC codon with nonstandard amino acid is present, then nonstandard amino acid incorporation into the N-terminus of the GFP reporter protein can be detected by measuring the FL/OD increase.

EXAMPLE V

Materials and Methods

Strains and Strain Engineering

E. coli strain C321.ΔA (CP006698.1), which was previously engineered to be devoid of UAG codons and RF1, was the starting strain used for this study (27). The TET promoter and Ub-UAG-sfGFP expression cassette was genomically integrated using λ Red recombineering (44, 45) and tolC negative selection using Colicin E1 (46, 47). This resulted in strain C321.Ub-UAG-sfGFP. Please see Table 1 for sequences of key constructs such as the reporter construct. Multiplex automatable genome engineering (MAGE) (48) was used to inactivate the endogenous mutS and clpS genes when needed and to add or remove UAG codons in the integrated reporter. For MAGE, saturated overnight cultures were diluted 100-fold into 3 mL LB$^L$ containing appropriate antibiotics and grown at 34° C. until mid-log. The integrated Lambda Red cassette in C321.AA derived strains was induced in a shaking water bath (42° C., 300 rpm, 15 minutes), followed by cooling culture tubes on ice for at least two minutes. These cells were made electrocompetent at 4° C. by pelleting 1 mL of culture (16,000 rcf, 20 seconds) and washing twice with 1 mL ice cold deionized water (dH2O). Electrocompetent pellets were resuspended in 50 µL of dH2O containing the desired DNA. For MAGE oligonucleotides, 5 µM of each oligonucleotide was used. Please see Table 2 for a list of all oligonucleotides used in this study. For integration of dsDNA cassettes, 50 ng was used. Allele-specific colony PCR (ASC-PCR) was used to identify desired colonies resulting from MAGE as previously described (49). Colony PCR was performed using Kapa 2G Fast HotStart ReadyMix according to manufacturer protocols and Sanger sequencing was performed by Genewiz to verify strain engineering. The strains C321.Ub-UAG-sfGFP, C321.Ub-UAG-sfGFP_UAG151, and C321.ΔClpS.Ub-UAG-sfGFP are available from Addgene. Ub-X-GFP reporters containing codons encoding SAAs in place of UAG were generated from Ub-UAG-GFP by PCR and Gibson assembly, and they were subsequently cloned into the pOSIP-TT vector for Clonetegration (one-step cloning and chromosomal integration) into NEB5α strains (50). The UBP1/clpS_V65I operon was also placed under weak constitutive expression and integrated into C321.ΔClpS.Ub-UAG-sfGFP using Clonetegration. This strain (C321.Nend) was used as the host for FACS experiments.

TABLE 1

Sequences of key constructs

| Construct Name | Sequence | SEQ ID NO: |
|---|---|---|
| Ubiquitin-*-LFVQEL-sfGFP-His6x | ATGCAGATTTTTGTGAAGACTTTAACAGGTAAGACGATTACCCT GGAGGTGGAGTCCTCGGACACCATCGATAATGTAAAATCAAAA ATCCAAGATAAGGAAGGAATCCCTCCAGACCAGCAACGTCTGA TTTTCGCAGGTAAACAACTGGAGGATGGTCGCACGCTTTCGGAC TACAACATCCAGAAAGAATCTACCCTTCATTTGGTTCTGCGTCTG CGTGGAGGATAGTTGTTTGTGCAGGAGCTTgcatccaagggcgag gagctctttactggcgtagtaccaattctcgtagagctcgatggc gatgtaaatggccataagttttccgtacgcggcgagggcgaggc gatgcaactaacggcaagctcactctcaagtttatttgtac-tactg gcaagctcccagtaccatggccaactctcgtaactactctgacct atggcgtacaatgttttcccgctatccagatcacatgaagcaac atgatttttttaagtccgcaatgccagagggctatgtacaagagc gcactattagctttaaggatgatggcacctataagactcgcgcag aggtaaagtttgagggcgatactctcgtaaatcgcattgagctca agggcattgatttaaggaggatggcaatattctcggccataagc tggatataatttcaattcccataatgtatacattaccgcagataa gcaaaagaatggcattaaggcgaatttttaagattcgccataatgt ggaggatggctccgtacaactcgcagatcattatcaacaaaatac tccaattggcgatgcccagtactcctcccagataatcattatct ctccactcaatccgtgctctccaaagatccaaatgagaagcgcga tcacatggtactcctggagtttgtaactgcagcaggcattactca tggcatggatgagctctataagctcgagcaccaccaccaccaca ctaa | 5 |
| ClpS2_At gBlock | ATGTCTGATAGTCCTGTTGACTTAAAACCCAAGCCTAAAGTCAA GCCCAAATTAGAACGCCCAAAACTTTACAAAGTCATGTTATTGA ATGATGATTATACACCACGCGAATTTGTGACGGTAGTCCTTAAA GCGGTGTTTCGTATGTCAGAGGACACTGGTCGCCGTGTAATGAT GACAGCACATCGTTTTGGTTCGGCGGTGGTGGTCGTTTGTGAAC GTGACATTGCAGAGACGAAAGCCAAGGAGGCGACCGACTTGGG GAAGGAAGCAGGTTTTCCTTTGATGTTCACGACTGAGCCCGAGG AGTAA | 6 |
| pAzFRS.1.t1 gBlock | GTTATGcactacGATggtgttgacgttTACgttggtggtatggaa cagcgtaaaatccacatgctggcgcgtgaactgctgccgaaaaaa gttgtttgcatccacaacccggttctgaccggtctggacggtgaa ggtaaaatgtcttcttctaaaggtaacttcatcgcggttgacgac tctccggaagaaatccgtgcgaaaatcaaaaaagcgtactgcccg | 7 |

TABLE 1-continued

Sequences of key constructs

| Construct Name | Sequence | SEQ ID NO: |
|---|---|---|
| | gcgggtgttgttgaaggtaacccgatcatggaaatcgcgaaatac ttcctggaatacccgctgaccatcaaaGGT | |
| ScUBP1$^{ruc}$, or UBP1 | ATGGGGAGTGGGTCTTTCATTGCTGGGCTTGTCAACGATGGTAA TACGTGTTTTATGAACTCGGTTCTTCAGTCCCTTGCTAGTAGCCG TGAACTTATGGAGTTTTTGGATAATAATGTAATCCGTACATATG AAGAAATTGAACAGAACGAGCACAATGAGGAAGGTAATGGCCA AGAGAGCGCACAAGATGAGGCAACTCACAAAAAAAACACTCGC AAGGGAGGTAAGGTCTATGGGAAGCATAAAAAGAAATTAAACC GCAAATCTTCTAGCAAGGAAGACGAAGAAAAGTCGCAAGAACC AGACATTACGTTTTCGGTGGCGTTGCGTGATCTGCTGAGCGCAT TAAATGCTAAGTATTATCGCGACAAACCCTACTTTAAGACTAAC TCTTTATTAAAAGCGATGAGCAAGTCCCCGCGCAAAAATATCTT GCTTGGGTACGATCAAGAAGCGCTCAGGAATTTTTTCAAAACA TTCTTGCGGAGTTAGAArTCTAATGTCAAGTCGTTAAACACAGAA AAGCTTGATACTACACCGGTAGCCAAGTCCGAACTTCCAGACGA TGCTCTGGTTGGCCAATTAAACCTTGGTGAGGTAGGCACCGTGT ACATTCCCACAGAACAAATTGACCCCAATTCGATTTTACATGAC AAATCGATTCAAAACTTTACCCCCTTTAAACTGATGACCCCGTT GGATGGGATCACGGCTGAGCGCATCGGCTGCCTGCAATGCGGA GAGAACGGGGGAATTCGCTACAGTGTTTTCAGCGGATTAAGTTT GAACCTGCCGAATGAAAATATTGGAAGCACTCTTAAACTGTCCC AGTTACTGTCCGATTGGTCGAAACCCGAGATTATCGAGGGTGTTT GAATGCAACCGTTGCGCTTTAACAGCTGCGCACTCACACTTGTT TGGCCAATTAAAGGAGTTTGAGAAGAAACCTGAAGGCTCGATTC CCGAAAAACTTATTAATGCCGTAAAGGACCGCGTGCACCAGATC GAAGAGGTCTTGGCAAAGCCGGTTATCGACGATGAAGATTATA AAAAATTGCATACTGCGAATATGGTCCGCAAGTGTTCAAAAAGT AAACAAATTCTTATCTCTCGTCCACCACCTTTGTTGTCTATTCAT ATCAACCGCTCTGTTTTCGACCCGCGCACCTACATGATTCGCAA GAACAACTCCAAGGTTTTGTTCAAGTCACGCTTGAACCTGGCAC CCTGGTGCTGTGATATCAACGAAATCAATCTTGACGCACGCCTT CCGATGTCGAAGAAGGAAAAAGCAGCTCAACAAGATTCTTCTG AAGACGAGAACATTGGCGGAGAGTACTATACTAAATTGCATGA ACGTTTTGAGCAGGAGTTTGAAGATTCTGAAGAAGAGAAGGAA TACGATGATGCAGAGGGTAATTATGCATCGCATTATAACCATAC CAAGGACATCTCCAACTACGATCCATTGAATGGAGAAGTCGACG GTGTGACTTCCGATGATGAGGATGAATACATTGAAGAGACAGA CGCGTTGGGGAATACCATCAAAAAACGTATTATTGAACACTCCG ACGTGGAGAACGAAACGTGAAGGATAATGAAGAACTTCAGGA GATCGATAACGTTAGCTTGGATGAGCCAAAAATTAATGTCGAGG ACCAGCTTGAAACGAGTTCTGATGAGGAAGACGTTATTCCTGCT CCACCCATCAACTACGCTCGCAGCTTTAGTAGGTACGGTCCCAGCGAC CCCTTTAACTTACTCTTTGCGCAGCGTCATCGTGCACTATGGGAC TCACAACTACGGACATTATATTGCATTTCGCAAGTATCGTGGAT GTTGGTGGCGCATCTCCGATGAGACGGTCTATGTGGTAGATGAG GCCGAAGTACTGTCAACACCGGGGGTATTTATGCTTTTCTACGA GTATGATTTCGACGAGGAGACCGGAAAAATGAAAGACGACTTA GAAGCTATCCAGAGCAATAATGAGGAAGATGACGAGAAAGAAC AGGAACAGAAGGGTGTCCAGGAGCCAAAAGAATCCCAGGAGCA AGGCGAAGGCGAAGAACAAGAAGAAGGGCAAGAGCAAATGAA ATTTGAGCGTACGGAGGATCATCGCGACATTTCAGGGAAGGATG TGAATTAA | 8 |

TABLE 2

Oligonucleotides used

| Oligo Name | Sequence | SEQ ID NO: |
|---|---|---|
| pZE21-seq-F | CCATTATTATCATGACATTAACC | 9 |
| pZE21-seq-R | GGATTTGTCCTACTCAGGAG | 10 |
| AARS-seq-F | CTTTTTATCGCAACTCTC | 11 |
| Ubiquitin + N-degron-F | TTAAAGAGGAGAAATTAACTATGCAGATTTTTGTGAAGACT | 12 |
| Ubiquitin + N-degron-R | AGCTCCTCGCCCTTGGATGCAAGCTCCTGCACAAACAAGT | 13 |
| pEVOLbbone_Ubp1-F | CAGGGAAGGATGTGAATTAATAAGTCGACCATCATCATCA | 14 |

TABLE 2-continued

Oligonucleotides used

| Oligo Name | Sequence | SEQ ID NO: |
|---|---|---|
| pEVOLbbone_Ubp1-R | ATGAAAGACCCACTCCCCATAGATCTAATTCCTCCTGTTAGC | 15 |
| Ubp1-P1-F | TAACAGGAGGAATTAGATCTATGGGGAGTGGGTCTTTCAT | 16 |
| Ubp1-P1-R | TCAAGCGTGACTTGAACAAAACCTTGGAGTTGTTCTTGCG | 17 |
| Upb1-P2-F | CGCAAGAACAACTCCAAGGTTTTGTTCAAGTCACGCTTGA | 18 |
| Upb1-P2-R | TGATGATGATGGTCGACTTATTAATTCACATCCTTCCCTGA | 19 |
| pUbi-*-Ndeg-GFP-F | TGCGTCTGCGTGGAGGATAGTTGTTTGTGCAGGAGCTTGC | 20 |
| pUbi-*-Ndeg-GFP-R | AAGCTCCTGCACAAACAACTATCCTCCACGCAGACGC | 21 |
| Ubp1_int-seq-F | GCTTGGGTACGATCAAGAAG | 22 |
| Ubp1_int-seq-R | CCTTGGTATGGTTATAATGCG | 23 |
| pZE21bbone4Ubp1-F | CAGGGAAGGATGTGAATTAAAAGCTTGATGGGGGATCCCA | 24 |
| pZE21bbone4Ubp1-R | ATGAAAGACCCACTCCCCATGGTACCTTTCTCCTCTTTAATGAAT | 25 |
| Ubp1-ins-F | TTAAAGAGGAGAAAGGTACCATGGGGAGTGGGTCTTTCAT | 26 |
| Ubp1-ins-R | TGGGATCCCCCATCAAGCTTTTAATTCACATCCTTCCCTGA | 27 |
| UbiGFPins-F | TAAAGAGGAGAAAGGTACCATGCAGATTTTTGTGAAGACTTTAAC | 28 |
| UbiGFPins-R | TGGGATCCCCCATCAAGCTTTTAGTGGTGGTGGTGGTGGT | 29 |
| pZEbbone4UbiGFP-F | ACCACCACCACCACCACTAAAAGCTTGATGGGGGATCCCA | 30 |
| pZEbbone4UbiGFP-R | GTCTTCACAAAAATCTGCATGGTACCTTTCTCCTCTTTAATGAAT | 31 |
| reporter_to_genome-F | TTACGGGCTAATTACAGGCAGAGAAATGCGTGATGTGTGCCACACTTGTTGATCCCTATCAGTGATAGAGATTGAC | 32 |
| reporter_to_genome-R | CCAGCGGGCTAACTTTCCTCGCCGGAAGAGTGGTTAACAAAATAGTAACGTCACCGACAAACAACAGATAAAAC | 33 |
| SIR-seq-F | CCAAAGTGAGTTGAGTATAAC | 34 |
| SIR-seq-R | TTTCTCCTTATTATCAATGC | 35 |
| r2g-extend-F | GCCGCAGCAAGCCAAAGTGAGTTGAGTATAACGCAAATTTGCTACTGGTCCGATGGGTGCAATGGTCTGAATTACGGGCTAATTACAGGC | 36 |
| r2g-extend-R | AACGCAATCGCAACCGCTAAACCACTGGCCATGTGCACGAGTTTCATTCATTTCTCCTTATTATCAATGCACCAGCGGGCTAACTTTC | 37 |
| MAGE_*toS | t*a*aagagctcctcgcccttggatgcAAGCTCCTGCACAAACAACgATCCTCCACGCAGACGCAGAACCAAATGAAGGGTAGATTCTTTCT | 38 |
| asPCR-S-F | CGTCTGCGTGGAGGATC | 39 |
| asPCR-*-F | CGTCTGCGTGGAGGATA | 40 |
| pZE-Ubp1bbone4ClpP-F | TTCTGACCCATCGTAATTAAaagcttgatgggggatccca | 41 |
| pZE-Ubp1bbone4ClpP-R | tGGTATATCTCCTTTTATTATTAATTCACATCCTTCCCTGAAAT | 42 |
| clpPins-F | GTGAATTAATAATAAAAGGAGATATACCatgTCATACAGCGGCGA | 43 |
| clpPins-R | tgggatcccccatcaagcttTTAATTACGATGGGTCAGAATCG | 44 |
| pEVOLtRNA-p1-F | ctgccaacttactgatttagtgtatgatggtgttttttgagg | 45 |
| pEVOLtRNA-p1-R | gccgcttagttagccgtgcaaacttatatcgtatggggctg | 46 |

TABLE 2-continued

Oligonucleotides used

| Oligo Name | Sequence | SEQ ID NO: |
|---|---|---|
| pEVOLtRNA-p2-F | agccccatacgatataagtttgcacggctaactaagcggc | 47 |
| pEVOLtRNA-p2-R | ctcaaaaacaccatcatacactaaatcagtaagttggcagcatca | 48 |
| pZE-Ubp1bbone4ClpS-F | TGTGTACGCTAGAAAAAGCCTAAaagcttgatgggggatc | 49 |
| pZE-Ubp1bbone4ClpS-R | GTTCGTTTTACCcatGGTATATCTCCTTTTATTATTAATTCACAT | 50 |
| ClpSins-F | ATAATAAAAGGAGATATACCatgGGTAAAACGAACGACTG | 51 |
| ClpSins-R | gatcccccatcaagcttTTAGGCTTTTTCTAGCGTACACA | 52 |
| AARSlibraryins-F | tactgtttctccatacccgttttttgggctaacaggaggaattagatct | 53 |
| pEVOLbbone4lib-R | agatctaattcctcctgttagcc | 54 |
| mutS_null_mut-2* | A*C*CCCATGAGTGCAATAGAAAATTTCGACGCCCATACGCCCATGATGCAGCAGTGATAGTCGCTGAAAGCCCAGCATCCCGAGATCCTGC | 55 |
| mutS_null_revert-2* | A*C*CCCATGAGTGCAATAGAAAATTTCGACGCCCATACGCCCATGATGCAGCAGTATCTCAGGCTGAAAGCCCAGCATCCCGAGATCCTGC | 56 |
| mutS-2_ascPCR_wt-F | CCATGATGCAGCAGTATCTCAG | 57 |
| mutS-2_ascPCR_mut-F | CCATGATGCAGCAGTGATAGTC | 58 |
| mutS-2_ascPCR-R | AGGTTGTCCTGACGCTCCTG | 59 |
| ASPCR-151UAG-F | GTATAATTTCAATTCCCATAATGTATAG | 60 |
| ASPCR-151UAC-F | GTATAATTTCAATTCCCATAATGTATAC | 61 |
| ASPCR-151-R | ctcgagcttatagagctcatc | 62 |
| Remove151UAG-MAGE_corrected | c*t*taaaattcgccttaatgccattcttttgcttatctgcggtaatgtatacattatgggaattgaaattatactccagcttatggccgag | 63 |
| ClpS.inact-MAGE | C*T*TTTTCTTCCGCCAGTTGATCAAAGTCCAGCCAGTCGTTCtaTTatCaCATTGTCAGTTATCATCTTCGGTTACGGTTATCGGCAGAAC | 64 |
| ASPCR-ClpS_WT-F | CCGATAACCGTAACCGAAGATGATAACTGACAATGG | 65 |
| ASPCR-ClpS.inact-F | CCGATAACCGTAACCGAAGATGATAACTGACAATGT | 66 |
| ASPCR-ClpS-R | CGTACTTGTTCACCATCGCCACTTTGGT | 67 |
| pZE-Ubbone4ClpS2_At-F | CGACTGAGCCCGAGGAGTAAaagcttgatgggggatccca | 68 |
| pZE-Ubbone4ClpS2_At-R | TCAACAGGACTATCAGACATGGTATATCTCCTTTTATTATTAATTCACATCC | 69 |
| ClpS2_At-ins-F | ATAATAAAAGGAGATATACCATGTCTGATAGTCCTGTTGACTT | 70 |
| ClpS2_At-ins-R | tgggatcccccatcaagcttTTACTCCTCGGGCTCAGTCG | 71 |
| ClpS_M40A-F | ATGATGATTACACTCCGGCGGAGTTTGTTATTGACGTGT | 72 |
| ClpS_M40A-R | CGTCAATAACAAACTCCGCCGGAGTGTAATCATCATTGAC | 73 |
| pOSIPbbone-F | taacctaaactgacaggcat | 74 |
| pOSIPbbone-R | ttccgatccccaattcct | 75 |
| pEVOL-araC-seq-1 | GGATCATTTTGCGCTTCAG | 76 |
| pEVOL-araC-seq-2 | GAATATAACCTTTCATTCCC | 77 |

TABLE 2-continued

Oligonucleotides used

| Oligo Name | Sequence | SEQ ID NO: |
|---|---|---|
| PylRSmiddle-seq | GTGTTTCGACTAGCATTTC | 78 |
| PylRSend-seq | GGTCAAACATGATTTCAAAAAC | 79 |
| pEVOLCmR-seq-R | caacagtactgcgatgag | 80 |
| upstreamClpS-F | GCAAATAAGCTCTTGTCAGC | 81 |
| ClpS_L32-NTC-F | CATCTATGTATAAAGTGATANTCGTCAATGATGATTACACTCCG | 82 |
| ClpS_32-R | TATCACTTTATACATAGATG | 83 |
| ClpS-V43-NTT-F | ATTACACTCCGATGGAGTTTNTTATTGACGTGTTACAAAAATTC | 84 |
| ClpS_43-R | AAACTCCATCGGAGTGTAAT | 85 |
| ClpS_V65-NTT-F | CAACGCAATTGATGCTCGCTNTTCACTACCAGGGGAAGG | 86 |
| ClpS_65-R | AGCGAGCATCAATTGCGTTG | 87 |
| ClpS_L99-NTC-F | CGAGGGAGAATGAGCATCCANTCCTGTGTACGCTAGAAAAAGC | 88 |
| ClpS_99-R | TGGATGCTCATTCTCCCTCG | 89 |
| Alt_ClpS-R_forL99 | gcggatttgtcctactcag | 90 |
| AARS-inducible-only-F | gctaacaggaggaattagatct | 91 |
| AARS-inducible-only-R | ttgataatctaacaaggattatggg | 92 |
| pEVOLbbone-Ind-only-F | cccataatccttgttagattatcaaaggcattttgctattaaggg | 93 |
| pEVOL-bbone-ind-only-R | agatctaattcctcctgttagc | 94 |
| protosens-bbone-F | TAACTCGAGGCTGTTTTGG | 95 |
| protosens-bbone-R | CATATGTATATCTCCTTGTGCATC | 96 |
| Ubp1ClpS4protosens-F | GATGCACAAGGAGATATACATATGGGGAGTGGGTCTTTCAT | 97 |
| Ubp1ClpS4protosens-R | CCAAAACAGCCTCGAGTTAGGCTTTTTCTAGCGTACA | 98 |
| pAzFRS.1.t1-ins-F | acccgatcatgcaggttaacGTTATGcactacGATggtgt | 99 |
| pAzFRS.1.t1-ins-R | tcaccaccgaattttttccggACCtttgatggtcagcg | 100 |
| bbone4pAzFRS.1.t1-F | ccggaaaaattcggtggtga | 101 |
| bbone4pAzFRS.1.t1-R | gttaacctgcatgatcgggt | 102 |
| pZEbbone4tetR-F | acgctctcctgagtaggac | 103 |
| pZEbbone4tetR-R | tcaccgacaaacaacagataaaac | 104 |
| TetR-ins-F | tatctgttgtttgtcggtgaacgtctcattttcgccagat | 105 |
| TetR-ins-R | gtcctactcaggagagcgtagtgtcaactttatggctagc | 106 |
| pDULE-ABK-bbone-F | cgacctgaatggaagcc | 107 |
| pDULE-ABK-bbone-R | catacacggtgcctgac | 108 |
| CmRins4pDULE-F | aacgcagtcaggcaccgtgtatggagaaaaaaatcactggatatac | 109 |
| CmR4pDULE-R | gccggcttccattcaggtcgaaaaaattacgccccgc | 110 |
| pCNFRS-65-67-70-NNK-F | CAAAATGCTGGATTTGATATAATTATANNKTTGNNKGATTTANNKGCCTATTTAAACCAGAAAGGAGAG | 111 |
| pCNFRS-65-R | TATAATTATATCAAATCCAGCATTTTGTAAATC | 112 |
| pCNFRS-108- | GGCAAAATATGTTTATGGAAGTGAANNKNNKCTTGATAAG | 113 |

TABLE 2-continued

Oligonucleotides used

| Oligo Name | Sequence | SEQ ID NO: |
|---|---|---|
| 109-114-NNK-F | GATNNKACACTGAATGTCTATAGATTGGC | |
| pCNFRS-108-R | TTCACTTCCATAAACATATTTTGCC | 114 |
| pCNFRS-155-157-161-NNK-F | GAAGTTATCTATCCAATAATGNNKGTTNNKGGTGCTCATNNKCTTGGCGTTGATGTTGCAG | 115 |
| pCNFRS-155-R | CATTATTGGATAGATAACTTCAGCAAC | 116 |
| libraryINS-seq-R | CGCATCAGGCAATTTAGC | 117 |
| BipARS_P144Q-F | cgcgcgtgaagacgaaaaccagaaagttgcggaagttatctac | 118 |
| BipARS_P144Q-R | ggttttcgtcttcacgcg | 119 |
| BipARS_N157K-F | tacccgatcatgcaggttaaaggtatccactacaaaggtgttg | 120 |
| BipARS_N157K-R | ttaacctgcatgatcgggta | 121 |
| BipARS_R181C-F | gtaaaatccacatgctggcgtgtgaactgctgccgaaa | 122 |
| BipARS_R181C-R | cgccagcatgtggatttta | 123 |
| BipARS_I255F-F | tctggaatacccgctgaccttcaaacgtccggaaaaattc | 124 |
| BipARS_I255F-R | ggtcagcgggtattccag | 125 |
| BipARS_E259V-F | gctgaccatcaaacgtccggtaaaattcggtggtgacctg | 126 |
| BipARS_E259V-R | ccggacgtttgatggtc | 127 |
| BipARS_P284S-F | tcaaaaacaaagaactgcactcgatgcgtctgaaaaacg | 128 |
| BipARS_P284S-R | gtgcagttctttgttttttgaac | 129 |
| pEVOLbbone4libv2-F | ctgcagatcaaacgctaaattg | 130 |
| AARSlibraryinsv2-R | taggcctgataagcgtagcgcatcaggcaatttagcgtttgaaactgcag | 131 |
| BipARS_G257R-F | aatacccgctgaccatcaaacgtccggaaaaattcggtg | 132 |
| BipARS_G257R-R | accaccgaattttttccggacgtttgatggtcagcgggtat | 133 |
| BipARS-100AA-F | gcgaaatacgtttacggttc | 134 |
| BipARS-100AA-R | gaaccgtaaacgtatttcgc | 135 |
| BipARS-200AA-F | ggacggtgaaggtaaaatgtc | 136 |
| BipARS-200AA-R | gacattttaccttcaccgtcc | 137 |
| pZErepbbone4pylT-F | cggcgccagggttgttttttcacgctctcctgagtaggaca | 138 |
| pZErepbbone4pylT-R | ttccattcaggtcgaaaaaaagtgtcaactttatggctagc | 139 |
| pylTpDULE-F | ttttttcgacctgaatggaagc | 140 |
| pylTpDULE-R | gaaaaacaaccctggcgc | 141 |
| pZEbbone4pylTonly-F | cggcgccagggttgttttttcacgctctcctgagtaggaca | 138 |
| pZEbbone4pylTonly-R | ttccattcaggtcgaaaaaaactcgaggtgaagacgaaagg | 142 |
| ClpS-Lib-F | ACATTTCAGGGAAGGATGTGAATTAATAATAAAAGGAGATATACC | 143 |
| ClpS-Lib-R | gcgtaccatgggacccccatcaagcttTTA | 144 |
| pZEbbone4ClpSlib-F | TAAaagcttgatgggggatc | 145 |
| pZEbbone4ClpSlib-R | GGTATATCTCCTTTTATTATTAATTCACATCC | 146 |
| ClpS-Lib-Seq | GGATCATCGCGACATTTC | 147 |

Plasmids and Plasmid Construction

Two copies of orthogonal MjTyrRS-derived AARSs and tRNA$_{CUA}^{opt Tyr}$ were kindly provided in pEVOL plasmids by Dr. Peter Schultz (Scripps Institute) (10). AARSs used in this study were the following: BipARS (14), BipyARS (14), pAcFRS (38), pAzFRS (39), and NapARS (40). The pEVOL plasmids were maintained using chloramphenicol. Original plasmids harboring two AARS copies were used for synthetase promiscuity comparison experiments (FIGS. 2A-2C and 3A-3F). For generation and characterization of synthetase variants, plasmids harboring only one AARS copy under inducible expression were constructed using Gibson assembly (41). The ScWRS-R3-13 AARS was synthesized as codon-optimized for expression in E. coli and cloned into the pEVOL plasmid along with its associated tRNA (6, 8). In all cases, tRNA is constitutively expressed and AARS expression is either arabinose inducible or constitutive.

An N-terminally truncated form of the UBP1 gene from Saccharomyces cerevisiae (30, 31) (ScUBP1$^{trunc}$ or simply UBP1) was synthesized as codon-optimized for expression in E. coli and cloned into the pZE21 vector (Kanamycin resistance, ColE1 origin, TET promoter) (Expressys). The E. coli genes clpS and clpP were PCR amplified from E. coli MG1655 and cloned into artificial operons downstream of the UBP1 gene in the pZE21 vector using Gibson assembly. Artificial operons were created by inserting the following RBS sequence between the UBP1 and clp genes: TAATAAAAGGAGATATACC (SEQ ID NO: 148). This RBS was originally designed using the RBS calculator (42) and previously validated in the context of another artificial operon (43). Rational engineering of ClpS variants was performed by dividing the clpS gene into two amplicons where the second amplicon contained a degenerate NTC or NTT sequence in the oligo corresponding to each codon of interest. The four initial positions of interest in the clpS gene correspond to amino acids 32, 43, 65, and 99. In each case, Gibson assembly was used to ligate both amplicons and the backbone plasmid. The pZE/UBP1/ClpS and pZE/UBP1/ClpS_V65I plasmids are available from Addgene.

Three reporter constructs were initially cloned into pZE21 vectors before use as templates for PCR amplification and genomic integration. The first of these consists of a Ubiquitin-*-LFVQEL-sfGFP-His6× fusion ("LFVQEL" disclosed as SEQ ID NO: 4 and "His6×" disclosed as SEQ ID NO: 3) ("Ub-UAG-sfGFP") downstream of the TET promoter. The second has an additional UAG codon internal to the sfGFP at position Y151* ("Ub-UAG-sfGFP_151UAG"). The third has an ATG codon (encoding methionine) in place of the first UAG ("Ub-M-sfGFP_151UAG").

Culture Conditions

Cultures for general culturing used herein were grown in LB-Lennox medium (LB$^L$: 10 g/L bacto tryptone, 5 g/L sodium chloride, 5 g/L yeast extract). Cultures for experiments in FIGS. 3A-3F were grown in 2×YT medium (2×YT: 16 g/L bacto tryptone, 10 g/L bacto yeast extract, 5 g/L sodium chloride) given improved observed final culture densities compared to LB$^L$ upon expression of ClpS variants. Unless otherwise indicated, all cultures were grown in biological triplicate in 96-well deep-well plates in 300 µL culture volumes at 34 C and 400 rpm.

Minimal Media SAA Spiking Experiments

Minimal media adapted C321.ΔA strains harboring either (i) pZE21/Ub-M-sfGFP_151UAG only, (ii) pZE21/Ub-M-sfGFP_151UAG and pEVOL/MjtRNA$_{CUA}^{opt Tyr}$, (iii) pZE21/Ub-M-sfGFP_151UAG only and pEVOL/bipARS_WT-tRNA_WT, or (iv) pZE21/Ub-M-sfGFP_151UAG only and pEVOL/bipARS_10-tRNA_10 were inoculated from frozen stocks in at least experimental duplicates. A 1×M9 salt medium containing 6.78 g/L Na$_2$HPO$_4$. 7H$_2$O, 3 g/L KH$_2$PO$_4$, 1 g/L NH$_4$Cl, and 0.5 g/L NaCl, supplemented with 2 mM MgSO$_4$, 0.1 mM CaCl$_2$, 1% glycerol, trace elements, 0.25 µg/L D-biotin, and carbenicillin was used as the culture medium. The trace element solution (100×) used contained 5 g/L EDTA, 0.83 g/L FeCl$_3$.6H$_2$O, 84 mg/L ZnCl$_2$, 10 mg/L CoCl$_2$.6H$_2$O, 13 mg/L CuCl$_2$.2H$_2$O, 1.6 mg/L MnCl$_2$.2H$_2$O and 10 mg/L H$_3$BO$_3$ dissolved in water (51). Inoculum were grown to confluence overnight in deep 96-well plates containing supplemented with 0.2% arabinose and chloramphenicol and/or kanamycin. Experimental cultures were inoculated at 1:7 dilution in the same media supplemented with each of the 20 standard amino acids or bipA to 1 mM or 100 uM, respectively. Cultures were incubated at 34° C. to an OD$_{600}$ of 0.5-0.8 in a shaking plate incubator at 1050 rpm (~4-5 h). GFP expression was induced by addition of anhydrotetracycline, and cells were incubated at 34° C. for an additional 16-20 h before measurement. All assays were performed in 96-well plate format. Cells were centrifuged at 5,000 g for 5 min, washed with 1×PBS, and resuspended in 1×PBS after a second spin. GFP fluorescence was measured on a Biotek spectrophotometric plate reader using excitation and emission wavelengths of 485 and 525 nm. Fluorescence was then normalized by the OD$_{600}$ reading to obtain FL/OD. Average normalized FL/OD from 3 independent experiments were plotted.

NSAA Incorporation Assays

Strains harboring integrated GFP reporters and AARS/tRNA plasmids were inoculated from frozen stocks of biological triplicate and grown to confluence overnight in deep well plates. Experimental cultures were inoculated at 1:100 dilution in either LB$^L$ or 2×YT media supplemented with chloramphenicol, arabinose, and the appropriate NSAA. Cultures were incubated at 34° C. to an OD$_{600}$ of 0.5-0.8 in a shaking plate incubator at 400 rpm (~4-5 h). GFP expression was induced by addition of anhydrotetracycline, and cells were incubated at 34° C. for an additional 16-20 h.

All assays were performed in 96-well plate format. Cells were centrifuged at 5,000 g for 3 min, washed with PBS, and resuspended in PBS after a second spin. GFP fluorescence was measured on a Biotek spectrophotometric plate reader using excitation and emission wavelengths of 485 and 525 nm. Fluorescence signals were corrected for autofluorescence as a linear function of OD$_{600}$ using the parent C321.ΔA strain that does not contain a reporter. Fluorescence was then normalized by the OD$_{600}$ reading to obtain FL/OD.

Chemicals

NSAAs used in this study were purchased from PepTech Corporation, Sigma Aldrich, Santa Cruz Biotechnology, and Toronto Research Chemicals. The following NSAAs were purchased: L-4,4-Biphenylalanine (BipA), L-4-Benzoylphenylalanine (pBenzoylF), O-tert-Butyl-L-tyrosine (tButylY), L-2-Naphthylalanine (NapA), L-4-Acetylphenylalanine (pAcF), L-4-Iodophenylalanine (pIF), L-4-Bromophenylalanine (pBromoF), L-4-Chlorophenylalanine (pChloroF), L-4-Fluorophenylalanine (pFluoroF), L-4-Azidophenylalanine (pAzF), L-4-Nitrophenylalanine, L-4-Cyanophenylalanine, L-3-Iodophenylalanine, L-phenylalanine, L-tyrosine, L-tryptophan, D-phenylalanine, D-tyrosine, and 5-Hydroxytryptophan. Solutions of NSAAs (50 or 100 mM) were made in 10-50 mM NaOH.

Library Generation

Error-prone PCR (EP-PCR) is the method of choice for introducing random mutations into a defined segment of DNA that is too long to be chemically synthesized as a degenerate sequence. EP-PCR was performed using the GeneMorph II Random Mutagenesis Kit (Stratagene Catalog #200550), following manufacturer instructions to obtain approximately an average of 2-4 DNA mutations per library member. To generate libraries of MjTyrRS-derived AARSs, roughly 175 ng of PCR template was used in each 25 uL of PCR mix containing primers that have roughly 40 base pairs of homology flanking the AARS coding region. The reaction mixture was subject to 30 cycles with Tm of 63° C. and extension time of 1 min. Four separate 25 uL EP-PCR reactions were performed per AARS and then pooled. Plasmid backbone PCRs were performed using KOD Xtreme Hot Start Polymerase (Millipore Catalog #71795). Both PCR products were isolated by 1.5% agarose gel electrophoresis and Gibson assembled in 8 parallel 20 uL volumes per library. Assemblies were pooled, washed by ethanol precipitation, and resuspended in 50 μL of dH$_2$O, which was drop dialyzed (EMD Millipore, Billerica, Mass.) and electroporated into E. cloni supreme cells (Lucigen, Middleton, Wis.). Libraries were expanded in culture and miniprepped (Qiagen, Valencia, Calif.) to roughly 100 ng/μl aliquots. 1 μg of library was drop dialyzed and electroporated into C321.ΔA.Nendint for subsequent FACS experiments. Colony counts on appropriate antibiotic containing plates within one doubling time after transformation revealed library sizes of roughly 1×10$^6$ for AARS libraries in Ecloni hosts and 1×10$^7$ in C321.ΔA.Nendint hosts.

Flow Cytometry and Cell Sorting

AARS libraries were subject to three rounds of fluorescence activated sorting in a Beckman Coulter MoFlo Astrios. Prior to each round, the usual NSAA incorporation assay procedure was followed such that cells would express GFP reporter proportional to the activity of the AARS library member. One notable deviation from that procedure was the use of a higher and variable inoculum volume to screen the full library at each stage. Cells displaying the top 0.5% of fluorescence activation (50 k cells) were collected after Round 1, expanded overnight, and used to inoculate experimental cultures for the next round. Because the next round was a negative screening round, the desired NSAA was not added into culture medium. The rest of the NSAA incorporation assay procedure was followed in order to eliminate cells that remained fluorescence due to promiscuous AARS activity on standard amino acids. In the second sort, cells displaying the lowest 10% of visible fluorescence (500 k cells) were collected. Cells passing the second round were expanded overnight and used to inoculate the third and final round of sorting. The experimental cultures for the third round were treated as the first round and were sorted for the upper 0.05% of fluorescence activation (1 k cells). The final cells collected were expanded overnight and plated for sequencing and downstream testing. Libraries were frozen at each stage before and after sorting. FlowJo X software was used to analyze the flow cytometry data. Constructs of interest were grown overnight, miniprepped, and transformed into C321.ΔA.Ubiq-UAG-sfGFP for further analysis in plate reader assays.

Reporter Purification

Strains harboring integrated GFP reporters and AARS/tRNA plasmids were inoculated from frozen stocks and grown to confluence overnight in 5 mL 2×YT containing chloramphenicol. Saturated cultures were used to inoculate 500 mL experimental cultures of 2×YT supplemented with chloramphenicol, arabinose, and appropriate NSAAs. Cultures were incubated at 34° C. to an OD$_{600}$ of 0.5-0.8 in a shaking incubator at 250 rpm. GFP expression was induced by addition of anhydrotetracycline, and cells were incubated at 34° C. for an additional 24 h before measurement. Cells were centrifuged in a Sorvall RC 5C Plus at 10,000 g for 20 minutes. Pellets were frozen at −20° C. before lysis and purification. Lysis of resuspended pellets was performed under denaturing conditions in 10 mL 7 M urea, 0.1 M Na$_2$PO$_4$, 0.01 M Tris-Cl, pH 8.0 buffer with 450 units of Benzonase (Novagen, cat. no. 70664-3) using 15 minutes of sonication in ice using a QSonica Q125 sonicator. Lysate was distributed into microcentrifuge tubes and centrifuged for 20 minutes at 20,000 g at room temperature, and then protein-containing supernatant was removed. 2 mL supernatant with 7.5 uM imidazole was added to 250 uL Ni-NTA resin (Qiagen Cat no. 30210) and equilibrated at 4° C. overnight. Columns were washed with 7×1 mL washes using 8 M urea, 0.1 M Na$_2$PO$_4$, 0.01 M Tris-Cl. Wash 1 and 2 were adjusted to pH 6.3 and contained no imidazole. Washes 3-7 were adjusted to pH 6.1 and contained imidazole at concentrations of 10 mM, 25 mM, 40 mM, 60 mM and 80 mM respectively. Protein was eluted with two 150 uL elutions using elution buffer (8 M urea, 0.1 M Na$_2$PO$_4$, 0.01 M Tris-Cl, pH 4.5, 300 mM imidazole). Gels demonstrated that wash 5 eluted the protein, and for several samples the wash 5 fraction was concentrated ~20× using Amicon Ultra 0.5 mL 10K spin concentrators. Protein gels were loaded with 30 uL wash or elution volumes along with 10 uL Nu-PAGE loading dye in Nu-PAGE 10% Bis-Tris Gels (ThermoFisher Cat. no NP0301). Protein gels were run at 180 V for 1 h, washed 3× with DI water, stained with coomassie (Invitrogen Cat. no LC6060) for one hour. Gels were destained overnight in water on a shaker at room temperature and images were taken with a BioRad ChemiDoc MP imaging system.

The contents of all references, patents and published patent applications cited throughout this application are hereby incorporated by reference in their entirety for all purposes.

EXAMPLE VI

Embodiments

The present disclosure provides a method of making a target polypeptide in a cell, wherein the target polypeptide includes a non-standard amino acid (NSAA) substitution at an amino acid target location, including genetically modifying the cell to express the target polypeptide including a non-standard amino acid substitution at an amino acid target location using an engineered amino-acyl tRNA synthetase and transfer RNA pair corresponding to the non-standard amino acid, and wherein the cell expresses the target polypeptide including a standard amino acid or undesired NSAA at the amino acid target location when the engineered amino-acyl tRNA synthetase and transfer RNA pair non-selectively adds the standard amino acid or undesired NSAA at the amino acid target location, wherein a removable protecting group is attached to the target polypeptide adjacent to the amino acid target location, such that when the removable protecting group is removed, an N-end amino acid is exposed at the amino acid target location. According to one aspect, the removable protecting group is a cleavable protecting group that is orthogonal within the cell. According to one aspect, the removable protecting group is an enzyme cleavable protecting group. According to one aspect, the removable protecting group is a protein that is cleavable by a corresponding enzyme. According to one aspect, the removable protecting group is ubiquitin that is cleavable by Ubp1. According to one aspect, the cell is genetically modified to include a foreign nucleic acid sequence encoding the target polypeptide including a non-standard amino acid substitution at an amino acid target location and a removable protecting group attached to the target polypeptide adjacent to the amino acid target location. According to one aspect, a detectable moiety is attached to the C-end of the target polypeptide. According to one aspect, a detectable moiety is attached to the C-end of the target polypeptide, wherein the detectable moiety is a fluorescent moiety. According to one aspect, a detectable moiety is attached to the C-end of the target polypeptide, wherein the detectable moiety is a reporter protein. According to one aspect, the cell is genetically modified to include a foreign nucleic acid sequence encoding the target polypeptide including a non-standard amino acid substitution at an amino acid target location, a removable protecting group attached to the target polypeptide adjacent to the amino acid target location and a detectable moiety attached to the C-end of the target polypeptide, wherein the nonstandard amino acid is encoded by a corresponding nonsense or sense codon. According to one aspect, the cell is genetically modified to include a foreign nucleic acid sequence encoding an amino-acyl tRNA synthetase and a transfer RNA corresponding to the nonstandard amino acid and wherein the nonstandard amino acid is provided to the cell and the cell expresses the synthetase and the transfer RNA to include the nonstandard amino acid at the amino acid target location. According to one aspect, the cell is genetically modified to include a foreign nucleic acid sequence encoding an enzyme for cleaving the removable protecting group under influence of a constitutive or an inducible promoter. According to one aspect, the cell includes an adapter protein that coordinates with a protease for degrading the target polypeptide when the N-end amino acid is a standard amino acid or an undesired NSAA. According to one aspect, the cell includes an adapter protein that coordinates with a protease for degrading the target polypeptide when the N-end amino acid is a standard amino acid or an undesired NSAA, wherein the adapter protein is under influence of a constitutive or an inducible promoter. According to one aspect, the method further includes the cell expressing an enzyme that cleaves the removable protecting group to generate an N-end amino acid. According to one aspect, the method further includes the cell expressing an enzyme that cleaves the removable protecting group to generate an N-end amino acid, and the cell expressing a protease wherein the protease degrades the target polypeptide when the N-end amino acid is a standard amino acid or an undesired NSAA. According to one aspect, the method further includes the cell expressing an enzyme that cleaves the removable protecting group to generate an N-end amino acid, and the cell expressing a protease wherein the protease degrades the target polypeptide when the N-end amino acid is a standard amino acid or an undesired NSAA to thereby enrich the target polypeptide including a non-standard amino acid substitution within the cell. According to one aspect, the method further includes the cell expressing an enzyme that cleaves the removable protecting group to generate an N-end amino acid, and the cell expressing an adapter protein that coordinates with a protease, wherein the protease degrades the target polypeptide when the N-end amino acid is a standard amino acid or an undesired NSAA. According to one aspect, the method further includes the cell expressing an enzyme that cleaves the removable protecting group to generate an N-end amino acid, and the cell expressing an adapter protein that coordinates with a protease, wherein the protease degrades the target polypeptide when the N-end amino acid is a standard amino acid or an undesired NSAA, and wherein the adapter protein is under influence of an inducible promoter. According to one aspect, the method further includes the cell expressing an enzyme that cleaves the removable protecting group to generate an N-end amino acid, and the cell expressing a ClpS-ClpAP protease system wherein the ClpS-ClpAP protease system degrades the target polypeptide when the N-end amino acid is a standard amino acid or an undesired NSAA to thereby enrich the target polypeptide including a desired non-standard amino acid substitution within the cell. According to one aspect, the method further includes the cell expressing an enzyme that cleaves the removable protecting group to generate an N-end amino acid, and the cell expressing a ClpS-ClpAP protease system wherein the ClpS-ClpAP protease system degrades the target polypeptide when the N-end amino acid is a standard amino acid or an undesired NSAA to thereby enrich the target polypeptide including a desired non-standard amino acid substitution within the cell, and wherein the ClpS protein is a natural homolog or a ClpS_V65I, ClpS_V43I, or ClpS_L32F, mutant. According to one aspect, the method further includes a detectable moiety is attached to the C-end of the target polypeptide and further including the cell expressing an enzyme that cleaves the removable protecting group to generate an N-end amino acid, and the cell expressing an adapter protein for a protease, wherein the protease degrades the target polypeptide when the N-end amino acid is a standard amino acid or an undesired NSAA to thereby enrich the target polypeptide including a desired non-standard amino acid substitution within the cell, and detecting the detectable moiety as a measure of the amount of the target polypeptide including a non-standard amino acid substitution within the cell. According to one aspect, the cell is a prokaryotic cell or a eukaryotic cell. According to one aspect, the cell is a microorganism such as a bacterium. According to one aspect, the cell is E. coli. According to one aspect, the cell is a genetically modified E. coli.

The disclosure provides a method of designing an amino acyl tRNA synthetase variant for preferential selection of a desired non-standard amino acid against its standard amino acid counterpart or undesired NSAAs for incorporation into a protein in a cell including genetically modifying the cell to express the target polypeptide including a non-standard amino acid substitution at an amino acid target location using an engineered amino-acyl tRNA synthetase and transfer RNA pair corresponding to the non-standard amino acid or undesired NSAA, and wherein the cell expresses the target polypeptide including a standard amino acid or undesired NSAA at the amino acid target location when the engineered amino-acyl tRNA synthetase and transfer RNA pair non-selectively adds the standard amino acid or undesired NSAA at the amino acid target location, wherein a removable protecting group is attached to the target polypeptide adjacent to the amino acid target location, such that when the removable protecting group is removed, an N-end amino acid is exposed at the amino acid target location, and wherein a detectable moiety is attached to the C-end of the target polypeptide, wherein the cell is genetically modified to include a foreign nucleic acid sequence encoding an amino-acyl tRNA synthetase and a transfer RNA corresponding to the nonstandard amino acid and wherein the nonstandard amino acid is provided to the cell and the cell expresses the synthetase and the transfer RNA to include the nonstandard amino acid at the amino acid target location, the cell expressing an enzyme that cleaves the removable protecting group to generate an N-end amino acid, and the cell expressing an adapter protein for a protease, wherein the protease degrades the target polypeptide when the N-end amino acid is a standard amino acid or undesired NSAA to thereby enrich the target polypeptide including a desired non-standard amino acid substitution within the cell, detecting the detectable moiety as a measure of the amount of the target polypeptide including a non-standard amino acid substitution within the cell, and repeatedly testing a modified synthetase in the genetically modified cell for improved production of the target polypeptide including a non-standard amino acid substitution.

The disclosure provides an engineered cell including a foreign nucleic acid sequence encoding a target polypeptide including a non-standard amino acid substitution at an amino acid target location and a removable protecting group attached to the target polypeptide adjacent to the amino acid target location.

The disclosure provides an engineered cell including a foreign nucleic acid sequence encoding a target polypeptide including a non-standard amino acid substitution at an amino acid target location, a removable protecting group attached to the target polypeptide adjacent to the amino acid target location and a detectable moiety attached to the C-end of the target polypeptide.

The disclosure provides an engineered cell including (a) a foreign nucleic acid sequence encoding a target polypeptide including a non-standard amino acid substitution at an amino acid target location, a removable protecting group attached to the target polypeptide adjacent to the amino acid target location and a detectable moiety attached to the C-end of the target polypeptide; (b) a foreign nucleic acid sequence encoding an amino-acyl tRNA synthetase and a transfer RNA corresponding to the nonstandard amino acid; (c) an adapter protein for a protease for degrading the target polypeptide having a standard amino acid or undesired NSAA as the N-end amino acid, wherein the adapter protein is under influence of a constitutive promoter or an inducible promoter.

The disclosure provides a nucleic acid construct encoding a target polypeptide including a non-standard amino acid substitution at an amino acid target location and a removable protecting group attached to the target polypeptide adjacent to the amino acid target location.

The disclosure provides a nucleic acid construct encoding a target polypeptide including a non-standard amino acid substitution at an amino acid target location, a removable protecting group attached to the target polypeptide adjacent to the amino acid target location and a detectable moiety attached to the C-end of the target polypeptide.

The disclosure provides a nucleic acid construct encoding adapter protein Clps or mutants or variants thereof.

The disclosure provides a nucleic acid construct encoding ClpS_V65I mutant.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

REFERENCES

1. M. Ibba, D. Söll, Aminoacyl-tRNAs: setting the limits of the genetic code. *Genes Dev.* 18, 731-8 (2004).
2. C. Noren, S. Anthony-Cahill, M. Griffith, P. Schultz, A general method for site-specific incorporation of unnatural amino acids into proteins. *Science* (80-.). 244 (1989) (available at http://science.sciencemag.org/content/244/4901/182).
3. L. Wang, A. Brock, B. Herberich, P. G. Schultz, Expanding the genetic code of *Escherichia coli. Science* (80-.). 292, 498-500 (2001).
4. J. W. Chin, Expanding and Reprogramming the Genetic Code of Cells and Animals. *Annu. Rev. Biochem.* 83, 379-408 (2014).
5. A. Dumas, L. Lercher, C. D. Spicer, B. G. Davis, Designing logical codon reassignment—Expanding the chemistry in biology. *Chem. Sci.* 6, 50-69 (2015).
6. R. A. Hughes, A. D. Ellington, Rational design of an orthogonal tryptophanyl nonsense suppressor tRNA. *Nucleic Acids Res.* 38, 6813-6830 (2010).
7. A. Chatterjee, H. Xiao, P.-Y. Yang, G. Soundararajan, P. G. Schultz, Genetic Codon Expansion A Tryptophanyl-tRNA Synthetase/tRNA Pair for Unnatural Amino Acid Mutagenesis in *E. coli***, doi:10.1002/anie.201301094.
8. J. W. Ellefson et al., Directed evolution of genetic parts and circuits by compartmentalized partnered replication. *Nat. Biotechnol.* 32, 97-101 (2014).
9. K. Oki, K. Sakamoto, T. Kobayashi, H. M. Sasaki, S. Yokoyama, Transplantation of a tyrosine editing domain into a tyrosyl-tRNA synthetase variant enhances its specificity for a tyrosine analog. *Proc. Natl. Acad. Sci. U.S.A* 105, 13298-303 (2008).
10. T. S. Young, I. Ahmad, J. A. Yin, P. G. Schultz, An Enhanced System for Unnatural Amino Acid Mutagenesis in *E. coli. J. Mol. Biol.* 395, 361-374 (2010).
11. A. K. Antonczak et al., Importance of single molecular determinants in the fidelity of expanded genetic codes. *Proc. Natl. Acad. Sci. U.S.A* 108, 1320-5 (2011).
12. S. Nehring, N. Budisa, B. Wiltschi, M. Oliveberg, N. Budisa, Performance Analysis of Orthogonal Pairs Designed for an Expanded Eukaryotic Genetic Code. *PLoS One.* 7, e31992 (2012).
13. J. W. Monk et al., Rapid and Inexpensive Evaluation of Nonstandard Amino Acid Incorporation in *Escherichia coli. ACS Synth. Biol.* (2016), doi:10.1021/acssynbio.6b00192.
14. J. Xie, W. Liu, P. G. Schultz, A Genetically Encoded Bidentate, Metal-Binding Amino Acid. *Angew. Chemie.* 119, 9399-9402 (2007).
15. D. J. Mandell et al., Biocontainment of genetically modified organisms by synthetic protein design. *Nature.* 518, 55-60 (2015).
16. C. Fan, J. M. L. Ho, N. Chirathivat, D. Soll, Y.-S. Wang, Exploring the Substrate Range of Wild-Type Aminoacyl-tRNA Synthetases. *ChemBioChem.* 15, 1805-1809 (2014).
17. L.-T. Guo et al., Polyspecific pyrrolysyl-tRNA synthetases from directed evolution. *Proc Natl Acad Sci USA.* 111, 16724-16729 (2014).
18. Y.-S. Wang et al., The de novo engineering of pyrrolysyl-tRNA synthetase for genetic incorporation of 1-phenylalanine and its derivatives. *Mol. Biosyst.* 7, 714-717 (2011).
19. N. Ostrov et al., Design, synthesis, and testing toward a 57-codon genome. *Science* (80-.). 353, 819-822 (2016).
20. D. B. F. Johnson et al., RF1 knockout allows ribosomal incorporation of unnatural amino acids at multiple sites. *Nat Chem Biol.* 7, 779-786 (2011).
21. P. O'Donoghue et al., Near-cognate suppression of amber, opal and quadruplet codons competes with aminoacyl-tRNAPyl for genetic code expansion. *FEBS Lett.* 586, 3931-3937 (2012).

22. A. Bachmair, D. Finley, A. Varshaysky, In vivo half-life of a protein is a function of its amino-terminal residue. *Science (80-.)*. 234, 179-186 (1986).
23. J. W. Tobias, T. E. Shrader, G. Rocap, A. Varshaysky, The N-end rule in bacteria. *Science (80-.)*. 254, 1374-1377 (1991).
24. T. Tasaki, S. M. Sriram, K. S. Park, Y. T. Kwon, The N-End Rule Pathway. *Annu. Rev. Biochem.* 81, 261-289 (2012).
25. K. H. Wang, R. T. Sauer, T. A. Baker, ClpS modulates but is not essential for bacterial N-end rule degradation. *Genes Dev.* 21, 403-8 (2007).
26. K. H. Wang, E. S. C. Oakes, R. T. Sauer, T. A. Baker, Tuning the Strength of a Bacterial N-end Rule Degradation Signal. *J. Biol. Chem.* 283, 24600-24607 (2008).
27. M. J. Lajoie et al., Genomically Recoded Organisms Expand Biological Functions. *Science (80-.)*. 342, 357-360 (2013).
28. M. Amiram et al., Evolution of translation machinery in recoded bacteria enables multi-site incorporation of nonstandard amino acids. *Nat Biotech.* 33, 1272-1279 (2015).
29. S. Million-Weaver, D. L. Alexander, J. M. Allen, M. Camps, in *Methods in molecular biology* (Clifton, N.J.) (2012; http://www.ncbi.nlm.nih.gov/pubmed/22144351), vol. 834, pp. 33-48.
30. J. W. Tobias, A. Varshaysky, Cloning and functional analysis of the ubiquitin-specific protease gene UBP1 of *Saccharomyces cerevisiae*. *J. Biol. Chem.* 266, 12021-8 (1991).
31. A. Wojtowicz et al., Expression of yeast deubiquitination enzyme UBP1 analogues in *E. coli. Microb. Cell Fact.* 4, 1-12 (2005).
32. G. Román-Hernández, J. Y. Hou, R. A. Grant, R. T. Sauer, T. A. Baker, The ClpS Adaptor Mediates Staged Delivery of N-End Rule Substrates to the AAA+ ClpAP Protease. *Mol. Cell.* 43, 217-228 (2011).
33. K. H. Wang, G. Roman-Hernandez, R. A. Grant, R. T. Sauer, T. A. Baker, The Molecular Basis of N-End Rule Recognition. *Mol. Cell.* 32, 406-414 (2008).
34. F. J. LaRiviere, A. D. Wolfson, 0. C. Uhlenbeck, Uniform Binding of Aminoacyl-tRNAs to Elongation Factor Tu by Thermodynamic Compensation. *Science (80-.)*. 294 (2001).
35. J. M. Schrader, S. J. Chapman, 0. C. Uhlenbeck, Understanding the Sequence Specificity of tRNA Binding to Elongation Factor Tu using tRNA Mutagenesis. *J. Mol. Biol.* 386, 1255-1264 (2009).
36. Taraka Dale, and Lee E. Sanderson, 0. C. Uhlenbeck*, The Affinity of Elongation Factor Tu for an Aminoacyl-tRNA Is Modulated by the Esterified Amino Acid† (2004), doi:10.1021/BI036290O.
37. S.-J. Chen, X. Wu, B. Wadas, J.-H. Oh, A. Varshaysky, An N-end rule pathway that recognizes proline and destroys gluconeogenic enzymes. *Science (80-.)*. 355 (2017).
38. L. Wang, Z. Zhang, A. Brock, P. G. Schultz, Addition of the keto functional group to the genetic code of *Escherichia coli. Proc. Natl. Acad. Sci. U.S.A* 100, 56-61 (2003).
39. J. W. Chin et al., Addition of p-Azido-1-phenylalanine to the Genetic Code of *Escherichia coli. J. Am. Chem. Soc.* 124, 9026-9027 (2002).
40. † Lei Wang, ‡ and Ansgar Brock, ‡§ Peter G. Schultz*, Adding 1-3-(2-Naphthyl)alanine to the Genetic Code of *E. coli* (2002), doi:10.1021/JA012307J.
41. D. G. Gibson et al., Enzymatic assembly of DNA molecules up to several hundred kilobases. *Nat. Methods.* 6, 343-345 (2009).
42. H. M. Salis, E. A. Mirsky, C. A. Voigt, Automated design of synthetic ribosome binding sites to control protein expression. *Nat Biotech.* 27, 946-950 (2009).
43. A. M. Kunjapur, Y. Tarasova, K. L. J. Prather, Synthesis and Accumulation of Aromatic Aldehydes in an Engineered Strain of *Escherichia coli. J. Am. Chem. Soc.* 136, 11644-11654 (2014).
44. K. A. Datsenko, B. L. Wanner, One-step inactivation of chromosomal genes in *Escherichia coli* K-12 using PCR products. *Proc Natl Acad Sci USA.* 97, 6640-6645 (2000).
45. D. Yu et al., An efficient recombination system for chromosome engineering in *Escherichia coli. Proc. Natl. Acad. Sci. U.S.A* 97, 5978-83 (2000).
46. J. A. DeVito, Recombineering with tolC as a Selectable/Counter-selectable Marker: remodeling the rRNA Operons of *Escherichia coli. Nucleic Acids Res.* 36, e4 (2008).
47. C. J. Gregg et al., Rational optimization of tolC as a powerful dual selectable marker for genome engineering. *Nucleic Acids Res.* 42, 4779-4790 (2014).
48. H. H. Wang et al., Programming cells by multiplex genome engineering and accelerated evolution. *Nature.* 460, 894-898 (2009).
49. F. J. Isaacs et al., Precise manipulation of chromosomes in vivo enables genome-wide codon replacement. *Science (80-.)*. 333, 348-353 (2011).
50. F. St-Pierre et al., One-step cloning and chromosomal integration of DNA. *ACS Synth. Biol.* 2, 537-541 (2013).
51. A. M. A. M. Kunjapur, J. C. J. C. Hyun, K. L. J. K. L. J. Prather, Deregulation of S-adenosylmethionine biosynthesis and regeneration improves methylation in the *E. coli* de novo vanillin biosynthesis pathway. *Microb. Cell Fact.* 15, 1 (2016).

The invention claimed is:

1. A method of degrading polypeptides expressed by a cell from a first foreign nucleic acid sequence encoding a polypeptide including a target nonstandard amino acid (NSAA) at an amino acid target location and a removable protecting group at the N-terminal end of the polypeptide, wherein the cell includes a second foreign nucleic acid sequence encoding an engineered amino-acyl tRNA synthetase and transfer RNA pair corresponding to the target non-standard amino acid, comprising
expressing the first and second nucleic acid sequences to produce (1) a polypeptide with the target NSAA at the amino acid target location and with the removable protecting group at the N-terminal end of the polypeptide, and one or more of (2) a polypeptide with a nontarget NSAA at the amino acid target location and with the removable protecting group at the N-terminal end of the polypeptide, or (3) a polypeptide with a standard amino acid at the amino acid target location and with the removable protecting group at the N-terminal end of the polypeptide,
removing the removable protecting group from the polypeptides, such that an N-terminal end amino acid is exposed at the amino acid target location of the polypeptides, and
degrading one or more of the polypeptide with the nontarget NSAA at the amino acid target location and the polypeptide with the standard amino acid at the amino acid target location using a Colipase (ClpS)-Colipase ATP-dependent (ClpS-ClpAP) protease system, and wherein the ClpS is a protein having the amino acid sequence of SEQ ID NO:149 with a V43I mutation or a L32F mutation.

2. The method of claim 1 wherein the removable protecting group is a protein that is cleavable by a corresponding enzyme.

3. The method of claim 1 wherein the removable protecting group is ubiquitin that is cleavable by ubiquitin-specific protease 1 (Ubp1).

4. The method of claim 1 wherein a detectable moiety is attached to the C-terminal end of the polypeptides.

5. The method of claim 1 wherein a detectable moiety is attached to the C-terminal end of the polypeptides, wherein the detectable moiety is a fluorescent moiety.

6. The method of claim 1 wherein a detectable moiety is attached to the C-terminal end of the polypeptides, wherein the detectable moiety is a reporter protein.

7. The method of claim 1 wherein the nonstandard amino acid is encoded by a corresponding nonsense or sense codon.

8. The method of claim 1 wherein the cell is genetically modified to include a foreign nucleic acid sequence encoding an enzyme for cleaving the removable protecting group under influence of a constitutive or an inducible promoter.

9. The method of claim 1 wherein expression of ClpS is upregulated.

10. The method of claim 1 wherein expression of ClpS is under influence of a constitutive or an inducible promoter.

11. The method of claim 1 wherein a detectable moiety is attached to the C-terminal end of the polypeptides and further comprising detecting the detectable moiety as a measure of the amount of the polypeptide including the non-standard amino acid within the cell.

12. The method of claim 1 wherein the cell is a prokaryotic cell or a eukaryotic cell.

13. The method of claim 1 wherein the cell is a bacterium.

14. The method of claim 1 wherein the cell is a genetically modified *E. coli*.

15. An engineered cell comprising
(a) a first foreign nucleic acid sequence encoding a polypeptide including a target non-standard amino acid (NSAA) at an amino acid target location, a removable protecting group attached to the polypeptide adjacent to the amino acid target location and a detectable moiety attached to the C-terminal end of the polypeptide;
(b) a second foreign nucleic acid sequence encoding an amino-acyl tRNA synthetase and a transfer RNA corresponding to the target nonstandard amino acid; and
(c) a third nucleic acid sequence encoding a Colipase (ClpS)-Colipase ATP-dependent (ClpS-ClpAP) protease system, wherein the ClpS is under influence of a constitutive promoter or an inducible promoter and wherein the ClpS is a protein having the amino acid sequence of SEQ ID NO:149 with a V43I mutation or a L32F mutation.

16. An engineered cell comprising a nucleic acid construct encoding a Colipase (ClpS) protein having the amino acid sequence of SEQ ID NO:149 with a V43I mutation or a L32F mutation.

17. A nucleic acid construct encoding a polypeptide including a non-standard amino acid at an amino acid target location, a removable protecting group attached to the polypeptide adjacent to the amino acid target location and a detectable moiety attached to the C-terminal end of the polypeptide, and a Colipase (ClpS) protein having the amino acid sequence of SEQ ID NO:149 with a V43I mutation or a L32F mutation.

18. A nucleic acid construct encoding a Colipase (ClpS) protein having the amino acid sequence of SEQ ID NO:149 with a V43I mutation or a L32F mutation.

* * * * *

SEQUENCE LISTING

<160> NUMBER OF SEQ ID NOS: 160

<210> SEQ ID NO 1
<211> LENGTH: 7
<212> TYPE: PRT
<213> ORGANISM: Tobacco etch virus

<400> SEQUENCE: 1

Met Glu Asn Leu Tyr Phe Gln
1               5

<210> SEQ ID NO 2
<211> LENGTH: 6

```
<212> TYPE: PRT
<213> ORGANISM: Tobacco etch virus

<400> SEQUENCE: 2

Glu Asn Leu Tyr Phe Gln
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Phe Val Gln Glu Leu
1               5

<210> SEQ ID NO 5
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcagattt ttgtgaagac tttaacaggt aagacgatta ccctggaggt ggagtcctcg      60
gacaccatcg ataatgtaaa atcaaaaatc aagataagg aaggaatccc tccagaccag      120
caacgtctga ttttcgcagg taaacaactg gaggatggtc gcacgctttc ggactacaac     180
atccagaaag aatctaccct tcatttggtt ctgcgtctgc gtggaggata gttgtttgtg     240
caggagcttg catccaaggg cgaggagctc tttactggcg tagtaccaat tctcgtagag     300
ctcgatggcg atgtaaatgg ccataagttt tccgtacgcg gcgagggcga gggcgatgca     360
actaacggca agctcactct caagtttatt tgtactactg gcaagctccc agtaccatgg     420
ccaactctcg taactactct gacctatggc gtacaatgtt tttcccgcta tccagatcac     480
atgaagcaac atgatttttt taagtccgca atgccagagg gctatgtaca agagcgcact     540
attagcttta aggatgatgg cacctataag actcgcgcag aggtaaagtt tgagggcgat     600
actctcgtaa atcgcattga gctcaagggc attgattta aggaggatgg caatattctc     660
ggccataagc tggagtataa tttcaattcc cataatgtat acattaccgc agataagcaa     720
aagaatggca ttaaggcgaa ttttaagatt cgccataatg tggaggatgg ctccgtacaa     780
ctcgcagatc attatcaaca aaatactcca attggcgatg cccagtact cctcccagat      840 aatcattatc tctccactca atccgtgctc tccaaagatc caaatgagaa gcgcgatcac     900
atggtactcc tggagtttgt aactgcagca ggcattactc atggcatgga tgagctctat     960
```
aagctcgagc accaccacca ccaccactaa                                         990

<210> SEQ ID NO 6
<211> LENGTH: 312
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgtctgata gtcctgttga cttaaaaccc aagcctaaag tcaagcccaa attagaacgc         60
ccaaaacttt acaaagtcat gttattgaat gatgattata caccacgcga atttgtgacg        120
gtagtcctta aagcggtgtt tcgtatgtca gaggacactg gtcgccgtgt aatgatgaca        180
gcacatcgtt ttggttcggc ggtggtggtc gtttgtgaac gtgacattgc agagacgaaa        240
gccaaggagg cgaccgactt ggggaaggaa gcaggttttc ctttgatgtt cacgactgag        300
cccgaggagt aa                                                            312

<210> SEQ ID NO 7
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gttatgcact acgatggtgt tgacgtttac gttggtggta tggaacagcg taaaatccac         60
atgctggcgc gtgaactgct gccgaaaaaa gttgtttgca tccacaaccc ggttctgacc        120
ggtctggacg gtgaaggtaa aatgtcttct tctaaaggta acttcatcgc ggttgacgac        180
tctccggaag aaatccgtgc gaaaatcaaa aaagcgtact gcccggcggg tgttgttgaa        240
ggtaacccga tcatggaaat cgcgaaatac ttcctggaat accgctgac catcaaaggt        300

<210> SEQ ID NO 8
<211> LENGTH: 2151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggggagtg ggtctttcat tgctgggctt gtcaacgatg gtaatacgtg ttttatgaac         60
tcggttcttc agtcccttgc tagtagccgt gaacttatgg agttttggga taataatgta        120
atccgtacat atgaagaaat tgaacagaac gagcacaatg aggaaggtaa tggccaagag        180
agcgcacaag atgaggcaac tcacaaaaaa acactcgca agggaggtaa ggtctatggg        240
aagcataaaa agaaattaaa ccgcaaatct tctagcaagg aagacgaaga aaagtcgcaa        300
gaaccagaca ttacgttttc ggtggcgttg cgtgatctgc tgagcgcatt aaatgctaag        360
tattatcgcg acaaacccta ctttaagact aactctttat aaaagcgat gagcaagtcc         420 ccgcgcaaaa atatcttgct tgggtacgat caagaagacg ctcaggaatt ttttcaaaac        480
attcttgcgg agttagaatc taatgtcaag tcgttaaaca cagaaaagct tgatactaca        540
ccggtagcca gtccgaact tccagacgat gctctggttg gccaattaaa ccttggtgag         600
gtaggcaccg tgtacattcc cacagaacaa attgacccca ttcgattttt acatgacaaa        660

```
tcgattcaaa actttacccc ctttaaactg atgaccccgt tggatgggat cacggctgag    720
cgcatcggct gcctgcaatg cggagagaac gggggaattc gctacagtgt tttcagcgga    780
ttaagtttga acctgccgaa tgaaaatatt ggaagcactc ttaaactgtc ccagttactg    840
tccgattggt cgaaacccga gattatcgag ggtgttgaat gcaaccgttg cgctttaaca    900
gctgcgcact cacacttgtt tggccaatta aaggagtttg agaagaaacc tgaaggctcg    960
attcccgaaa aacttattaa tgccgtaaag gaccgcgtgc accagatcga agaggtcttg   1020
gcaaagccgg ttatcgacga tgaagattat aaaaaattgc atactgcgaa tatggtccgc   1080
aagtgttcaa aaagtaaaca aattcttatc tctcgtccac cacctttgtt gtctattcat   1140
atcaaccgct ctgttttcga cccgcgcacc tacatgattc gcaagaacaa ctccaaggtt   1200
ttgttcaagt cacgcttgaa cctggcaccc tggtgctgtg atatcaacga aatcaatctt   1260
gacgcacgcc ttccgatgtc gaagaaggaa aaagcagctc aacaagattc ttctgaagac   1320
gagaacattg gcggagagta ctatactaaa ttgcatgaac gttttgagca ggagtttgaa   1380
gattctgaag aagagaagga atacgatgat gcagagggta attatgcatc gcattataac   1440
cataccaagg acatctccaa ctacgatcca ttgaatggag aagtcgacgg tgtgacttcc   1500
gatgatgagg atgaatacat tgaagagaca gacgcgttgg ggaataccat caaaaaacgt   1560
attattgaac actccgacgt ggagaacgaa aacgtgaagg ataatgaaga acttcaggag   1620
atcgataacg ttagcttgga tgagccaaaa attaatgtcg aggaccagct tgaaacgagt   1680
tctgatgagg aagacgttat tcctgctcca cccatcaact acgctcgcag ctttagtacg   1740
gtcccagcga cccctttaac ttactctttg cgcagcgtca tcgtgcacta tgggactcac   1800
aactacggac attatattgc atttcgcaag tatcgtggat gttggtggcg catctccgat   1860
gagacggtct atgtggtaga tgaggccgaa gtactgtcaa caccgggggt atttatgctt   1920
ttctacgagt atgatttcga cgaggagacc ggaaaaatga agacgactt agaagctatc   1980
cagagcaata atgaggaaga tgacgagaaa gaacaggaac agaagggtgt ccaggagcca   2040
aaagaatccc aggagcaagg cgaaggcgaa gaacaagaag aagggcaaga gcaaatgaaa   2100
tttgagcgta cggaggatca tcgcgacatt tcagggaagg atgtgaatta a           2151
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 9
ccattattat catgacatta acc                                              23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 10
ggatttgtcc tactcaggag                                                  20

<210> SEQ ID NO 11
<211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 cttttatcg caactctc                                                         18

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttaaagagga gaaattaact atgcagattt ttgtgaagac t                               41

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agctcctcgc ccttggatgc aagctcctgc acaaacaagt                                 40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagggaagga tgtgaattaa taagtcgacc atcatcatca                                 40

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atgaaagacc cactccccat agatctaatt cctcctgtta gc                              42

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
taacaggagg aattagatct atggggagtg ggtctttcat                                 40

<210> SEQ ID NO 17
<211> LENGTH: 40
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 17
tcaagcgtga cttgaacaaa accttggagt tgttcttgcg                              40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgcaagaaca actccaaggt tttgttcaag tcacgcttga                              40

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgatgatgat ggtcgactta ttaattcaca tccttccctg a                            41

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcgtctgcg tggaggatag ttgtttgtgc aggagcttgc                              40

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aagctcctgc acaaacaact atcctccacg cagacgc                                 37

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcttgggtac gatcaagaag                                                    20

<210> SEQ ID NO 23
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 23
ccttggtatg gttataatgc g                                              21

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cagggaagga tgtgaattaa aagcttgatg ggggatccca                          40

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atgaaagacc cactccccat ggtacctttc tcctctttaa tgaat                    45

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttaaagagga gaaggtacc atggggagtg ggtctttcat                           40

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgggatcccc catcaagctt ttaattcaca tccttccctg a                        41

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taaagaggag aaaggtacca tgcagatttt tgtgaagact ttaac                    45

<210> SEQ ID NO 29
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 29
tgggatcccc catcaagctt ttagtggtgg tggtggtggt                            40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
accaccacca ccaccactaa aagcttgatg ggggatccca                            40

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtcttcacaa aaatctgcat ggtacctttc tcctctttaa tgaat                      45

<210> SEQ ID NO 32
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttacgggcta attacaggca gaaatgcgtg atgtgtgcca cacttgttga tccctatcag      60
tgatagagat tgac                                                       74

<210> SEQ ID NO 33
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccagcgggct aactttcctc gccggaagag tggttaacaa aatagtaacg tcaccgacaa      60
acaacagata aaac                                                       74

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaaagtgag ttgagtataa c                                               21

<210> SEQ ID NO 35
<211> LENGTH: 20
```

<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 35
tttctcctta ttatcaatgc                                              20

<210> SEQ ID NO 36
<211> LENGTH: 90
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 36
gccgcagcaa gccaaagtga gttgagtata acgcaaattt gctactggtc cgatgggtgc    60
aatggtctga attacgggct aattacaggc                                    90

<210> SEQ ID NO 37
<211> LENGTH: 88
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 37
aacgcaatcg caaccgctaa accactggcc atgtgcacga gtttcattca tttctcctta    60
ttatcaatgc accagcgggc taactttc                                      88

<210> SEQ ID NO 38
<211> LENGTH: 90
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 38
taaagagctc ctcgcccttg gatgcaagct cctgcacaaa caacgatcct ccacgcagac    60
gcagaaccaa atgaagggta gattctttct                                    90

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 39
cgtctgcgtg gaggatc                                                  17

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 40
cgtctgcgtg gaggata                                                 17

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttctgaccca tcgtaattaa aagcttgatg ggggatccca                         40

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tggtatatct cctttatta ttaattcaca tccttccctg aaat                     44

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtgaattaat aataaaagga gatataccat gtcatacagc ggcga                   45

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgggatcccc catcaagctt ttaattacga tgggtcagaa tcg                     43

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctgccaactt actgatttag tgtatgatgg tgtttttgag g                      41

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gccgcttagt tagccgtgca aacttatatc gtatggggct g                      41

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agccccatac gatataagtt tgcacggcta actaagcggc                                40

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ctcaaaaaca ccatcataca ctaaatcagt aagttggcag catca                          45

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tgtgtacgct agaaaaagcc taaaagcttg atgggggatc                                40

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gttcgtttta cccatggtat atctcctttt attattaatt cacat                          45

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ataataaaag gagatatacc atgggtaaaa cgaacgactg                                40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gatcccccat caagctttta ggcttttttct agcgtacaca                               40

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tactgtttct ccatacccgt tttttgggc taacaggagg aattagatct            50

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agatctaatt cctcctgtta gcc                                        23

<210> SEQ ID NO 55
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
accccatgag tgcaatagaa aatttcgacg cccatacgcc catgatgcag cagtgatagt    60
cgctgaaagc ccagcatccc gagatcctgc                                    90

<210> SEQ ID NO 56
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
accccatgag tgcaatagaa aatttcgacg cccatacgcc catgatgcag cagtatctca    60
ggctgaaagc ccagcatccc gagatcctgc                                    90

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ccatgatgca gcagtatctc ag                                         22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccatgatgca gcagtgatag tc                                          22

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aggttgtcct gacgctcctg                                             20

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtataatttc aattcccata atgtatag                                    28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtataatttc aattcccata atgtatac                                    28

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctcgagctta tagagctcat c                                           21

<210> SEQ ID NO 63
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cttaaaattc gccttaatgc cattcttttg cttatctgcg gtaatgtata cattatggga   60
attgaaatta tactccagct tatggccgag                                   90

<210> SEQ ID NO 64
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 cttttcttc cgccagttga tcaaagtcca gccagtcgtt ctattatcac attgtcagtt    60
atcatcttcg gttacggtta tcggcagaac                                     90

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccgataaccg taaccgaaga tgataactga caatgg                              36

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccgataaccg taaccgaaga tgataactga caatgt                              36

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cgtacttgtt caccatcgcc actttggt                                       28

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cgactgagcc cgaggagtaa aagcttgatg ggggatccca                          40

<210> SEQ ID NO 69
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tcaacaggac tatcagacat ggtatatctc cttttattat taattcacat cc            52

<210> SEQ ID NO 70
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ataataaaag gagatatacc atgtctgata gtcctgttga ctt                43

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgggatcccc catcaagctt ttactcctcg ggctcagtcg                    40

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atgatgatta cactccggcg gagtttgtta ttgacgtgt                     39

<210> SEQ ID NO 73
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cgtcaataac aaactccgcc ggagtgtaat catcattgac                    40

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
taacctaaac tgacaggcat                                          20

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ttccgatccc caattcct                                            18

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggatcatttt gcgcttcag                                                19

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gaatataacc tttcattccc                                               20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtgtttcgac tagcatttc                                                19

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggtcaaacat gatttcaaaa ac                                            22

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
caacagtact gcgatgag                                                 18

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcaaataagc tcttgtcagc                                               20

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (21)..(21)
<223> OTHER INFORMATION: a, c, t, g, unknown or other

<400> SEQUENCE: 82
catctatgta taaagtgata ntcgtcaatg atgattacac tccg         44

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tatcacttta tacatagatg                                    20

<210> SEQ ID NO 84
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 84
attacactcc gatggagttt nttattgacg tgttacaaaa attc          44

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaactccatc ggagtgtaat                                    20

<210> SEQ ID NO 86
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 86
caacgcaatt gatgctcgct nttcactacc aggggaagg               39

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agcgagcatc aattgcgttg                                    20
```

<210> SEQ ID NO 88
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 88
cgagggagaa tgagcatcca ntcctgtgta cgctagaaaa agc               43

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tggatgctca ttctccctcg                                         20

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcggatttgt cctactcag                                          19

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gctaacagga ggaattagat ct                                      22

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ttgataatct aacaaggatt atggg                                   25

<210> SEQ ID NO 93
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cccataatcc ttgttagatt atcaaaggca ttttgctatt aaggg     45

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agatctaatt cctcctgtta gc     22

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
taactcgagg ctgttttgg     19

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
catatgtata tctccttgtg catc     24

<210> SEQ ID NO 97
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gatgcacaag gagatataca tatggggagt gggtctttca t     41

<210> SEQ ID NO 98
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ccaaaacagc ctcgagttag gctttttcta gcgtaca     37

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
acccgatcat gcaggttaac gttatgcact acgatggtgt                          40

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcaccaccga atttttccgg acctttgatg gtcagcg                             37

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccggaaaaat tcggtggtga                                                20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gttaacctgc atgatcgggt                                                20

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
acgctctcct gagtaggac                                                 19

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tcaccgacaa acaacagata aaac                                           24

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tatctgttgt ttgtcggtga acgtctcatt ttcgccagat                                40

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtcctactca ggagagcgta gtgtcaactt tatggctagc                                40

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cgacctgaat ggaagcc                                                         17

<210> SEQ ID NO 108
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
catacacggt gcctgac                                                         17

<210> SEQ ID NO 109
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aacgcagtca ggcaccgtgt atggagaaaa aaatcactgg atatac                         46

<210> SEQ ID NO 110
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gccggcttcc attcaggtcg aaaaaattac gccccgc                                   37

<210> SEQ ID NO 111
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, t, g, unknown or other

```
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other

<400> SEQUENCE: 111
caaaatgctg gatttgatat aattatannk ttgnnkgatt tannkgccta tttaaaccag      60
aaaggagag                                                             69

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tataattata tcaaatccag cattttgtaa atc                                  33

<210> SEQ ID NO 113
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 113
ggcaaaatat gtttatggaa gtgaannknn kcttgataag gatnnkacac tgaatgtcta     60
tagattggc                                                             69

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ttcacttcca taaacatatt ttgcc                                           25

<210> SEQ ID NO 115
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
```

```
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other

<400> SEQUENCE: 115
gaagttatct atccaataat gnnkgttnnk ggtgctcatn nkcttggcgt tgatgttgca      60
g                                                                     61

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cattattgga tagataactt cagcaac                                          27

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cgcatcaggc aatttagc                                                   18

<210> SEQ ID NO 118
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cgcgcgtgaa gacgaaaacc agaaagttgc ggaagttatc tac                       43

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggttttcgtc ttcacgcg                                                   18

<210> SEQ ID NO 120
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
```
tacccgatca tgcaggttaa aggtatccac tacaaggtg ttg                43

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ttaacctgca tgatcgggta                                         20

<210> SEQ ID NO 122
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtaaaatcca catgctggcg tgtgaactgc tgccgaaa                     38

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cgccagcatg tggatttta                                          19

<210> SEQ ID NO 124
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tcctggaata cccgctgacc ttcaaacgtc cggaaaaatt c                 41

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggtcagcggg tattccag                                           18

<210> SEQ ID NO 126
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gctgaccatc aaacgtccgg taaaattcgg tggtgacctg                   40

```
<210> SEQ ID NO 127
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ccggacgttt gatggtc                                                    17

<210> SEQ ID NO 128
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tcaaaaacaa agaactgcac tcgatgcgtc tgaaaaacg                             39

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gtgcagttct ttgttttga ac                                               22

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ctgcagtttc aaacgctaaa ttg                                             23

<210> SEQ ID NO 131
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
taggcctgat aagcgtagcg catcaggcaa tttagcgttt gaaactgcag                 50

<210> SEQ ID NO 132
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aatacccgct gaccatcaaa cgtccggaaa aattcggtg                             39
```

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
accaccgaat ttttccggac gtttgatggt cagcgggtat                               40

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcgaaatacg tttacggttc                                                    20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gaaccgtaaa cgtatttcgc                                                    20

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggacggtgaa ggtaaaatgt c                                                  21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gacattttac cttcaccgtc c                                                  21

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
cggcgccagg gttgtttttc acgctctcct gagtaggaca                              40

<210> SEQ ID NO 139
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ttccattcag gtcgaaaaaa agtgtcaact ttatggctag c                41

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140 tttttcgac ctgaatggaa gc                                      22

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gaaaaacaac cctggcgc                                          18

<210> SEQ ID NO 142
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ttccattcag gtcgaaaaaa ctcgaggtga agacgaaagg                  40

<210> SEQ ID NO 143
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
acatttcagg gaaggatgtg aattaataat aaaaggagat atacc            45

<210> SEQ ID NO 144
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gcgtaccatg ggatccccca tcaagctttt a                           31

<210> SEQ ID NO 145

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
taaaagcttg atgggggatc                                                  20

<210> SEQ ID NO 146
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ggtatatctc cttttattat taattcacat cc                                    32

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggatcatcgc gacatttc                                                    18

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
taataaaagg agatatacc                                                   19

<210> SEQ ID NO 149
<211> LENGTH: 106
<212> TYPE: PRT
<213> ORGANISM: Escherichia coli

<400> SEQUENCE: 149
```

Met Gly Lys Thr Asn Asp Trp Leu Asp Phe Asp Gln Leu Ala Glu Glu
1               5                   10                  15

Lys Val Arg Asp Ala Leu Lys Pro Pro Ser Met Tyr Lys Val Ile Leu
            20                  25                  30

Val Asn Asp Asp Tyr Thr Pro Met Glu Phe Val Ile Asp Val Leu Gln
        35                  40                  45

Lys Phe Phe Ser Tyr Asp Val Glu Arg Ala Thr Gln Leu Met Leu Ala
    50                  55                  60

Val His Tyr Gln Gly Lys Ala Ile Cys Gly Val Phe Thr Ala Glu Val
65                  70                  75                  80

Ala Glu Thr Lys Val Ala Met Val Asn Lys Tyr Ala Arg Glu Asn Glu
                85                  90                  95

His Pro Leu Leu Cys Thr Leu Glu Lys Ala
            100                 105

```
<210> SEQ ID NO 150
<211> LENGTH: 99
<212> TYPE: PRT
<213> ORGANISM: Corynebacterium glutamicum

<400> SEQUENCE: 150
```

Met Ser Ser Pro Ser Ala Pro Leu Ala Thr Pro Asp Val Glu Leu Asp
1               5                   10                  15

Val His Thr Leu Ser Ser Glu Asn Leu Pro Trp Leu Cys Ile Val Trp
                20                  25                  30

Asp Asp Pro Val Asn Leu Met Ser Tyr Val Thr Tyr Val Phe Gln Thr
            35                  40                  45

Val Leu Gly Phe Ser Lys Lys Arg Ala Thr Glu Leu Met Met Gln Val
    50                  55                  60

His Thr Glu Gly Lys Ala Val Val Ser Ser Gly Glu Lys Asp Lys Val
65                  70                  75                  80

Glu Gly Asp Val Lys Lys Leu His Thr Ala Gly Leu Trp Ala Thr Met
                85                  90                  95

Gln Gln Ala

```
<210> SEQ ID NO 151
<211> LENGTH: 94
<212> TYPE: PRT
<213> ORGANISM: Streptomyces coelicolor

<400> SEQUENCE: 151
```

Met Glu Ile Glu Lys Thr Glu Ser Ala Glu Glu Val Phe Ala Val Pro
1               5                   10                  15

Glu Pro Asp Val Pro Trp Val Thr Ile Val His Asn Asp Pro Val Asn
                20                  25                  30

Leu Met Ser Tyr Val Thr Tyr Val Phe Gln Ser Tyr Phe Gly Tyr Ser
            35                  40                  45

Lys Asp Lys Ala Thr Lys Leu Met Met Asp Val His His Lys Gly Arg
    50                  55                  60

Ala Val Val Ser Ser Gly Ser Arg Glu Glu Met Glu Arg Asp Val Gln
65                  70                  75                  80

Ala Met His Gly Tyr Gly Leu Trp Ala Thr Leu Gln Gln Asp
                85                  90

```
<210> SEQ ID NO 152
<211> LENGTH: 106
<212> TYPE: PRT
<213> ORGANISM: Vibrio cholerae

<400> SEQUENCE: 152
```

Met Ser Lys Asn Phe Glu Trp Ile Ser Pro Asp Phe Asp Leu Leu Glu
1               5                   10                  15

Lys Glu Lys Thr Ala Val Lys Pro Pro Ser Met Tyr His Val Val Leu
                20                  25                  30

Asn Asn Asp Asp Tyr Thr Pro Met Asp Phe Val Ile Glu Ile Leu Glu
            35                  40                  45

Arg Phe Phe Ser Met Asp Ile Glu Arg Ala Thr Gln Val Met Leu Lys
    50                  55                  60

Val His Tyr Glu Gly Lys Ala Ile Cys Gly Thr Phe Thr Ala Glu Val
65                  70                  75                  80

Ala Glu Thr Lys Val Ala Gln Val Thr Met Tyr Ser Arg Glu Asn Glu
                85                  90                  95

-continued

His Pro Leu Leu Cys Thr Met Glu Gln Ala
            100                 105

<210> SEQ ID NO 153
<211> LENGTH: 109
<212> TYPE: PRT
<213> ORGANISM: Caulobacter vibrioides

<400> SEQUENCE: 153

Met Ala Glu Arg Lys Gln Gly Gly Gln Gly Asn Gly Val Gly Ser Ser
1               5                   10                  15

Val Val Thr Glu Val Lys Pro Lys Thr Gln Lys Pro Ser Leu Tyr Arg
            20                  25                  30

Val Leu Ile Leu Asn Asp Asp Tyr Thr Pro Met Glu Phe Val Val Tyr
        35                  40                  45

Val Leu Glu Arg Phe Phe Asn Lys Ser Arg Glu Asp Ala Thr Arg Ile
    50                  55                  60

Met Leu His Val His Gln Asn Gly Val Gly Val Cys Gly Val Tyr Thr
65                  70                  75                  80

Tyr Glu Val Ala Glu Thr Lys Val Ala Gln Val Ile Asp Ser Ala Arg
                85                  90                  95

Arg His Gln His Pro Leu Gln Cys Thr Met Glu Lys Asp
            100                 105

<210> SEQ ID NO 154
<211> LENGTH: 98
<212> TYPE: PRT
<213> ORGANISM: Synechocystis sp.

<400> SEQUENCE: 154

Met Ile Ser Asn Ala Ala Thr Ser Thr Pro Asp Arg Leu Thr Ser Thr
1               5                   10                  15

Val Arg Lys Thr Tyr Pro Asn Phe Lys Val Ile Val Leu Asn Asp Asp
            20                  25                  30

Phe Asn Thr Phe Gln His Val Ser Asp Cys Leu Leu Lys Tyr Ile Pro
        35                  40                  45

Gly Met Thr Gly Asp Arg Ala Trp Glu Leu Thr Asn Gln Val His Phe
    50                  55                  60

Asp Gly Leu Ala Ile Val Trp Val Gly Pro Gln Glu Gln Ala Glu Leu
65                  70                  75                  80

Tyr His Gln Gln Leu Arg Arg Glu Gly Leu Thr Met Ala Pro Leu Glu
                85                  90                  95

Lys Ala

<210> SEQ ID NO 155
<211> LENGTH: 100
<212> TYPE: PRT
<213> ORGANISM: Neisseria gonorrhoeae

<400> SEQUENCE: 155

Met Thr Ala Gln His Gln Ser Asp Thr Leu Leu His Arg Leu Asn Thr
1               5                   10                  15

Leu Pro Pro Lys Arg Tyr Gly Val Phe Leu Leu Asn Asp Asp Tyr Thr
            20                  25                  30

Thr Met Glu Phe Val Val Glu Ile Leu Thr Glu Ile Phe Met Leu Gly
        35                  40                  45

Gln Glu Gln Ala Val Ala Val Met Leu Ser Val His His Glu Gly Lys

```
                50                  55                  60
Gly Leu Cys Gly Thr Tyr Thr Arg Asp Ile Ala Gln Thr Lys Gln Gln
 65                  70                  75                  80

Gln Val Met Gln Arg Ala Lys Ala Glu Gly His Pro Leu Gln Cys Ile
                 85                  90                  95

Val Glu Glu Ile
            100
```

<210> SEQ ID NO 156
<211> LENGTH: 96
<212> TYPE: PRT
<213> ORGANISM: Campylobacter jejuni

<400> SEQUENCE: 156

```
Met Pro Lys Thr Gln Thr Leu Glu Gln Thr Lys Leu Ser Glu Pro Lys
 1               5                  10                  15

Met Tyr Lys Val Ile Leu Leu Asn Asp Val Thr Thr Met Asp Phe
                20                  25                  30

Val Ile Glu Ile Leu Met Asn Ile Phe His Gln Asn Leu Glu Lys Ala
             35                  40                  45

Ser Gln Thr Met Leu Glu Ile His His Asn Gly Ser Gly Ile Cys Gly
         50                  55                  60

Ile Tyr Thr Gln Glu Ile Ala Leu Ser Lys Gln Lys Val Met Asp
 65                  70                  75                  80

Ala Ala Lys Leu Ala Asn Phe Pro Leu Gln Ala Lys Val Glu Glu Glu
                 85                  90                  95
```

<210> SEQ ID NO 157
<211> LENGTH: 106
<212> TYPE: PRT
<213> ORGANISM: Acinetobacter baylyi

<400> SEQUENCE: 157

```
Met Gly Asp Ser Gln Ser Asp Glu Pro Glu Gly Asp Ile Ala Val Gln
 1               5                  10                  15

Thr Ala Pro Pro Glu Leu Lys Arg Pro Pro Leu Tyr Ala Val Val Leu
                20                  25                  30

Leu Asn Asp Asp Tyr Thr Pro Met Asp Phe Val Ile Glu Ile Leu Gln
             35                  40                  45

Gln Tyr Phe Ala Leu Asn Leu Asp Gln Ala Thr Gln Val Met Leu Thr
         50                  55                  60

Val His Tyr Glu Gly Lys Gly Val Ala Gly Val Tyr Pro Arg Asp Ile
 65                  70                  75                  80

Ala Glu Thr Lys Ala Asn Gln Val Asn Asn Tyr Ala Arg Ser Gln Gly
                 85                  90                  95

His Pro Leu Leu Cys Gln Ile Glu Pro Lys
            100                 105
```

<210> SEQ ID NO 158
<211> LENGTH: 105
<212> TYPE: PRT
<213> ORGANISM: Aeromonas salmonicida

<400> SEQUENCE: 158

```
Met Ser Lys Gln Lys Glu Leu Phe Ala Asn Glu Glu Ile Ala Gln Ala
 1               5                  10                  15

Glu Lys Thr Lys Leu Gln Pro Pro Met Tyr Lys Val Val Leu Asn
                20                  25                  30
```

Asn Asp Asp Tyr Thr Pro Met Glu Phe Val Val Glu Val Leu Gln Lys
            35                  40                  45

Phe Phe Gly Met Asp Leu Asp Lys Ala Thr Gln Val Met Leu Ser Val
 50                  55                  60

His Tyr Ser Gly Lys Gly Val Cys Gly Thr Phe Thr Ala Glu Ile Ala
 65                  70                  75                  80

Glu Thr Lys Val Val Gln Val Asn Thr Tyr Ser Arg Asn Asn Glu His
                 85                  90                  95

Pro Leu Leu Cys Thr Met Glu Lys Ala
             100                 105

<210> SEQ ID NO 159
<211> LENGTH: 100
<212> TYPE: PRT
<213> ORGANISM: Saccharomyces cerevisiae

<400> SEQUENCE: 159

Asp Gly Thr Thr Thr Ala Lys Thr Ser Pro Ser Asn Ser Pro Glu Ala
 1               5                  10                  15

Ser Pro Ser Leu Ala Lys Ile Asp Pro Glu Asn Tyr Thr Val Ile Ile
                 20                  25                  30

Tyr Asn Asp Glu Tyr His Asn Tyr Ser Gln Ala Thr Thr Ala Leu Arg
             35                  40                  45

Gln Gly Val Pro Asp Asn Val His Ile Asp Leu Leu Thr Ser Arg Ile
 50                  55                  60

Asp Gly Glu Gly Arg Ala Met Leu Lys Cys Ser Gln Asp Leu Ser Ser
 65                  70                  75                  80

Val Leu Gly Gly Phe Phe Ala Val Gln Thr Asn Gly Leu Ser Ala Thr
                 85                  90                  95

Leu Thr Ser Trp
            100

<210> SEQ ID NO 160
<211> LENGTH: 102
<212> TYPE: PRT
<213> ORGANISM: Homo sapiens

<400> SEQUENCE: 160

Met Thr Ile Trp Glu Glu Lys Glu Leu Pro Pro Glu Leu Gln Ile
 1               5                  10                  15

Arg Glu Lys Asn Glu Arg Tyr Tyr Cys Val Leu Phe Asn Asp Glu His
                 20                  25                  30

His Ser Tyr Asp His Val Ile Tyr Ser Leu Gln Arg Ala Leu Asp Cys
             35                  40                  45

Glu Leu Ala Glu Ala Gln Leu His Thr Thr Ala Ile Asp Lys Glu Gly
 50                  55                  60

Arg Arg Ala Val Lys Ala Gly Ala Tyr Ala Ala Cys Gln Glu Ala Lys
 65                  70                  75                  80

Glu Asp Ile Lys Ser His Ser Glu Asn Val Ser Gln His Pro Leu His
                 85                  90                  95

Val Glu Val Leu His Ser
            100